(12) United States Patent
Middelberg et al.

(10) Patent No.: US 11,266,968 B2
(45) Date of Patent: Mar. 8, 2022

(54) MINERALIZING BIOSURFACTANT USED FOR NUCLEATING SILICA

(71) Applicant: THE UNIVERSITY OF QUEENSLAND, St Lucia (AU)

(72) Inventors: Anton Peter Jacob Middelberg, Brookfield (AU); Chun-Xia Zhao, Forest Lake (AU); David Wibowo, St. Lucia (AU); Brenton Charles Peters, Jindalee (AU)

(73) Assignee: The University of Queensland, Queensland (AU)

( * ) Notice: Subject to any disclaimer, the term of this patent is extended or adjusted under 35 U.S.C. 154(b) by 0 days.

(21) Appl. No.: 14/917,181

(22) PCT Filed: Sep. 16, 2014

(86) PCT No.: PCT/AU2014/050234
§ 371 (c)(1),
(2) Date: Mar. 7, 2016

(87) PCT Pub. No.: WO2015/035475
PCT Pub. Date: Mar. 19, 2015

(65) Prior Publication Data
US 2016/0193581 A1 Jul. 7, 2016

(30) Foreign Application Priority Data

Sep. 16, 2013 (AU) ............................... 2013903554

(51) Int. Cl.
*C07K 14/00* (2006.01)
*A61K 38/16* (2006.01)
(Continued)

(52) U.S. Cl.
CPC .............. *B01J 13/06* (2013.01); *A01N 25/28* (2013.01); *A01N 25/30* (2013.01); *A01N 43/56* (2013.01);
(Continued)

(58) Field of Classification Search
None
See application file for complete search history.

(56) References Cited

U.S. PATENT DOCUMENTS

2012/0283379 A1   11/2012   Auger et al.

FOREIGN PATENT DOCUMENTS

WO    2007/112356 A2   10/2007
WO    2010/103514 A1    9/2010
(Continued)

OTHER PUBLICATIONS

Dürr, U., et al. Biochim. Biophys. Acta. (2006). 1758; pp. 1408-1425.*
(Continued)

*Primary Examiner* — Kevin S Orwig
(74) *Attorney, Agent, or Firm* — Nixon & Vanderhye, PC

(57) ABSTRACT

The present invention relates to emulsion-templated silica micro and nano-capsules- and methods for making them. In particular, the template emulsion is stabilized by a biosurfactant that also assists in nucleating the silica shell Mineralizing biosurfactants and stabilized micro- and nano-emulsions useful in forming the emulsion-templated micro- and nano-capsules, and methods for the use of the silica micro- and nano-capsules are also described.

24 Claims, 10 Drawing Sheets

Specification includes a Sequence Listing.

(51) Int. Cl.

| | | |
|---|---|---|
| B01J 13/06 | (2006.01) | |
| B01F 17/00 | (2006.01) | |
| C07K 7/06 | (2006.01) | |
| A61K 9/51 | (2006.01) | |
| A61K 9/107 | (2006.01) | |
| C07K 7/08 | (2006.01) | |
| A61K 38/10 | (2006.01) | |
| A01N 25/28 | (2006.01) | |
| A01N 25/30 | (2006.01) | |
| A01N 43/56 | (2006.01) | |
| B82Y 5/00 | (2011.01) | |
| A61K 9/50 | (2006.01) | |

(52) U.S. Cl.
CPC .......... *A61K 9/1075* (2013.01); *A61K 9/5115* (2013.01); *A61K 9/5169* (2013.01); *A61K 38/10* (2013.01); *B01F 17/005* (2013.01); *C07K 7/06* (2013.01); *C07K 7/08* (2013.01); *C07K 14/00* (2013.01); *C07K 14/001* (2013.01); *A61K 9/501* (2013.01); *A61K 9/5031* (2013.01); *A61K 9/5052* (2013.01); *A61K 9/5123* (2013.01); *A61K 9/5146* (2013.01); *A61K 38/16* (2013.01); *B82Y 5/00* (2013.01)

(56) References Cited

FOREIGN PATENT DOCUMENTS

| WO | 2010/121307 A1 | 10/2010 | | |
|---|---|---|---|---|
| WO | WO 2010/121307 | 10/2010 | | |
| WO | WO 2012/079125 | * | 6/2012 | ............... C07K 7/06 |
| WO | 2013/185178 A1 | 12/2013 | | |
| WO | WO 2013/185178 | 12/2013 | | |

OTHER PUBLICATIONS

Powers, J.-P., et al. Biochim. Biophys. Acta. (2004). 1698; pp. 239-250 (Year: 2004).*
Schulz, A., et al. J. Mater. Chem. (2011), 21; pp. 9731-9736.*
Tomczak, M. M., et al., Biomimetic Silica Encapsulation of Nanoparticles and Enzymes, Chapter 10; in Biomolecular Catalysis (2008); 986; pp. 171-182.*
Technical Information bulletin from Thermo Electron Corp. 2004; 2 pgs.*
Knecht, M. R., et al., Chem. Commun. (2003), 24: 3038-3039.*
Malcolm, A. S., et al. Asia-Pacific J. Chem. Eng. (2007), 2; 362-367.*
Garakani, T., M., et al. Chem. Comm. (Aug. 2012), 48; 10210-10212.*
Cha, J., N., et al. Nature (2000), 403; 289-292.*
Graf, P., et al., ACS Nano (2011), 5(2); 820-833.*
International Search Report for PCT/AU2014/050234, dated Nov. 14, 2014, 4 pages.
Malcolm et al., "Tunable Control if Interfacial Rheology and Emulsion Coalescence", ChemPhysChem., 2009, vol. 10, pp. 778-781.
Yuwono et al., "Peptide Amphiphile Nanofibers Template and Catalyze Silica Nanotube Formation", Langmuir, 2007, vol. 23, pp. 5033-5038.
Xu et al., "Twisted Nanotubes Formed from Ultrashort Amphiphilic PeptideI3K and their Templating for the Fabrication of Silica Nanotubes", Chem. Mater., 2010, vol. 22, pp. 5165-5173.
Zeng et al., "Receptor-Specific Delivery of Protein Antigen to Dendritic Cells by a Nanoemulsion Formed Using Top-Down Non-Covalent Click Self-Assembly", Small, 2013 (first published online Apr. 18, 2013), vol. 9, No. 22, pp. 3736-3742.
Wibowo et al., "Emulsion-templated Silica Nanocapsules Formed Using Bio-Inspired Silification", Chem. Commun., 2014 (first published online Aug. 7, 2014), vol. 50, pp. 11325-11328.
Malcolm, Andrew S., et al., "Tuneable Control of Interfacial Rheology and Emulsion Coalescence," ChemPhysChem, 2009, vol. 10, pp. 778-781.
Xu, Hai, et al., "Twisted Nanotubes Formed from Ultrashort Amphiphilic Peptide I3K and Their Templating for the Fabrication of Silica Nanotubes," Chem. Mater., 2010, vol. 22, pp. 5165-5173.
Yuwono, Virany M., et al., "Peptide Amphiphile Nanofibers Template and Catalyze Silica Nanotube Formation," Langmuir, 2007, vol. 23, pp. 5033-5038.
Zeng, B. J., et al., "Receptor-Specific Delivery of Protein Antigen to Dendritic Cells by a Nanoemulsion Formed Using Top-Down Non-Covalent Click Self-Assembly," Small, 2013 (first published online Apr. 18, 2013), vol. 9, No. 22, pp. 3736-3742.
International Preliminary Report on Patentability and Written Opinion of the International Searching Authority dated Mar. 31, 2016, issued in International Application No. PCT/AU2014/050234.
Extended European Search Report dated Mar. 24, 2017, issued in European Patent Application No. 14843901.1.
Dexter, Annette F., "Designed peptide surfactants (Pepfactants®) for switching emulsions and foams," The Australian Institute for Bioengineering and Nanotechnology, Dec. 2007, 33 pages, XP-055354588.
Dexter, Annette F., et al., "Reversible active switching of the mechanical properties of a peptide film at a fluid-fluid interface," Nature Materials, vol. 5, No. 6, Jun. 2006, pp. 502-506, XP-002505888.

* cited by examiner

SEQUENCE LISTING

```
<160> NUMBER OF SEQ ID NOS: 155

<210> SEQ ID NO 1
<211> LENGTH: 14
<212> TYPE: PRT
<213> ORGANISM: Artificial Sequence
<220> FEATURE:
<223> OTHER INFORMATION: Synthetic

<400> SEQUENCE: 1

Met Lys Gln Leu Ala Asp Ser Val Ser Arg Leu Glu His Ala
1               5                   10

<210> SEQ ID NO 2
<211> LENGTH: 14
<212> TYPE: PRT
<213> ORGANISM: Artificial Sequence
<220> FEATURE:
<223> OTHER INFORMATION: Synthetic

<400> SEQUENCE: 2

Met Lys Gln Leu Ala Asp Ser Val Ser Arg Leu Glu Ser Ala
1               5                   10

<210> SEQ ID NO 3
<211> LENGTH: 14
<212> TYPE: PRT
<213> ORGANISM: Artificial Sequence
<220> FEATURE:
<223> OTHER INFORMATION: Synthetic
```

```
<400> SEQUENCE: 3

Leu Met Gln Leu Ala Arg Gln Val Ser Arg Leu Glu Ser Ala
1               5                   10

<210> SEQ ID NO 4
<211> LENGTH: 14
<212> TYPE: PRT
<213> ORGANISM: Artificial Sequence
<220> FEATURE:
<223> OTHER INFORMATION: Synthetic

<400> SEQUENCE: 4

Met Lys Glu Leu Ala Asp Ser Val Asp Arg Leu Glu Ser Ala
1               5                   10

<210> SEQ ID NO 5
<211> LENGTH: 14
<212> TYPE: PRT
<213> ORGANISM: Artificial Sequence
<220> FEATURE:
<223> OTHER INFORMATION: Synthetic

<400> SEQUENCE: 5

Met Lys Gln Leu Ala Asp Ser Val Ser His Leu Glu His Ala
1               5                   10

<210> SEQ ID NO 6
<211> LENGTH: 14
<212> TYPE: PRT
<213> ORGANISM: Artificial Sequence
<220> FEATURE:
<223> OTHER INFORMATION: Synthetic

<400> SEQUENCE: 6

Met Glu Glu Leu Ala Asp Ser Val Glu Glu Leu Glu Ser Ala
1               5                   10

<210> SEQ ID NO 7
<211> LENGTH: 14
<212> TYPE: PRT
<213> ORGANISM: Artificial Sequence
<220> FEATURE:
<223> OTHER INFORMATION: Synthetic

<400> SEQUENCE: 7

Met Lys Lys Leu Ala Asp Ser Val Lys Lys Leu Glu Ser Ala
1               5                   10

<210> SEQ ID NO 8
<211> LENGTH: 14
<212> TYPE: PRT
<213> ORGANISM: Artificial Sequence
<220> FEATURE:
<223> OTHER INFORMATION: Synthetic

<400> SEQUENCE: 8

Glu Ile Ser Ala Leu Glu Lys Glu Ile Ser Ala Leu Glu Lys
1               5                   10

<210> SEQ ID NO 9
<211> LENGTH: 14
<212> TYPE: PRT
<213> ORGANISM: Artificial Sequence
<220> FEATURE:
<223> OTHER INFORMATION: Synthetic

<400> SEQUENCE: 9
```

Lys Ile Ser Ala Leu Lys Glu Lys Ile Ser Ala Leu Lys Glu
1               5                   10

<210> SEQ ID NO 10
<211> LENGTH: 14
<212> TYPE: PRT
<213> ORGANISM: Artificial Sequence
<220> FEATURE:
<223> OTHER INFORMATION: Synthetic

<400> SEQUENCE: 10

Met Lys Glu Leu Ala Asp Ser Val Ser Arg Leu Glu His Ala
1               5                   10

<210> SEQ ID NO 11
<211> LENGTH: 14
<212> TYPE: PRT
<213> ORGANISM: Artificial Sequence
<220> FEATURE:
<223> OTHER INFORMATION: Synthetic

<400> SEQUENCE: 11

Ala Lys Ser Leu Ala Glu Ser Val Ser Arg Leu Glu His Ala
1               5                   10

<210> SEQ ID NO 12
<211> LENGTH: 14
<212> TYPE: PRT
<213> ORGANISM: Artificial Sequence
<220> FEATURE:
<223> OTHER INFORMATION: Synthetic

<400> SEQUENCE: 12

Met Lys Gln Leu Ala Asp Ser Leu His Gln Leu Ala Arg Gln
1               5                   10

<210> SEQ ID NO 13
<211> LENGTH: 14
<212> TYPE: PRT
<213> ORGANISM: Artificial Sequence
<220> FEATURE:
<223> OTHER INFORMATION: Synthetic

<400> SEQUENCE: 13

Met Lys Gln Leu Ala Asp Ser Leu Met Gln Leu Ala Arg Gln
1               5                   10

<210> SEQ ID NO 14
<211> LENGTH: 14
<212> TYPE: PRT
<213> ORGANISM: Artificial Sequence
<220> FEATURE:
<223> OTHER INFORMATION: Synthetic

<400> SEQUENCE: 14

Leu Met Gln Leu Ala Arg Gln Met Lys Gln Leu Ala Asp Ser
1               5                   10

<210> SEQ ID NO 15
<211> LENGTH: 14
<212> TYPE: PRT
<213> ORGANISM: Artificial Sequence
<220> FEATURE:
<223> OTHER INFORMATION: Synthetic

<400> SEQUENCE: 15

```
Leu Met Gln Leu Ala Arg Gln Leu Met Gln Leu Ala Arg Gln
1               5                   10
```

<210> SEQ ID NO 16
<211> LENGTH: 14
<212> TYPE: PRT
<213> ORGANISM: Artificial Sequence
<220> FEATURE:
<223> OTHER INFORMATION: Synthetic

<400> SEQUENCE: 16

```
Met Lys Glu Leu Ala Asp Ser Leu Met Gln Leu Ala Arg Gln
1               5                   10
```

<210> SEQ ID NO 17
<211> LENGTH: 14
<212> TYPE: PRT
<213> ORGANISM: Artificial Sequence
<220> FEATURE:
<223> OTHER INFORMATION: Synthetic

<400> SEQUENCE: 17

```
Met Lys Gln Leu Ala Asp Ser Leu His Gln Leu Ala His Gln
1               5                   10
```

<210> SEQ ID NO 18
<211> LENGTH: 14
<212> TYPE: PRT
<213> ORGANISM: Artificial Sequence
<220> FEATURE:
<223> OTHER INFORMATION: Synthetic

<400> SEQUENCE: 18

```
Met Glu Glu Leu Ala Asp Ser Leu Glu Glu Leu Ala Arg Gln
1               5                   10
```

<210> SEQ ID NO 19
<211> LENGTH: 14
<212> TYPE: PRT
<213> ORGANISM: Artificial Sequence
<220> FEATURE:
<223> OTHER INFORMATION: Synthetic

<400> SEQUENCE: 19

```
Met Lys Lys Leu Ala Asp Ser Leu Lys Lys Leu Ala Arg Gln
1               5                   10
```

<210> SEQ ID NO 20
<211> LENGTH: 14
<212> TYPE: PRT
<213> ORGANISM: Artificial Sequence
<220> FEATURE:
<223> OTHER INFORMATION: Synthetic

<400> SEQUENCE: 20

```
Met Lys Gln Leu Ala Asp Ser Leu His Gln Leu Ala His Lys
1               5                   10
```

<210> SEQ ID NO 21
<211> LENGTH: 14
<212> TYPE: PRT
<213> ORGANISM: Artificial Sequence
<220> FEATURE:
<223> OTHER INFORMATION: Synthetic

<400> SEQUENCE: 21

Met Lys Glu Leu Ala Asp Ser Leu His Glu Leu Ala Arg Glu

```
<210> SEQ ID NO 22
<211> LENGTH: 14
<212> TYPE: PRT
<213> ORGANISM: Artificial Sequence
<220> FEATURE:
<223> OTHER INFORMATION: Synthetic

<400> SEQUENCE: 22

Met Lys Glu Leu Ala Asp Ser Leu His Gln Leu Ala Arg Gln
1               5                   10

<210> SEQ ID NO 23
<211> LENGTH: 14
<212> TYPE: PRT
<213> ORGANISM: Artificial Sequence
<220> FEATURE:
<223> OTHER INFORMATION: Synthetic

<400> SEQUENCE: 23

Met Lys Gln Leu Ala Asp Ser Leu His Glu Leu Ala Arg Gln
1               5                   10

<210> SEQ ID NO 24
<211> LENGTH: 14
<212> TYPE: PRT
<213> ORGANISM: Artificial Sequence
<220> FEATURE:
<223> OTHER INFORMATION: Synthetic

<400> SEQUENCE: 24

Met Lys Glu Leu Ala Asp Ser Leu His Glu Leu Ala Arg Gln
1               5                   10

<210> SEQ ID NO 25
<211> LENGTH: 14
<212> TYPE: PRT
<213> ORGANISM: Artificial Sequence
<220> FEATURE:
<223> OTHER INFORMATION: Synthetic

<400> SEQUENCE: 25

Met Lys Glu Leu Ala Asp Ser Leu His Gln Leu Ala Arg Glu
1               5                   10

<210> SEQ ID NO 26
<211> LENGTH: 14
<212> TYPE: PRT
<213> ORGANISM: Artificial Sequence
<220> FEATURE:
<223> OTHER INFORMATION: Synthetic

<400> SEQUENCE: 26

Met Lys Gln Leu Ala Asp Ser Leu His Glu Leu Ala Arg Glu
1               5                   10

<210> SEQ ID NO 27
<211> LENGTH: 14
<212> TYPE: PRT
<213> ORGANISM: Artificial Sequence
<220> FEATURE:
<223> OTHER INFORMATION: Synthetic

<400> SEQUENCE: 27

Ala Lys Ser Leu Ala Glu Ser Leu His Ser Leu Ala Arg Ser
1               5                   10
```

<210> SEQ ID NO 28
<211> LENGTH: 14
<212> TYPE: PRT
<213> ORGANISM: Artificial Sequence
<220> FEATURE:
<223> OTHER INFORMATION: Synthetic

<400> SEQUENCE: 28

Leu His Gln Leu Ala Arg Gln Val Ser Arg Leu Glu His Ala
1               5                   10

<210> SEQ ID NO 29
<211> LENGTH: 14
<212> TYPE: PRT
<213> ORGANISM: Artificial Sequence
<220> FEATURE:
<223> OTHER INFORMATION: Synthetic

<400> SEQUENCE: 29

Leu His Gln Leu Ala Arg Gln Val Ser Arg Leu Glu His Ala
1               5                   10

<210> SEQ ID NO 30
<211> LENGTH: 14
<212> TYPE: PRT
<213> ORGANISM: Artificial Sequence
<220> FEATURE:
<223> OTHER INFORMATION: Synthetic

<400> SEQUENCE: 30

Leu Met Gln Leu Ala Arg Gln Val Ser Arg Leu Glu Ser Ala
1               5                   10

<210> SEQ ID NO 31
<211> LENGTH: 14
<212> TYPE: PRT
<213> ORGANISM: Artificial Sequence
<220> FEATURE:
<223> OTHER INFORMATION: Synthetic

<400> SEQUENCE: 31

Leu Met Gln Leu Ala Arg Gln Val Asp Arg Leu Glu Ser Ala
1               5                   10

<210> SEQ ID NO 32
<211> LENGTH: 14
<212> TYPE: PRT
<213> ORGANISM: Artificial Sequence
<220> FEATURE:
<223> OTHER INFORMATION: Synthetic

<400> SEQUENCE: 32

Leu His Gln Leu Ala His Gln Val Ser His Leu Glu His Ala
1               5                   10

<210> SEQ ID NO 33
<211> LENGTH: 14
<212> TYPE: PRT
<213> ORGANISM: Artificial Sequence
<220> FEATURE:
<223> OTHER INFORMATION: Synthetic

<400> SEQUENCE: 33

Leu Glu Glu Leu Ala Arg Gln Val Glu Glu Leu Glu Ser Ala
1               5                   10

```
<210> SEQ ID NO 34
<211> LENGTH: 14
<212> TYPE: PRT
<213> ORGANISM: Artificial Sequence
<220> FEATURE:
<223> OTHER INFORMATION: Synthetic

<400> SEQUENCE: 34

Leu Lys Lys Leu Ala Arg Gln Val Lys Leu Glu Ser Ala
1               5                   10

<210> SEQ ID NO 35
<211> LENGTH: 14
<212> TYPE: PRT
<213> ORGANISM: Artificial Sequence
<220> FEATURE:
<223> OTHER INFORMATION: Synthetic

<400> SEQUENCE: 35

Leu His Gln Leu Ala His Lys Val Ser His Leu Glu His Ala
1               5                   10

<210> SEQ ID NO 36
<211> LENGTH: 14
<212> TYPE: PRT
<213> ORGANISM: Artificial Sequence
<220> FEATURE:
<223> OTHER INFORMATION: Synthetic

<400> SEQUENCE: 36

Leu His Glu Leu Ala Arg Glu Val Ser Arg Leu Glu His Ala
1               5                   10

<210> SEQ ID NO 37
<211> LENGTH: 14
<212> TYPE: PRT
<213> ORGANISM: Artificial Sequence
<220> FEATURE:
<223> OTHER INFORMATION: Synthetic

<400> SEQUENCE: 37

Leu His Gln Leu Ala Arg Gln Val Ser Arg Leu Glu His Ala
1               5                   10

<210> SEQ ID NO 38
<211> LENGTH: 14
<212> TYPE: PRT
<213> ORGANISM: Artificial Sequence
<220> FEATURE:
<223> OTHER INFORMATION: Synthetic

<400> SEQUENCE: 38

Leu His Glu Leu Ala Arg Gln Val Ser Arg Leu Glu His Ala
1               5                   10

<210> SEQ ID NO 39
<211> LENGTH: 14
<212> TYPE: PRT
<213> ORGANISM: Artificial Sequence
<220> FEATURE:
<223> OTHER INFORMATION: Synthetic

<400> SEQUENCE: 39

Leu His Glu Leu Ala Arg Gln Val Ser Arg Leu Glu His Ala
1               5                   10
```

```
<210> SEQ ID NO 40
<211> LENGTH: 14
<212> TYPE: PRT
<213> ORGANISM: Artificial Sequence
<220> FEATURE:
<223> OTHER INFORMATION: Synthetic

<400> SEQUENCE: 40

Leu His Gln Leu Ala Arg Glu Val Ser Arg Leu Glu His Ala
1               5                   10

<210> SEQ ID NO 41
<211> LENGTH: 14
<212> TYPE: PRT
<213> ORGANISM: Artificial Sequence
<220> FEATURE:
<223> OTHER INFORMATION: Synthetic

<400> SEQUENCE: 41

Leu His Ser Leu Ala Arg Ser Val Ser Arg Leu Glu His Ala
1               5                   10

<210> SEQ ID NO 42
<211> LENGTH: 14
<212> TYPE: PRT
<213> ORGANISM: Artificial Sequence
<220> FEATURE:
<223> OTHER INFORMATION: Synthetic

<400> SEQUENCE: 42

Ala Lys Ser Val Ala Glu Ser Leu His Ser Leu Ala Arg Ser
1               5                   10

<210> SEQ ID NO 43
<211> LENGTH: 14
<212> TYPE: PRT
<213> ORGANISM: Artificial Sequence
<220> FEATURE:
<223> OTHER INFORMATION: Synthetic

<400> SEQUENCE: 43

Ala His Ser Val Ala Glu Ser Leu His Ser Leu Ala Arg Ser
1               5                   10

<210> SEQ ID NO 44
<211> LENGTH: 14
<212> TYPE: PRT
<213> ORGANISM: Artificial Sequence
<220> FEATURE:
<223> OTHER INFORMATION: Synthetic

<400> SEQUENCE: 44

Ala His Ser Val Ala Lys Ser Leu His Ser Leu Ala Arg Ser
1               5                   10

<210> SEQ ID NO 45
<211> LENGTH: 14
<212> TYPE: PRT
<213> ORGANISM: Artificial Sequence
<220> FEATURE:
<223> OTHER INFORMATION: Synthetic

<400> SEQUENCE: 45

Ala His Ser Val Ala Glu Ser Leu His Ser Leu Ala Glu Ser
1               5                   10

<210> SEQ ID NO 46
```

```
<211> LENGTH: 14
<212> TYPE: PRT
<213> ORGANISM: Artificial Sequence
<220> FEATURE:
<223> OTHER INFORMATION: Synthetic

<400> SEQUENCE: 46

Ala Gln Ser Val Ala Gln Ser Leu Ala Gln Leu Ala Gln Ser
1               5                   10

<210> SEQ ID NO 47
<211> LENGTH: 14
<212> TYPE: PRT
<213> ORGANISM: Artificial Sequence
<220> FEATURE:
<223> OTHER INFORMATION: Synthetic

<400> SEQUENCE: 47

Ala Glu Ser Val Ala Glu Ser Leu Ala Glu Leu Ala Glu Ser
1               5                   10

<210> SEQ ID NO 48
<211> LENGTH: 14
<212> TYPE: PRT
<213> ORGANISM: Artificial Sequence
<220> FEATURE:
<223> OTHER INFORMATION: Synthetic

<400> SEQUENCE: 48

Ala Asn Ser Val Ala Asn Ser Leu Ala Asn Leu Ala Asn Ser
1               5                   10

<210> SEQ ID NO 49
<211> LENGTH: 14
<212> TYPE: PRT
<213> ORGANISM: Artificial Sequence
<220> FEATURE:
<223> OTHER INFORMATION: Synthetic

<400> SEQUENCE: 49

Ala Asp Ser Val Ala Asp Ser Leu Ala Asp Leu Ala Asp Ser
1               5                   10

<210> SEQ ID NO 50
<211> LENGTH: 14
<212> TYPE: PRT
<213> ORGANISM: Artificial Sequence
<220> FEATURE:
<223> OTHER INFORMATION: Synthetic

<400> SEQUENCE: 50

Ala Gln Ser Val Ala Glu Ser Leu Ala Gln Leu Ala Glu Ser
1               5                   10

<210> SEQ ID NO 51
<211> LENGTH: 14
<212> TYPE: PRT
<213> ORGANISM: Artificial Sequence
<220> FEATURE:
<223> OTHER INFORMATION: Synthetic

<400> SEQUENCE: 51

Ala Glu Ser Val Ala Glu Ser Leu Ala Glu Leu Ala Glu Ser
1               5                   10

<210> SEQ ID NO 52
<211> LENGTH: 14
```

```
<212> TYPE: PRT
<213> ORGANISM: Artificial Sequence
<220> FEATURE:
<223> OTHER INFORMATION: Synthetic

<400> SEQUENCE: 52

Ala Asn Ser Val Ala Glu Ser Leu Ala Asn Leu Ala Glu Ser
1               5                   10

<210> SEQ ID NO 53
<211> LENGTH: 14
<212> TYPE: PRT
<213> ORGANISM: Artificial Sequence
<220> FEATURE:
<223> OTHER INFORMATION: Synthetic

<400> SEQUENCE: 53

Ala Asp Ser Val Ala Glu Ser Leu Ala Asp Leu Ala Glu Ser
1               5                   10

<210> SEQ ID NO 54
<211> LENGTH: 21
<212> TYPE: PRT
<213> ORGANISM: Artificial Sequence
<220> FEATURE:
<223> OTHER INFORMATION: Synthetic

<400> SEQUENCE: 54

Met Lys Gln Leu Ala Asp Ser Leu His Gln Leu Ala Arg Gln Val Ser
1               5                   10                  15

Arg Leu Glu His Ala
            20

<210> SEQ ID NO 55
<211> LENGTH: 21
<212> TYPE: PRT
<213> ORGANISM: Artificial Sequence
<220> FEATURE:
<223> OTHER INFORMATION: Synthetic

<400> SEQUENCE: 55

Met Lys Gln Leu Ala Asp Ser Leu His Gln Leu Ala Arg Gln Val Ser
1               5                   10                  15

Arg Leu Glu His Ala
            20

<210> SEQ ID NO 56
<211> LENGTH: 21
<212> TYPE: PRT
<213> ORGANISM: Artificial Sequence
<220> FEATURE:
<223> OTHER INFORMATION: Synthetic

<400> SEQUENCE: 56

Met Lys Gln Leu Ala Asp Ser Leu Met Gln Leu Ala Arg Gln Val Ser
1               5                   10                  15

Arg Leu Glu Ser Ala
            20

<210> SEQ ID NO 57
<211> LENGTH: 28
<212> TYPE: PRT
<213> ORGANISM: Artificial Sequence
<220> FEATURE:
<223> OTHER INFORMATION: Synthetic
```

<400> SEQUENCE: 57

Leu Met Gln Leu Ala Arg Gln Met Lys Gln Leu Ala Asp Ser Leu Met
1               5                   10                  15
Gln Leu Ala Arg Gln Val Ser Arg Leu Glu Ser Ala
            20                  25

<210> SEQ ID NO 58
<211> LENGTH: 21
<212> TYPE: PRT
<213> ORGANISM: Artificial Sequence
<220> FEATURE:
<223> OTHER INFORMATION: Synthetic

<400> SEQUENCE: 58

Met Lys Glu Leu Ala Asp Ser Leu Met Gln Leu Ala Arg Gln Val Asp
1               5                   10                  15
Arg Leu Glu Ser Ala
            20

<210> SEQ ID NO 59
<211> LENGTH: 21
<212> TYPE: PRT
<213> ORGANISM: Artificial Sequence
<220> FEATURE:
<223> OTHER INFORMATION: Synthetic

<400> SEQUENCE: 59

Met Lys Gln Leu Ala Asp Ser Leu His Gln Leu Ala His Gln Val Ser
1               5                   10                  15
His Leu Glu His Ala
            20

<210> SEQ ID NO 60
<211> LENGTH: 21
<212> TYPE: PRT
<213> ORGANISM: Artificial Sequence
<220> FEATURE:
<223> OTHER INFORMATION: Synthetic

<400> SEQUENCE: 60

Met Glu Glu Leu Ala Asp Ser Leu Glu Gln Leu Ala Arg Gln Val Glu
1               5                   10                  15
Glu Leu Glu Ser Ala
            20

<210> SEQ ID NO 61
<211> LENGTH: 21
<212> TYPE: PRT
<213> ORGANISM: Artificial Sequence
<220> FEATURE:
<223> OTHER INFORMATION: Synthetic

<400> SEQUENCE: 61

Met Lys Lys Leu Ala Asp Ser Leu Lys Lys Leu Ala Arg Gln Val Lys
1               5                   10                  15
Lys Leu Glu Ser Ala
            20

<210> SEQ ID NO 62
<211> LENGTH: 21
<212> TYPE: PRT
<213> ORGANISM: Artificial Sequence
<220> FEATURE:
<223> OTHER INFORMATION: Synthetic

```
<400> SEQUENCE: 62

Met Lys Gln Leu Ala Asp Ser Leu His Gln Leu Ala His Lys Val Ser
1               5                   10                  15

His Leu Glu His Ala
            20

<210> SEQ ID NO 63
<211> LENGTH: 21
<212> TYPE: PRT
<213> ORGANISM: Artificial Sequence
<220> FEATURE:
<223> OTHER INFORMATION: Synthetic

<400> SEQUENCE: 63

Glu Ile Ser Ala Leu Glu Lys Glu Ile Ser Ala Leu Glu Lys Glu Ile
1               5                   10                  15

Ser Ala Leu Glu Lys
            20

<210> SEQ ID NO 64
<211> LENGTH: 21
<212> TYPE: PRT
<213> ORGANISM: Artificial Sequence
<220> FEATURE:
<223> OTHER INFORMATION: Synthetic

<400> SEQUENCE: 64

Lys Ile Ser Ala Leu Lys Glu Lys Ile Ser Ala Leu Lys Glu Lys Ile
1               5                   10                  15

Ser Ala Leu Lys Glu
            20

<210> SEQ ID NO 65
<211> LENGTH: 21
<212> TYPE: PRT
<213> ORGANISM: Artificial Sequence
<220> FEATURE:
<223> OTHER INFORMATION: Synthetic

<400> SEQUENCE: 65

Met Lys Glu Leu Ala Asp Ser Leu His Glu Leu Ala Arg Glu Val Ser
1               5                   10                  15

Arg Leu Glu His Ala
            20

<210> SEQ ID NO 66
<211> LENGTH: 21
<212> TYPE: PRT
<213> ORGANISM: Artificial Sequence
<220> FEATURE:
<223> OTHER INFORMATION: Synthetic

<400> SEQUENCE: 66

Met Lys Glu Leu Ala Asp Ser Leu His Gln Leu Ala Arg Gln Val Ser
1               5                   10                  15

Arg Leu Glu His Ala
            20

<210> SEQ ID NO 67
<211> LENGTH: 21
<212> TYPE: PRT
<213> ORGANISM: Artificial Sequence
<220> FEATURE:
```

<223> OTHER INFORMATION: Synthetic

<400> SEQUENCE: 67

Met Lys Gln Leu Ala Asp Ser Leu His Glu Leu Ala Arg Gln Val Ser
1               5                   10                  15

Arg Leu Glu His Ala
            20

<210> SEQ ID NO 68
<211> LENGTH: 21
<212> TYPE: PRT
<213> ORGANISM: Artificial Sequence
<220> FEATURE:
<223> OTHER INFORMATION: Synthetic

<400> SEQUENCE: 68

Met Lys Gln Leu Ala Asp Ser Leu His Gln Leu Ala Arg Gln Val Ser
1               5                   10                  15

Arg Leu Glu His Ala
            20

<210> SEQ ID NO 69
<211> LENGTH: 21
<212> TYPE: PRT
<213> ORGANISM: Artificial Sequence
<220> FEATURE:
<223> OTHER INFORMATION: Synthetic

<400> SEQUENCE: 69

Met Lys Glu Leu Ala Asp Ser Leu His Glu Leu Ala Arg Gln Val Ser
1               5                   10                  15

Arg Leu Glu His Ala
            20

<210> SEQ ID NO 70
<211> LENGTH: 21
<212> TYPE: PRT
<213> ORGANISM: Artificial Sequence
<220> FEATURE:
<223> OTHER INFORMATION: Synthetic

<400> SEQUENCE: 70

Met Lys Glu Leu Ala Asp Ser Leu His Gln Leu Ala Arg Glu Val Ser
1               5                   10                  15

Arg Leu Glu His Ala
            20

<210> SEQ ID NO 71
<211> LENGTH: 21
<212> TYPE: PRT
<213> ORGANISM: Artificial Sequence
<220> FEATURE:
<223> OTHER INFORMATION: Synthetic

<400> SEQUENCE: 71

Met Lys Gln Leu Ala Asp Ser Leu His Glu Leu Ala Arg Glu Val Ser
1               5                   10                  15

Arg Leu Glu His Ala
            20

<210> SEQ ID NO 72
<211> LENGTH: 21
<212> TYPE: PRT
<213> ORGANISM: Artificial Sequence
<220> FEATURE:
<223> OTHER INFORMATION: Synthetic

<400> SEQUENCE: 72

Ala Lys Ser Leu Ala Glu Ser Leu His Ser Leu Ala Arg Ser Val Ser
1               5                   10                  15

Arg Leu Glu His Ala
            20

<210> SEQ ID NO 73
<211> LENGTH: 22
<212> TYPE: PRT
<213> ORGANISM: Artificial Sequence
<220> FEATURE:
<223> OTHER INFORMATION: Synthetic

<400> SEQUENCE: 73

Ala Lys Ser Val Ala Glu Ser Leu His Ser Leu Ala Arg Ser Val Ser
1               5                   10                  15

Arg Leu Val Glu His Ala
            20

<210> SEQ ID NO 74
<211> LENGTH: 22
<212> TYPE: PRT
<213> ORGANISM: Artificial Sequence
<220> FEATURE:
<223> OTHER INFORMATION: Synthetic

<400> SEQUENCE: 74

Ala His Ser Val Ala Glu Ser Leu His Ser Leu Ala Arg Ser Val Ser
1               5                   10                  15

Arg Leu Val Glu His Ala
            20

<210> SEQ ID NO 75
<211> LENGTH: 22
<212> TYPE: PRT
<213> ORGANISM: Artificial Sequence
<220> FEATURE:
<223> OTHER INFORMATION: Synthetic

<400> SEQUENCE: 75

Ala His Ser Val Ala Lys Ser Leu His Ser Leu Ala Arg Ser Val Ser
1               5                   10                  15

Arg Leu Val Ser His Ala
            20

<210> SEQ ID NO 76
<211> LENGTH: 22
<212> TYPE: PRT
<213> ORGANISM: Artificial Sequence
<220> FEATURE:
<223> OTHER INFORMATION: Synthetic

<400> SEQUENCE: 76

Ala His Ser Val Ala Glu Ser Leu His Ser Leu Ala Glu Ser Val Ser
1               5                   10                  15

Glu Leu Val Ser His Ala
            20

<210> SEQ ID NO 77
<211> LENGTH: 22
<212> TYPE: PRT

<213> ORGANISM: Artificial Sequence
<220> FEATURE:
<223> OTHER INFORMATION: Synthetic

<400> SEQUENCE: 77

Ala Gln Ser Val Ala Gln Ser Leu Ala Gln Leu Ala Gln Ser Val Ser
1               5                   10                  15

Gln Leu Val Ser Gln Ala
            20

<210> SEQ ID NO 78
<211> LENGTH: 22
<212> TYPE: PRT
<213> ORGANISM: Artificial Sequence
<220> FEATURE:
<223> OTHER INFORMATION: Synthetic

<400> SEQUENCE: 78

Ala Glu Ser Val Ala Glu Ser Leu Ala Glu Leu Ala Glu Ser Val Ser
1               5                   10                  15

Glu Leu Val Ser Glu Ala
            20

<210> SEQ ID NO 79
<211> LENGTH: 22
<212> TYPE: PRT
<213> ORGANISM: Artificial Sequence
<220> FEATURE:
<223> OTHER INFORMATION: Synthetic

<400> SEQUENCE: 79

Ala Asn Ser Val Ala Asn Ser Leu Ala Asn Leu Ala Asn Ser Val Ser
1               5                   10                  15

Asn Leu Val Ser Asn Ala
            20

<210> SEQ ID NO 80
<211> LENGTH: 22
<212> TYPE: PRT
<213> ORGANISM: Artificial Sequence
<220> FEATURE:
<223> OTHER INFORMATION: Synthetic

<400> SEQUENCE: 80

Ala Asp Ser Val Ala Asp Ser Leu Ala Asp Leu Ala Asp Ser Val Ser
1               5                   10                  15

Pro Leu Val Ser Asp Ala
            20

<210> SEQ ID NO 81
<211> LENGTH: 22
<212> TYPE: PRT
<213> ORGANISM: Artificial Sequence
<220> FEATURE:
<223> OTHER INFORMATION: Synthetic

<400> SEQUENCE: 81

Ala Gln Ser Val Ala Glu Ser Leu Ala Gln Leu Ala Glu Ser Val Ser
1               5                   10                  15

Glu Leu Val Ser Gln Ala
            20

<210> SEQ ID NO 82
<211> LENGTH: 22

```
<212> TYPE: PRT
<213> ORGANISM: Artificial Sequence
<220> FEATURE:
<223> OTHER INFORMATION: Synthetic

<400> SEQUENCE: 82

Ala Glu Ser Val Ala Glu Ser Leu Ala Glu Leu Ala Glu Ser Val Ser
1               5                   10                  15
Glu Leu Val Ser Glu Ala
            20

<210> SEQ ID NO 83
<211> LENGTH: 22
<212> TYPE: PRT
<213> ORGANISM: Artificial Sequence
<220> FEATURE:
<223> OTHER INFORMATION: Synthetic

<400> SEQUENCE: 83

Ala Asn Ser Val Ala Glu Ser Leu Ala Asn Leu Ala Glu Ser Val Ser
1               5                   10                  15
Glu Leu Val Ser Asn Ala
            20

<210> SEQ ID NO 84
<211> LENGTH: 22
<212> TYPE: PRT
<213> ORGANISM: Artificial Sequence
<220> FEATURE:
<223> OTHER INFORMATION: Synthetic

<400> SEQUENCE: 84

Ala Asp Ser Val Ala Glu Ser Leu Ala Asp Leu Ala Glu Ser Val Ser
1               5                   10                  15
Glu Leu Val Ser Asp Ala
            20

<210> SEQ ID NO 85
<211> LENGTH: 50
<212> TYPE: PRT
<213> ORGANISM: Artificial Sequence
<220> FEATURE:
<223> OTHER INFORMATION: Synthetic

<400> SEQUENCE: 85

Met Asp Pro Ser Met Lys Gln Leu Ala Asp Ser Leu His Gln Leu Ala
1               5                   10                  15
Arg Gln Val Ser Arg Leu Glu His Ala Asp Pro Ser Met Lys Gln Leu
            20                  25                  30
Ala Asp Ser Leu His Gln Leu Ala Arg Gln Val Ser Arg Leu Glu His
        35                  40                  45
Ala Asp
    50

<210> SEQ ID NO 86
<211> LENGTH: 98
<212> TYPE: PRT
<213> ORGANISM: Artificial Sequence
<220> FEATURE:
<223> OTHER INFORMATION: Synthetic

<400> SEQUENCE: 86

Met Asp Pro Ser Met Lys Gln Leu Ala Asp Ser Leu His Gln Leu Ala
1               5                   10                  15
```

Arg Gln Val Ser Arg Leu Glu His Ala Asp Pro Ser Met Lys Gln Leu
            20                  25                  30

Ala Asp Ser Leu His Gln Leu Ala Arg Gln Val Ser Arg Leu Glu His
        35                  40                  45

Ala Asp Pro Ser Met Lys Gln Leu Ala Asp Ser Leu His Gln Leu Ala
    50                  55                  60

Arg Gln Val Ser Arg Leu Glu His Ala Asp Pro Ser Met Lys Gln Leu
65                  70                  75                  80

Ala Asp Ser Leu His Gln Leu Ala Arg Gln Val Ser Arg Leu Glu His
                85                  90                  95

Ala Asp

<210> SEQ ID NO 87
<211> LENGTH: 98
<212> TYPE: PRT
<213> ORGANISM: Artificial Sequence
<220> FEATURE:
<223> OTHER INFORMATION: Synthetic

<400> SEQUENCE: 87

Met Asp Pro Ser Ala Lys Ser Leu Ala Glu Ser Leu His Ser Leu Ala
1               5                   10                  15

Arg Ser Val Ser Arg Leu Glu His Ala Asp Pro Ser Ala Lys Ser Leu
            20                  25                  30

Ala Glu Ser Leu His Ser Leu Ala Arg Ser Val Ser Arg Leu Glu His
        35                  40                  45

Ala Asp Pro Ser Ala Lys Ser Leu Ala Glu Ser Leu His Ser Leu Ala
    50                  55                  60

Arg Ser Val Ser Arg Leu Glu His Ala Asp Pro Ser Ala Lys Ser Leu
65                  70                  75                  80

Ala Glu Ser Leu His Ser Leu Ala Arg Ser Val Ser Arg Leu Glu His
                85                  90                  95

Ala Asp

<210> SEQ ID NO 88
<211> LENGTH: 102
<212> TYPE: PRT
<213> ORGANISM: Artificial Sequence
<220> FEATURE:
<223> OTHER INFORMATION: Synthetic

<400> SEQUENCE: 88

Met Asp Pro Ser Ala Lys Ser Val Ala Glu Ser Leu His Ser Leu Ala
1               5                   10                  15

Arg Ser Val Ser Arg Leu Val Glu His Ala Asp Pro Ser Ala Lys Ser
            20                  25                  30

Val Ala Glu Ser Leu His Ser Leu Ala Arg Ser Val Ser Arg Leu Val
        35                  40                  45

Glu His Ala Asp Pro Ser Ala Lys Ser Val Ala Glu Ser Leu His Ser
    50                  55                  60

Leu Ala Arg Ser Val Ser Arg Leu Val Glu His Ala Asp Pro Ser Ala
65                  70                  75                  80

Lys Ser Val Ala Glu Ser Leu His Ser Leu Ala Arg Ser Val Ser Arg
                85                  90                  95

Leu Val Glu His Ala Asp
            100

<210> SEQ ID NO 89
<211> LENGTH: 102
<212> TYPE: PRT
<213> ORGANISM: Artificial Sequence
<220> FEATURE:
<223> OTHER INFORMATION: Synthetic

<400> SEQUENCE: 89

```
Met Asp Pro Ser Ala His Ser Val Ala Glu Ser Leu His Ser Leu Ala
1               5                   10                  15

Arg Ser Val Ser Arg Leu Val Glu His Ala Asp Pro Ser Ala His Ser
            20                  25                  30

Val Ala Glu Ser Leu His Ser Leu Ala Arg Ser Val Ser Arg Leu Val
        35                  40                  45

Glu His Ala Asp Pro Ser Ala His Ser Val Ala Glu Ser Leu His Ser
    50                  55                  60

Leu Ala Arg Ser Val Ser Arg Leu Val Glu His Ala Asp Pro Ser Ala
65                  70                  75                  80

His Ser Val Ala Glu Ser Leu His Ser Leu Ala Arg Ser Val Ser Arg
                85                  90                  95

Leu Val Glu His Ala Asp
            100
```

<210> SEQ ID NO 90
<211> LENGTH: 102
<212> TYPE: PRT
<213> ORGANISM: Artificial Sequence
<220> FEATURE:
<223> OTHER INFORMATION: Synthetic

<400> SEQUENCE: 90

```
Met Asp Pro Ser Ala His Ser Val Ala Lys Ser Leu His Ser Leu Ala
1               5                   10                  15

Arg Ser Val Ser Arg Leu Val Ser His Ala Asp Pro Ser Ala His Ser
            20                  25                  30

Val Ala Lys Ser Leu His Ser Leu Ala Arg Ser Val Ser Arg Leu Val
        35                  40                  45

Ser His Ala Asp Pro Ser Ala His Ser Val Ala Lys Ser Leu His Ser
    50                  55                  60

Leu Ala Arg Ser Val Ser Arg Leu Val Ser His Ala Asp Pro Ser Ala
65                  70                  75                  80

His Ser Val Ala Lys Ser Leu His Ser Leu Ala Arg Ser Val Ser Arg
                85                  90                  95

Leu Val Ser His Ala Asp
            100
```

<210> SEQ ID NO 91
<211> LENGTH: 102
<212> TYPE: PRT
<213> ORGANISM: Artificial Sequence
<220> FEATURE:
<223> OTHER INFORMATION: Synthetic

<400> SEQUENCE: 91

```
Met Asp Pro Ser Ala His Ser Val Ala Glu Ser Leu His Ser Leu Ala
1               5                   10                  15

Glu Ser Val Ser Glu Leu Val Ser His Ala Asp Pro Ser Ala His Ser
            20                  25                  30

Val Ala Glu Ser Leu His Ser Leu Ala Glu Ser Val Ser Glu Leu Val
```

```
                35                  40                  45
Ser His Ala Asp Pro Ser Ala His Ser Val Ala Glu Ser Leu His Ser
 50                  55                  60
Leu Ala Glu Ser Val Ser Glu Leu Val Ser His Ala Asp Pro Ser Ala
 65                  70                  75                  80
His Ser Val Ala Glu Ser Leu His Ser Leu Ala Glu Ser Val Ser Glu
                 85                  90                  95
Leu Val Ser His Ala Asp
            100

<210> SEQ ID NO 92
<211> LENGTH: 102
<212> TYPE: PRT
<213> ORGANISM: Artificial Sequence
<220> FEATURE:
<223> OTHER INFORMATION: Synthetic

<400> SEQUENCE: 92

Met Asp Pro Ser Ala Gln Ser Val Ala Gln Ser Leu Ala Gln Leu Ala
 1               5                  10                  15
Gln Ser Val Ser Gln Leu Val Ser Gln Ala Asp Pro Ser Ala Gln Ser
                20                  25                  30
Val Ala Gln Ser Leu Ala Gln Leu Ala Gln Ser Val Ser Gln Leu Val
                35                  40                  45
Ser Gln Ala Asp Pro Ser Ala Gln Ser Val Ala Gln Ser Leu Ala Gln
 50                  55                  60
Leu Ala Gln Ser Val Ser Gln Leu Val Ser Gln Ala Asp Pro Ser Ala
 65                  70                  75                  80
Gln Ser Val Ala Gln Ser Leu Ala Gln Leu Ala Gln Ser Val Ser Gln
                 85                  90                  95
Leu Val Ser Gln Ala Asp
            100

<210> SEQ ID NO 93
<211> LENGTH: 102
<212> TYPE: PRT
<213> ORGANISM: Artificial Sequence
<220> FEATURE:
<223> OTHER INFORMATION: Synthetic

<400> SEQUENCE: 93

Met Asp Pro Ser Ala Asn Ser Val Ala Asn Ser Leu Ala Asn Leu Ala
 1               5                  10                  15
Asn Ser Val Ser Asn Leu Val Ser Asn Ala Asp Pro Ser Ala Asn Ser
                20                  25                  30
Val Ala Asn Ser Leu Ala Asn Leu Ala Asn Ser Val Ser Asn Leu Val
                35                  40                  45
Ser Asn Ala Asp Pro Ser Ala Asn Ser Val Ala Asn Ser Leu Ala Asn
 50                  55                  60
Leu Ala Asn Ser Val Ser Asn Leu Val Ser Asn Ala Asp Pro Ser Ala
 65                  70                  75                  80
Asn Ser Val Ala Asn Ser Leu Ala Asn Leu Ala Asn Ser Val Ser Asn
                 85                  90                  95
Leu Val Ser Asn Ala Asp
            100

<210> SEQ ID NO 94
<211> LENGTH: 102
```

-continued

```
<212> TYPE: PRT
<213> ORGANISM: Artificial Sequence
<220> FEATURE:
<223> OTHER INFORMATION: Synthetic

<400> SEQUENCE: 94

Met Asp Pro Ser Ala Gln Ser Val Ala Glu Ser Leu Ala Gln Leu Ala
1               5                   10                  15

Glu Ser Val Ser Glu Leu Val Ser Gln Ala Asp Pro Ser Ala Gln Ser
            20                  25                  30

Val Ala Glu Ser Leu Ala Gln Leu Ala Glu Ser Val Ser Glu Leu Val
        35                  40                  45

Ser Gln Ala Asp Pro Ser Ala Gln Ser Val Ala Glu Ser Leu Ala Gln
    50                  55                  60

Leu Ala Glu Ser Val Ser Glu Leu Val Ser Gln Ala Asp Pro Ser Ala
65                  70                  75                  80

Gln Ser Val Ala Glu Ser Leu Ala Gln Leu Ala Glu Ser Val Ser Glu
                85                  90                  95

Leu Val Ser Gln Ala Asp
            100

<210> SEQ ID NO 95
<211> LENGTH: 102
<212> TYPE: PRT
<213> ORGANISM: Artificial Sequence
<220> FEATURE:
<223> OTHER INFORMATION: Synthetic

<400> SEQUENCE: 95

Met Asp Pro Ser Ala Asn Ser Val Ala Glu Ser Leu Ala Asn Leu Ala
1               5                   10                  15

Glu Ser Val Ser Glu Leu Val Ser Asn Ala Asp Pro Ser Ala Asn Ser
            20                  25                  30

Val Ala Glu Ser Leu Ala Asn Leu Ala Glu Ser Val Ser Glu Leu Val
        35                  40                  45

Ser Asn Ala Asp Pro Ser Ala Asn Ser Val Ala Glu Ser Leu Ala Asn
    50                  55                  60

Leu Ala Glu Ser Val Ser Glu Leu Val Ser Asn Ala Asp Pro Ser Ala
65                  70                  75                  80

Asn Ser Val Ala Glu Ser Leu Ala Asn Leu Ala Glu Ser Val Ser Glu
                85                  90                  95

Leu Val Ser Asn Ala Asp
            100

<210> SEQ ID NO 96
<211> LENGTH: 98
<212> TYPE: PRT
<213> ORGANISM: Artificial Sequence
<220> FEATURE:
<223> OTHER INFORMATION: Synthetic

<400> SEQUENCE: 96

Met Asp Pro Ser Met Lys Gln Leu Ala Asp Ser Leu Met Gln Leu Ala
1               5                   10                  15

Arg Gln Val Ser Arg Leu Glu Ser Ala Asp Pro Ser Met Lys Gln Leu
            20                  25                  30

Ala Asp Ser Leu Met Gln Leu Ala Arg Gln Val Ser Arg Leu Glu Ser
        35                  40                  45

Ala Asp Pro Ser Met Lys Gln Leu Ala Asp Ser Leu Met Gln Leu Ala
```

-continued

```
                 50                  55                  60
Arg Gln Val Ser Arg Leu Glu Ser Ala Asp Pro Ser Met Lys Gln Leu
 65                  70                  75                  80

Ala Asp Ser Leu Met Gln Leu Ala Arg Gln Val Ser Arg Leu Glu Ser
                 85                  90                  95

Ala Asp

<210> SEQ ID NO 97
<211> LENGTH: 122
<212> TYPE: PRT
<213> ORGANISM: Artificial Sequence
<220> FEATURE:
<223> OTHER INFORMATION: Synthetic

<400> SEQUENCE: 97

Met Asp Pro Ser Leu Met Gln Leu Ala Arg Gln Met Lys Gln Leu Ala
  1               5                  10                  15

Asp Ser Leu Met Gln Leu Ala Arg Gln Val Ser Arg Leu Glu Ser Ala
                 20                  25                  30

Pro Ser Leu Met Gln Leu Ala Arg Gln Met Lys Gln Leu Ala Asp Ser
             35                  40                  45

Leu Met Gln Leu Ala Arg Gln Val Ser Arg Leu Glu Ser Ala Pro Ser
 50                  55                  60

Leu Met Gln Leu Ala Arg Gln Met Lys Gln Leu Ala Asp Ser Leu Met
 65                  70                  75                  80

Gln Leu Ala Arg Gln Val Ser Arg Leu Glu Ser Ala Pro Ser Leu Met
                 85                  90                  95

Gln Leu Ala Arg Gln Met Lys Gln Leu Ala Asp Ser Leu Met Gln Leu
            100                 105                 110

Ala Arg Gln Val Ser Arg Leu Glu Ser Ala
            115                 120

<210> SEQ ID NO 98
<211> LENGTH: 98
<212> TYPE: PRT
<213> ORGANISM: Artificial Sequence
<220> FEATURE:
<223> OTHER INFORMATION: Synthetic

<400> SEQUENCE: 98

Met Asp Pro Ser Met Lys Glu Leu Ala Asp Ser Leu Met Gln Leu Ala
  1               5                  10                  15

Arg Gln Val Asp Arg Leu Glu Ser Ala Asp Pro Ser Met Lys Glu Leu
                 20                  25                  30

Ala Asp Ser Leu Met Gln Leu Ala Arg Gln Val Asp Arg Leu Glu Ser
             35                  40                  45

Ala Asp Pro Ser Met Lys Glu Leu Ala Asp Ser Leu Met Gln Leu Ala
 50                  55                  60

Arg Gln Val Asp Arg Leu Glu Ser Ala Asp Pro Ser Met Lys Glu Leu
 65                  70                  75                  80

Ala Asp Ser Leu Met Gln Leu Ala Arg Gln Val Asp Arg Leu Glu Ser
                 85                  90                  95

Ala Asp

<210> SEQ ID NO 99
<211> LENGTH: 98
<212> TYPE: PRT
<213> ORGANISM: Artificial Sequence
```

-continued

```
<220> FEATURE:
<223> OTHER INFORMATION: Synthetic

<400> SEQUENCE: 99

Met Asp Pro Ser Met Lys Gln Leu Ala Asp Ser Leu His Gln Leu Ala
1               5                   10                  15

His Gln Val Ser His Leu Glu His Ala Asp Pro Ser Met Lys Gln Leu
            20                  25                  30

Ala Asp Ser Leu His Gln Leu Ala His Gln Val Ser His Leu Glu His
        35                  40                  45

Ala Asp Pro Ser Met Lys Gln Leu Ala Asp Ser Leu His Gln Leu Ala
    50                  55                  60

His Gln Val Ser His Leu Glu His Ala Asp Pro Ser Met Lys Gln Leu
65                  70                  75                  80

Ala Asp Ser Leu His Gln Leu Ala His Gln Val Ser His Leu Glu His
                85                  90                  95

Ala Asp

<210> SEQ ID NO 100
<211> LENGTH: 98
<212> TYPE: PRT
<213> ORGANISM: Artificial Sequence
<220> FEATURE:
<223> OTHER INFORMATION: Synthetic

<400> SEQUENCE: 100

Met Asp Pro Ser Met Glu Glu Leu Ala Asp Ser Leu Glu Glu Leu Ala
1               5                   10                  15

Arg Gln Val Glu Glu Leu Glu Ser Ala Asp Pro Ser Met Glu Glu Leu
            20                  25                  30

Ala Asp Ser Leu Glu Glu Leu Ala Arg Gln Val Glu Glu Leu Glu Ser
        35                  40                  45

Ala Asp Pro Ser Met Glu Glu Leu Ala Asp Ser Leu Glu Glu Leu Ala
    50                  55                  60

Arg Gln Val Glu Glu Leu Glu Ser Ala Asp Pro Ser Met Glu Glu Leu
65                  70                  75                  80

Ala Asp Ser Leu Glu Glu Leu Ala Arg Gln Val Glu Glu Leu Glu Ser
                85                  90                  95

Ala Asp

<210> SEQ ID NO 101
<211> LENGTH: 98
<212> TYPE: PRT
<213> ORGANISM: Artificial Sequence
<220> FEATURE:
<223> OTHER INFORMATION: Synthetic

<400> SEQUENCE: 101

Met Asp Pro Ser Met Lys Lys Leu Ala Asp Ser Leu Lys Lys Leu Ala
1               5                   10                  15

Arg Gln Val Lys Lys Leu Glu Ser Ala Asp Pro Ser Met Lys Lys Leu
            20                  25                  30

Ala Asp Ser Leu Lys Lys Leu Ala Arg Gln Val Lys Lys Leu Glu Ser
        35                  40                  45

Ala Asp Pro Ser Met Lys Lys Leu Ala Asp Ser Leu Lys Lys Leu Ala
    50                  55                  60

Arg Gln Val Lys Lys Leu Glu Ser Ala Asp Pro Ser Met Lys Lys Leu
65                  70                  75                  80
```

```
Ala Asp Ser Leu Lys Lys Leu Ala Arg Gln Val Lys Lys Leu Glu Ser
                85                  90                  95

Ala Asp

<210> SEQ ID NO 102
<211> LENGTH: 98
<212> TYPE: PRT
<213> ORGANISM: Artificial Sequence
<220> FEATURE:
<223> OTHER INFORMATION: Synthetic

<400> SEQUENCE: 102

Met Asp Pro Ser Met Lys Gln Leu Ala Asp Ser Leu His Gln Leu Ala
1               5                   10                  15

His Lys Val Ser His Leu Glu His Ala Asp Pro Ser Met Lys Gln Leu
            20                  25                  30

Ala Asp Ser Leu His Gln Leu Ala His Lys Val Ser His Leu Glu His
        35                  40                  45

Ala Asp Pro Ser Met Lys Gln Leu Ala Asp Ser Leu His Gln Leu Ala
    50                  55                  60

His Lys Val Ser His Leu Glu His Ala Asp Pro Ser Met Lys Gln Leu
65                  70                  75                  80

Ala Asp Ser Leu His Gln Leu Ala His Lys Val Ser His Leu Glu His
                85                  90                  95

Ala Asp

<210> SEQ ID NO 103
<211> LENGTH: 98
<212> TYPE: PRT
<213> ORGANISM: Artificial Sequence
<220> FEATURE:
<223> OTHER INFORMATION: Synthetic

<400> SEQUENCE: 103

Met Asp Pro Ser Glu Ile Ser Ala Leu Glu Lys Glu Ile Ser Ala Leu
1               5                   10                  15

Glu Lys Glu Ile Ser Ala Leu Glu Lys Asp Pro Ser Glu Ile Ser Ala
            20                  25                  30

Leu Glu Lys Glu Ile Ser Ala Leu Glu Lys Glu Ile Ser Ala Leu Glu
        35                  40                  45

Lys Asp Pro Ser Glu Ile Ser Ala Leu Glu Lys Glu Ile Ser Ala Leu
    50                  55                  60

Glu Lys Glu Ile Ser Ala Leu Glu Lys Asp Pro Ser Glu Ile Ser Ala
65                  70                  75                  80

Leu Glu Lys Glu Ile Ser Ala Leu Glu Lys Glu Ile Ser Ala Leu Glu
                85                  90                  95

Lys Asp

<210> SEQ ID NO 104
<211> LENGTH: 98
<212> TYPE: PRT
<213> ORGANISM: Artificial Sequence
<220> FEATURE:
<223> OTHER INFORMATION: Synthetic

<400> SEQUENCE: 104

Met Asp Pro Ser Lys Ile Ser Ala Leu Lys Glu Lys Ile Ser Ala Leu
1               5                   10                  15
```

```
Lys Glu Lys Ile Ser Ala Leu Lys Glu Asp Pro Ser Lys Ile Ser Ala
            20                  25                  30

Leu Lys Glu Lys Ile Ser Ala Leu Lys Glu Lys Ile Ser Ala Leu Lys
        35                  40                  45

Glu Asp Pro Ser Lys Ile Ser Ala Leu Lys Glu Lys Ile Ser Ala Leu
    50                  55                  60

Lys Glu Lys Ile Ser Ala Leu Lys Glu Asp Pro Ser Lys Ile Ser Ala
65                  70                  75                  80

Leu Lys Glu Lys Ile Ser Ala Leu Lys Glu Lys Ile Ser Ala Leu Lys
                85                  90                  95

Glu Asp
```

<210> SEQ ID NO 105
<211> LENGTH: 98
<212> TYPE: PRT
<213> ORGANISM: Artificial Sequence
<220> FEATURE:
<223> OTHER INFORMATION: Synthetic

<400> SEQUENCE: 105

```
Met Asp Pro Ser Met Lys Glu Leu Ala Asp Ser Leu His Glu Leu Ala
1               5                   10                  15

Arg Glu Val Ser Arg Leu Glu His Ala Asp Pro Ser Met Lys Glu Leu
            20                  25                  30

Ala Asp Ser Leu His Glu Leu Ala Arg Glu Val Ser Arg Leu Glu His
        35                  40                  45

Ala Asp Pro Ser Met Lys Glu Leu Ala Asp Ser Leu His Glu Leu Ala
    50                  55                  60

Arg Glu Val Ser Arg Leu Glu His Ala Asp Pro Ser Met Lys Glu Leu
65                  70                  75                  80

Ala Asp Ser Leu His Glu Leu Ala Arg Glu Val Ser Arg Leu Glu His
                85                  90                  95

Ala Asp
```

<210> SEQ ID NO 106
<211> LENGTH: 98
<212> TYPE: PRT
<213> ORGANISM: Artificial Sequence
<220> FEATURE:
<223> OTHER INFORMATION: Synthetic

<400> SEQUENCE: 106

```
Met Asp Pro Ser Met Lys Glu Leu Ala Asp Ser Leu His Gln Leu Ala
1               5                   10                  15

Arg Gln Val Ser Arg Leu Glu His Ala Asp Pro Ser Met Lys Glu Leu
            20                  25                  30

Ala Asp Ser Leu His Gln Leu Ala Arg Gln Val Ser Arg Leu Glu His
        35                  40                  45

Ala Asp Pro Ser Met Lys Glu Leu Ala Asp Ser Leu His Gln Leu Ala
    50                  55                  60

Arg Gln Val Ser Arg Leu Glu His Ala Asp Pro Ser Met Lys Glu Leu
65                  70                  75                  80

Ala Asp Ser Leu His Gln Leu Ala Arg Gln Val Ser Arg Leu Glu His
                85                  90                  95

Ala Asp
```

<210> SEQ ID NO 107

```
<211> LENGTH: 98
<212> TYPE: PRT
<213> ORGANISM: Artificial Sequence
<220> FEATURE:
<223> OTHER INFORMATION: Synthetic

<400> SEQUENCE: 107

Met Asp Pro Ser Met Lys Gln Leu Ala Asp Ser Leu His Glu Leu Ala
1               5                   10                  15

Arg Gln Val Ser Arg Leu Glu His Ala Asp Pro Ser Met Lys Gln Leu
            20                  25                  30

Ala Asp Ser Leu His Glu Leu Ala Arg Gln Val Ser Arg Leu Glu His
        35                  40                  45

Ala Asp Pro Ser Met Lys Gln Leu Ala Asp Ser Leu His Glu Leu Ala
    50                  55                  60

Arg Gln Val Ser Arg Leu Glu His Ala Asp Pro Ser Met Lys Gln Leu
65                  70                  75                  80

Ala Asp Ser Leu His Glu Leu Ala Arg Gln Val Ser Arg Leu Glu His
                85                  90                  95

Ala Asp

<210> SEQ ID NO 108
<211> LENGTH: 98
<212> TYPE: PRT
<213> ORGANISM: Artificial Sequence
<220> FEATURE:
<223> OTHER INFORMATION: Synthetic

<400> SEQUENCE: 108

Met Asp Pro Ser Met Lys Glu Leu Ala Asp Ser Leu His Glu Leu Ala
1               5                   10                  15

Arg Gln Val Ser Arg Leu Glu His Ala Asp Pro Ser Met Lys Glu Leu
            20                  25                  30

Ala Asp Ser Leu His Glu Leu Ala Arg Gln Val Ser Arg Leu Glu His
        35                  40                  45

Ala Asp Pro Ser Met Lys Glu Leu Ala Asp Ser Leu His Glu Leu Ala
    50                  55                  60

Arg Gln Val Ser Arg Leu Glu His Ala Asp Pro Ser Met Lys Glu Leu
65                  70                  75                  80

Ala Asp Ser Leu His Glu Leu Ala Arg Gln Val Ser Arg Leu Glu His
                85                  90                  95

Ala Asp

<210> SEQ ID NO 109
<211> LENGTH: 98
<212> TYPE: PRT
<213> ORGANISM: Artificial Sequence
<220> FEATURE:
<223> OTHER INFORMATION: Synthetic

<400> SEQUENCE: 109

Met Asp Pro Ser Met Lys Glu Leu Ala Asp Ser Leu His Gln Leu Ala
1               5                   10                  15

Arg Glu Val Ser Arg Leu Glu His Ala Asp Pro Ser Met Lys Glu Leu
            20                  25                  30

Ala Asp Ser Leu His Gln Leu Ala Arg Glu Val Ser Arg Leu Glu His
        35                  40                  45

Ala Asp Pro Ser Met Lys Glu Leu Ala Asp Ser Leu His Gln Leu Ala
    50                  55                  60
```

```
Arg Glu Val Ser Arg Leu Glu His Ala Asp Pro Ser Met Lys Glu Leu
 65                  70                  75                  80

Ala Asp Ser Leu His Gln Leu Ala Arg Glu Val Ser Arg Leu Glu His
                 85                  90                  95

Ala Asp

<210> SEQ ID NO 110
<211> LENGTH: 98
<212> TYPE: PRT
<213> ORGANISM: Artificial Sequence
<220> FEATURE:
<223> OTHER INFORMATION: Synthetic

<400> SEQUENCE: 110

Met Asp Pro Ser Met Lys Gln Leu Ala Asp Ser Leu His Glu Leu Ala
  1               5                  10                  15

Arg Glu Val Ser Arg Leu Glu His Ala Asp Pro Ser Met Lys Gln Leu
                 20                  25                  30

Ala Asp Ser Leu His Glu Leu Ala Arg Glu Val Ser Arg Leu Glu His
                 35                  40                  45

Ala Asp Pro Ser Met Lys Gln Leu Ala Asp Ser Leu His Glu Leu Ala
             50                  55                  60

Arg Glu Val Ser Arg Leu Glu His Ala Asp Pro Ser Met Lys Gln Leu
 65                  70                  75                  80

Ala Asp Ser Leu His Glu Leu Ala Arg Glu Val Ser Arg Leu Glu His
                 85                  90                  95

Ala Asp

<210> SEQ ID NO 111
<211> LENGTH: 102
<212> TYPE: PRT
<213> ORGANISM: Artificial Sequence
<220> FEATURE:
<223> OTHER INFORMATION: Synthetic

<400> SEQUENCE: 111

Met Asp Pro Ser Ala Glu Ser Val Ala Glu Ser Leu Ala Glu Leu Ala
  1               5                  10                  15

Glu Ser Val Ser Glu Leu Val Ser Glu Ala Asp Pro Ser Ala Glu Ser
                 20                  25                  30

Val Ala Glu Ser Leu Ala Glu Leu Ala Glu Ser Val Ser Glu Leu Val
                 35                  40                  45

Ser Glu Ala Asp Pro Ser Ala Glu Ser Val Ala Glu Ser Leu Ala Glu
             50                  55                  60

Leu Ala Glu Ser Val Ser Glu Leu Val Ser Glu Ala Asp Pro Ser Ala
 65                  70                  75                  80

Glu Ser Val Ala Glu Ser Leu Ala Glu Leu Ala Glu Ser Val Ser Glu
                 85                  90                  95

Leu Val Ser Glu Ala Asp
            100

<210> SEQ ID NO 112
<211> LENGTH: 102
<212> TYPE: PRT
<213> ORGANISM: Artificial Sequence
<220> FEATURE:
<223> OTHER INFORMATION: Synthetic

<400> SEQUENCE: 112
```

Met Asp Pro Ser Ala Asp Ser Val Ala Asp Ser Leu Ala Asp Leu Ala
1               5                   10                  15

Asp Ser Val Ser Pro Leu Val Ser Ala Asp Pro Ser Ala Asp Ser
            20                  25                  30

Val Ala Asp Ser Leu Ala Asp Leu Ala Asp Ser Val Ser Pro Leu Val
            35                  40                  45

Ser Asp Ala Asp Pro Ser Ala Asp Ser Val Ala Asp Ser Leu Ala Asp
        50                  55                  60

Leu Ala Asp Ser Val Ser Pro Leu Val Ser Ala Asp Pro Ser Ala
65                  70                  75                  80

Asp Ser Val Ala Asp Ser Leu Ala Asp Leu Ala Asp Ser Val Ser Pro
                85                  90                  95

Leu Val Ser Asp Ala Asp
            100

<210> SEQ ID NO 113
<211> LENGTH: 102
<212> TYPE: PRT
<213> ORGANISM: Artificial Sequence
<220> FEATURE:
<223> OTHER INFORMATION: Synthetic

<400> SEQUENCE: 113

Met Asp Pro Ser Ala Glu Ser Val Ala Glu Ser Leu Ala Glu Leu Ala
1               5                   10                  15

Glu Ser Val Ser Glu Leu Val Ser Glu Ala Asp Pro Ser Ala Glu Ser
            20                  25                  30

Val Ala Glu Ser Leu Ala Glu Leu Ala Glu Ser Val Ser Glu Leu Val
            35                  40                  45

Ser Glu Ala Asp Pro Ser Ala Glu Ser Val Ala Glu Ser Leu Ala Glu
        50                  55                  60

Leu Ala Glu Ser Val Ser Glu Leu Val Ser Glu Ala Asp Pro Ser Ala
65                  70                  75                  80

Glu Ser Val Ala Glu Ser Leu Ala Glu Leu Ala Glu Ser Val Ser Glu
                85                  90                  95

Leu Val Ser Glu Ala Asp
            100

<210> SEQ ID NO 114
<211> LENGTH: 102
<212> TYPE: PRT
<213> ORGANISM: Artificial Sequence
<220> FEATURE:
<223> OTHER INFORMATION: Synthetic

<400> SEQUENCE: 114

Met Asp Pro Ser Ala Asp Ser Val Ala Glu Ser Leu Ala Asp Leu Ala
1               5                   10                  15

Glu Ser Val Ser Glu Leu Val Ser Asp Ala Asp Pro Ser Ala Asp Ser
            20                  25                  30

Val Ala Glu Ser Leu Ala Asp Leu Ala Glu Ser Val Ser Glu Leu Val
            35                  40                  45

Ser Asp Ala Asp Pro Ser Ala Asp Ser Val Ala Glu Ser Leu Ala Asp
        50                  55                  60

Leu Ala Glu Ser Val Ser Glu Leu Val Ser Asp Ala Asp Pro Ser Ala
65                  70                  75                  80

Asp Ser Val Ala Glu Ser Leu Ala Asp Leu Ala Glu Ser Val Ser Glu

```
                85                  90                  95
Leu Val Ser Asp Ala Asp
            100

<210> SEQ ID NO 115
<211> LENGTH: 100
<212> TYPE: PRT
<213> ORGANISM: Artificial Sequence
<220> FEATURE:
<223> OTHER INFORMATION: Synthetic

<400> SEQUENCE: 115

Met Asp Pro Ser Met Lys Gln Leu Ala Asp Ser Leu His Gln Leu Ala
1               5                   10                  15

Arg Gln Val Ser Arg Leu Glu His Ala Asp Pro Ser Met Lys Gln Leu
            20                  25                  30

Ala Asp Ser Leu His Gln Leu Ala Arg Gln Val Ser Arg Leu Glu His
        35                  40                  45

Ala Asp Pro Ser Met Lys Gln Leu Ala Asp Ser Leu His Gln Leu Ala
    50                  55                  60

Arg Gln Val Ser Arg Leu Glu His Ala Asp Pro Ser Met Lys Gln Leu
65                  70                  75                  80

Ala Asp Ser Leu His Gln Leu Ala Arg Gln Val Ser Arg Leu Glu His
                85                  90                  95

Ala Glu Pro Ser
            100

<210> SEQ ID NO 116
<211> LENGTH: 7
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: N-Acetyl-Alanine

<400> SEQUENCE: 116

Xaa Ala Ala Ala Ala Ala Asp
1               5

<210> SEQ ID NO 117
<211> LENGTH: 7
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: N-Acetyl-Valine

<400> SEQUENCE: 117

Xaa Val Val Val Val Val Asp
1               5

<210> SEQ ID NO 118
<211> LENGTH: 8
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
```

```
<222> LOCATION: (1)..(1)
<223> OTHER INFORMATION: N-Acetyl-Valine

<400> SEQUENCE: 118

Xaa Val Val Val Val Val Asp Asp
1               5

<210> SEQ ID NO 119
<211> LENGTH: 8
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: N-Acetyl-Leucine

<400> SEQUENCE: 119

Xaa Leu Leu Leu Leu Leu Asp Asp
1               5

<210> SEQ ID NO 120
<211> LENGTH: 6
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: N-Acetyl-Glycine

<400> SEQUENCE: 120

Xaa Gly Gly Gly Asp Asp
1               5

<210> SEQ ID NO 121
<211> LENGTH: 8
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: N-Acetyl-Glycine

<400> SEQUENCE: 121

Xaa Gly Gly Gly Gly Gly Asp Asp
1               5

<210> SEQ ID NO 122
<211> LENGTH: 10
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: N-Acetyl-Glycine

<400> SEQUENCE: 122

Xaa Gly Gly Gly Gly Gly Gly Gly Asp Asp
1               5                   10

<210> SEQ ID NO 123
<211> LENGTH: 12
```

```
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: N-Acetyl-Glycine

<400> SEQUENCE: 123

Xaa Gly Gly Gly Gly Gly Gly Gly Gly Asp Asp
1               5                   10

<210> SEQ ID NO 124
<211> LENGTH: 8
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: N-Acetyl-Valine

<400> SEQUENCE: 124

Xaa Val Val Val Val Val Lys Lys
1               5

<210> SEQ ID NO 125
<211> LENGTH: 8
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: N-Acetyl-Leucine

<400> SEQUENCE: 125

Xaa Leu Leu Leu Leu Leu Lys Lys
1               5

<210> SEQ ID NO 126
<211> LENGTH: 7
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: N-Acetyl-Alanine

<400> SEQUENCE: 126

Xaa Ala Ala Ala Ala Ala Lys
1               5

<210> SEQ ID NO 127
<211> LENGTH: 7
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: N-Acetyl-Valine

<400> SEQUENCE: 127
```

Xaa Val Val Val Val Val His
1               5

<210> SEQ ID NO 128
<211> LENGTH: 7
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: N-Acetyl-Leucine

<400> SEQUENCE: 128

Xaa Leu Leu Leu Leu Leu Lys
1               5

<210> SEQ ID NO 129
<211> LENGTH: 8
<212> TYPE: PRT
<213> ORGANISM: Artificial Sequence
<220> FEATURE:
<223> OTHER INFORMATION: Synthetic

<400> SEQUENCE: 129

His His Val Val Val Val Val Val
1               5

<210> SEQ ID NO 130
<211> LENGTH: 7
<212> TYPE: PRT
<213> ORGANISM: Artificial Sequence
<220> FEATURE:
<223> OTHER INFORMATION: Synthetic

<400> SEQUENCE: 130

Lys Val Val Val Val Val Val
1               5

<210> SEQ ID NO 131
<211> LENGTH: 19
<212> TYPE: PRT
<213> ORGANISM: Artificial Sequence
<220> FEATURE:
<223> OTHER INFORMATION: Synthetic

<400> SEQUENCE: 131

Ser Ser Lys Lys Ser Gly Ser Tyr Ser Gly Ser Lys Gly Ser Lys Arg
1               5                   10                  15

Arg Ile Leu

<210> SEQ ID NO 132
<211> LENGTH: 16
<212> TYPE: PRT
<213> ORGANISM: Artificial Sequence
<220> FEATURE:
<223> OTHER INFORMATION: Synthetic

<400> SEQUENCE: 132

Arg Lys Lys Arg Lys Lys Arg Lys Lys Arg Lys Lys Gly Gly Gly Tyr
1               5                   10                  15

<210> SEQ ID NO 133
<211> LENGTH: 11
<212> TYPE: PRT
<213> ORGANISM: Artificial Sequence

```
<220> FEATURE:
<223> OTHER INFORMATION: Synthetic

<400> SEQUENCE: 133

Ser Gly Ser Lys Gly Ser Lys Arg Arg Ile Leu
1               5                   10

<210> SEQ ID NO 134
<211> LENGTH: 16
<212> TYPE: PRT
<213> ORGANISM: Artificial Sequence
<220> FEATURE:
<223> OTHER INFORMATION: Synthetic

<400> SEQUENCE: 134

Lys Ser Gly Ser Tyr Ser Gly Ser Lys Gly Ser Lys Arg Arg Ile Leu
1               5                   10                  15

<210> SEQ ID NO 135
<211> LENGTH: 9
<212> TYPE: PRT
<213> ORGANISM: Artificial Sequence
<220> FEATURE:
<223> OTHER INFORMATION: Synthetic

<400> SEQUENCE: 135

Ser Gly Ser Lys Gly Ser Lys Arg Arg
1               5

<210> SEQ ID NO 136
<211> LENGTH: 15
<212> TYPE: PRT
<213> ORGANISM: Artificial Sequence
<220> FEATURE:
<223> OTHER INFORMATION: Synthetic

<400> SEQUENCE: 136

Ser Ser Lys Lys Ser Gly Ser Tyr Ser Gly Ser Lys Gly Ser Lys
1               5                   10                  15

<210> SEQ ID NO 137
<211> LENGTH: 12
<212> TYPE: PRT
<213> ORGANISM: Artificial Sequence
<220> FEATURE:
<223> OTHER INFORMATION: Synthetic

<400> SEQUENCE: 137

Leu Ile Arg Arg Ser Ser Lys Lys Ser Gly Ser Tyr
1               5                   10

<210> SEQ ID NO 138
<211> LENGTH: 12
<212> TYPE: PRT
<213> ORGANISM: Artificial Sequence
<220> FEATURE:
<223> OTHER INFORMATION: Synthetic

<400> SEQUENCE: 138

Ser Ser Lys Lys Ser Gly Ser Tyr Arg Arg Ile Leu
1               5                   10

<210> SEQ ID NO 139
<211> LENGTH: 12
<212> TYPE: PRT
<213> ORGANISM: Artificial Sequence
<220> FEATURE:
```

```
<223> OTHER INFORMATION: Synthetic

<400> SEQUENCE: 139

Ala Pro Pro Gly His His His Trp His Ile His His
1               5                   10

<210> SEQ ID NO 140
<211> LENGTH: 12
<212> TYPE: PRT
<213> ORGANISM: Artificial Sequence
<220> FEATURE:
<223> OTHER INFORMATION: Synthetic

<400> SEQUENCE: 140

Lys Pro Ser His His His His His Thr Gly Ala Asn
1               5                   10

<210> SEQ ID NO 141
<211> LENGTH: 12
<212> TYPE: PRT
<213> ORGANISM: Artificial Sequence
<220> FEATURE:
<223> OTHER INFORMATION: Synthetic

<400> SEQUENCE: 141

Met Ser Pro His Pro His Pro Arg His His His Thr
1               5                   10

<210> SEQ ID NO 142
<211> LENGTH: 12
<212> TYPE: PRT
<213> ORGANISM: Artificial Sequence
<220> FEATURE:
<223> OTHER INFORMATION: Synthetic

<400> SEQUENCE: 142

Met Ser Pro His His Met His His Ser His Gly His
1               5                   10

<210> SEQ ID NO 143
<211> LENGTH: 12
<212> TYPE: PRT
<213> ORGANISM: Artificial Sequence
<220> FEATURE:
<223> OTHER INFORMATION: Synthetic

<400> SEQUENCE: 143

Leu Pro His His His His Leu His Thr Lys Leu Pro
1               5                   10

<210> SEQ ID NO 144
<211> LENGTH: 12
<212> TYPE: PRT
<213> ORGANISM: Artificial Sequence
<220> FEATURE:
<223> OTHER INFORMATION: Synthetic

<400> SEQUENCE: 144

Ala Pro His His His His Pro His His Leu Ser Arg
1               5                   10

<210> SEQ ID NO 145
<211> LENGTH: 12
<212> TYPE: PRT
<213> ORGANISM: Artificial Sequence
<220> FEATURE:
<223> OTHER INFORMATION: Synthetic
```

<400> SEQUENCE: 145

Arg Gly Arg Arg Arg Arg Leu Ser Cys Arg Leu Leu
1               5                   10

<210> SEQ ID NO 146
<211> LENGTH: 20
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (10)..(10)
<223> OTHER INFORMATION: D-Proline

<400> SEQUENCE: 146

Val Lys Val Lys Val Lys Val Lys Val Xaa Pro Thr Lys Val Lys Val
1               5                   10                  15

Lys Val Lys Val
            20

<210> SEQ ID NO 147
<211> LENGTH: 20
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (10)..(10)
<223> OTHER INFORMATION: D-Proline

<400> SEQUENCE: 147

Val Lys Val Lys Val Lys Val Lys Val Xaa Pro Thr Lys Val Glu Val
1               5                   10                  15

Lys Val Lys Val
            20

<210> SEQ ID NO 148
<211> LENGTH: 28
<212> TYPE: PRT
<213> ORGANISM: Artificial Sequence
<220> FEATURE:
<223> OTHER INFORMATION: Synthetic

<400> SEQUENCE: 148

Lys Ile Ala Ala Leu Lys Gln Lys Ile Ala Ser Leu Lys Gln Glu Ile
1               5                   10                  15

Asp Ala Leu Glu Tyr Glu Asn Asp Ala Leu Glu Gln
            20                  25

<210> SEQ ID NO 149
<211> LENGTH: 28
<212> TYPE: PRT
<213> ORGANISM: Artificial Sequence
<220> FEATURE:
<223> OTHER INFORMATION: Synthetic

<400> SEQUENCE: 149

Lys Ile Arg Arg Leu Lys Gln Lys Asn Ala Arg Leu Lys Gln Glu Ile
1               5                   10                  15

Ala Ala Leu Glu Tyr Glu Ile Ala Ala Leu Glu Gln
            20                  25

```
-continued

<210> SEQ ID NO 150
<211> LENGTH: 8
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: N-Palmatoyl-Alanine

<400> SEQUENCE: 150

Xaa Ala Ala Ala Lys Lys Lys Lys
1               5

<210> SEQ ID NO 151
<211> LENGTH: 8
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: N-Palmatoyl-Alanine

<400> SEQUENCE: 151

Xaa Ala Ala Ala His His His His
1               5

<210> SEQ ID NO 152
<211> LENGTH: 4
<212> TYPE: PRT
<213> ORGANISM: Artificial Sequence
<220> FEATURE:
<223> OTHER INFORMATION: Synthetic

<400> SEQUENCE: 152

Ile Ile Ile Lys
1

<210> SEQ ID NO 153
<211> LENGTH: 33
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: N-Acetyl-Methionine
<220> FEATURE:
<221> NAME/KEY: MISC_FEATURE
<222> LOCATION: (33)..(33)
<223> OTHER INFORMATION: Leucine Amide

<400> SEQUENCE: 153

Xaa Lys Gln Leu Ala His Ser Val Ser Arg Leu Glu His Ala Ser Ser
1               5                   10                  15

Lys Lys Ser Gly Ser Tyr Gly Gly Ser Lys Gly Ser Lys Arg Arg Ile
            20                  25                  30

Xaa

<210> SEQ ID NO 154
<211> LENGTH: 30
<212> TYPE: PRT
<213> ORGANISM: Artificial Sequence
<220> FEATURE:
<223> OTHER INFORMATION: Synthetic
```

```
<220> FEATURE:
<221> NAME/KEY: MISC_FEATURE
<222> LOCATION: (1)..(1)
<223> OTHER INFORMATION: N-Acetyl-Methionine
<220> FEATURE:
<221> NAME/KEY: MISC_FEATURE
<222> LOCATION: (30)..(30)
<223> OTHER INFORMATION: Tyrosine Amide

<400> SEQUENCE: 154

Xaa Lys Gln Leu Ala His Ser Val Ser Arg Leu Glu His Ala Arg Lys
1               5                   10                  15

Lys Arg Lys Lys Arg Lys Lys Arg Lys Lys Gly Gly Gly Xaa
            20                  25                  30

<210> SEQ ID NO 155
<211> LENGTH: 116
<212> TYPE: PRT
<213> ORGANISM: Artificial Sequence
<220> FEATURE:
<223> OTHER INFORMATION: Synthetic

<400> SEQUENCE: 155

Met Asp Pro Ser Met Lys Gln Leu Ala Asp Ser Leu His Gln Leu Ala
1               5                   10                  15

Arg Gln Val Ser Arg Leu Glu His Ala Asp Pro Ser Met Lys Gln Leu
                20                  25                  30

Ala Asp Ser Leu His Gln Leu Ala Arg Gln Val Ser Arg Leu Glu His
            35                  40                  45

Ala Asp Pro Ser Met Lys Gln Leu Ala Asp Ser Leu His Gln Leu Ala
        50                  55                  60

Arg Gln Val Ser Arg Leu Glu His Ala Asp Pro Ser Met Lys Gln Leu
65                  70                  75                  80

Ala Asp Ser Leu His Gln Leu Ala Arg Gln Val Ser Arg Leu Glu His
                85                  90                  95

Ala Glu Pro Ser Arg Lys Lys Arg Lys Lys Arg Lys Lys Arg Lys Lys
                100                 105                 110

Gly Gly Gly Tyr
            115
```

MINERALIZING BIOSURFACTANT USED FOR NUCLEATING SILICA

This application is the U.S. national phase of International Application No. PCT/AU2014/050234 filed 16 Sep. 2014, which designated the U.S. and claims priority to AU Patent Application No. 2013903554 filed 16 Sep. 2013, the entire contents of each of which are hereby incorporated by reference.

FIELD OF THE INVENTION

The present invention relates to emulsion-templated silica micro- and nano-capsules and methods for making them. In particular, the template emulsion is stabilized by a biosurfactant that also assists in nucleating the silica shell. Mineralizing biosurfactants and stabilized micro- and nano-emulsions useful in forming the emulsion-templated micro- and nano-capsules, and methods for the use of the silica micro- and nano-capsules are also described.

BACKGROUND OF THE INVENTION

The fabrication of silica nanocapsules has attracted much research and industrial interest owing to their unique morphology and diverse applications (Lou, 2008; Guerrero-Martínez, 2010; Schärtl, 2010). The core-shell structure allows encapsulation of fluorescent materials (Burns 2006), magnetic nanoparticles (Lu, 2007) and drugs (Barbé, 2004) in the core domain for imaging, sensing, and drug delivery, with a higher loading capacity than an equivalent solid nanoparticle. The silica shell is engineered around the core to provide: (i) a protective envelope with chemical and mechanical stability for storage and delivery; (ii) accessible pathways for adsorption, separation, and sustained release; and (iii) ease of surface modification with optical, magnetic, and/or biological functionalities enhancing the performance of nanocapsules for applications including biolabeling, controlled release, and targeted delivery.

Hard- and soft-templating approaches are commonly employed to construct silica nanocapsules. Hard templating of polystyrene latex spheres, for example, has been performed utilizing layer-by-layer assembly (Caruso, 1998), sodium silicate water-glass methodology (Cornelissen, 2003) and the Stöber synthesis (Kong, 2010). As an alternative to hard particle cores, soft emulsion droplets offer a number of advantages. Harsh processes (e.g., thermal decomposition and chemical dissolution) necessary for complete removal of the solid core are avoided and loading of a cargo is simplified as it can be solubilized in the core prior to shell formation (Hayashi, 2011; Chen, 2008; Li, 2010). Sol-gel routes, including self-templating of an organosilica precursor (Hayashi, 2011) and interfacial polycondensation of hydrolyzed silicon alkoxide on ionic (Chen, 2008; Zhao, 2009; Li, 2010; Kuwahara, 2012) and non-ionic surfactants (Underhill, 2002; Jovanovic, 2005) have been developed to synthesize silica shells on oil-in-water (O/W) emulsions in the nanometer range. However, these soft-templating approaches variously incorporate steps generating adverse effects on the environment and biologically functional cargoes, for example, the use of extreme pHs and/or elevated temperatures or pressures, and involving chemical surfactants and oils that have limited pharmaceutical compatibility. An alternative pathway to silica microcapsules and nanocapsules using more benign reaction conditions and biocompatible components would, for some applications, remove restrictions inherent in current approaches.

Biomimetic templating offers mild processes (i.e., at near-neutral pH and ambient conditions) for the synthesis of silica-based materials as revealed by silica mineralization in organisms (Morse, 1999). However, there are no current biomimetic routes to emulsion-templated silica micro- and nano-capsules. A key limitation seems to be the identification of biocompatible agents (e.g., biomolecules) that can both stabilize an emulsion template and catalyze a silicification reaction.

There is a need for a simple, less harsh method of making silica micro- and nano-capsules that can be used in delivery of drugs, proteins, nanoparticles, pesticides, herbicides, and fluorescent or spin-responsive molecules for therapeutic, diagnostic, agricultural and environmental applications.

SUMMARY OF THE INVENTION

The present invention is predicated in part on the discovery of biosurfactants that stabilize nanoemulsions can be used to nucleate silica on the stabilized nanoemulsion thereby forming silica nanocapsules.

In a first aspect of the invention there is provided a mineralizing biosurfactant comprising:
  i) a surface-active polypeptide module at least 6 amino acid residues in length; and
  ii) a charged peptide module 5 to 40 amino acid residues in length comprising at least one hydrogen bond donating amino acid residue and at least one positively charged amino acid residue;
wherein the surface-active polypeptide module and the charged peptide module are conjugated to one another.

In another aspect of the invention there is provided a stabilized microemulsion or nanoemulsion comprising an oil phase, an aqueous phase and a mineralizing biosurfactant of the invention, wherein the mineralizing biosurfactant is located at the interface between the oil and aqueous phases.

In a further aspect of the present invention, there is provided a silica micro- or nano-capsule comprising:
  i) an oil core stabilized by a surface film of mineralizing biosurfactant of the invention; and
  ii) a silica shell encapsulating the stabilized oil core.

In another aspect of the invention there is provided a method of making a silica micro- or nano-capsule comprising the steps of:
  i) forming a stabilized microemulsion or nanoemulsion by mixing a composition comprising:
    a) an oil phase;
    b) an aqueous phase; and
    c) a mineralizing biosurfactant of the invention; and
  ii) mixing the microemulsion or nanoemulsion with silica or a silica precursor.

In a yet further aspect of the invention there is provided a composition comprising the micro- or nano-capsules of the invention and a carrier.

In another aspect of the invention there is provided a use of the micro- or nano-capsules of the invention to deliver a compound to a human, animal, pest or environment.

Figure 1:
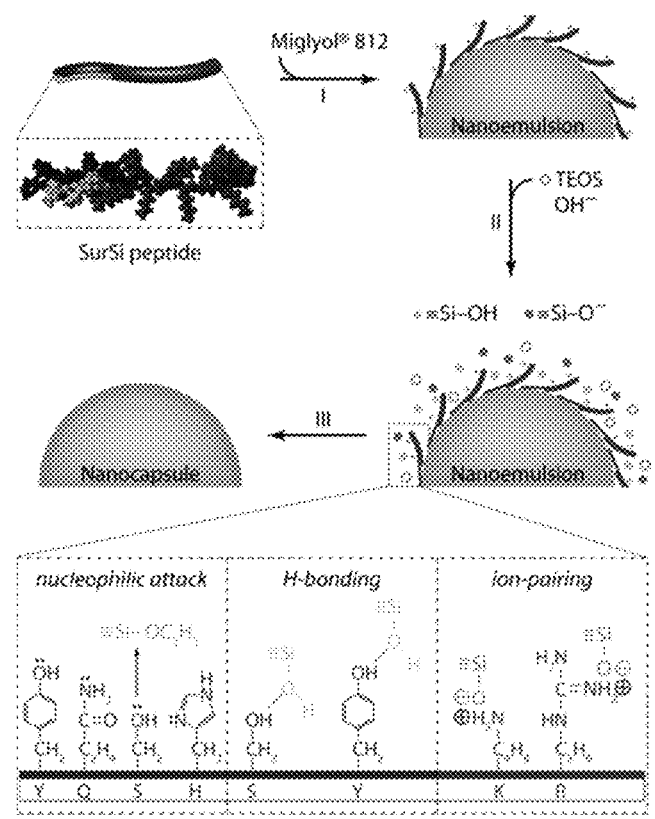
FIG. 1 is a schematic diagram showing the strategy for preparation of the emulsion-templated silica nanocapsules comprising a mineralizing biosurfactant. The mineralizing biosurfactant is comprised of a surface-active polypeptide module (Sur) and a charged peptide module (Si). Step (I) sonication of Miglyol® 812 oil in a SurSi solution followed by dialysis; Step (II) addition of tetraethoxysilane (TEOS) to nanoemulsion (bottom panel showing possible molecular interactions between peptide side chain groups and silica species); Step (III) interfacial polycondensation of silica species.

Amino acid structure and single and three letter abbreviations used throughout the specification are defined in Table 1, which lists the twenty naturally occurring amino acids which occur in proteins as L-isomers.

TABLE 1

(1)

H R
 \\ /
  C
 / \\
H$_2$N   O$_2$H (2)

[pyrrolidine-2-carboxylic acid structure]

| Amino Acid | Three-letter Abbreviation | One-letter symbol | Structure of side chain (R) |
|---|---|---|---|
| Alanine | Ala | A | —CH$_3$ |
| Arginine | Arg | R | —(CH$_2$)$_3$NHC(=N)NH$_2$ |
| Asparagine | Asn | N | —CH$_2$CONH$_2$ |
| Aspartic acid | Asp | D | —CH$_2$CO$_2$H |
| Cysteine | Cys | C | —CH$_2$SH |
| Glutamine | Gln | Q | —(CH$_2$)$_2$CONH$_2$ |
| Glutamic acid | Glu | E | —(CH$_2$)$_2$CO$_2$H |
| Glycine | Gly | G | —H |
| Histidine | His | H | —CH$_2$(4-imidazolyl) |
| Isoleucine | Ile | I | —CH(CH$_3$)CH$_2$CH$_3$ |
| Leucine | Leu | L | —CH$_2$CH(CH$_3$)$_2$ |
| Lysine | Lys | K | —(CH$_2$)$_4$NH$_2$ |
| Methionine | Met | M | —(CH$_2$)$_2$SCH$_3$ |
| Phenylalanine | Phe | F | —CH$_2$Ph |
| Proline | Pro | P | see formula (2) above for structure of amino acid |
| Serine | Ser | S | —CH$_2$OH |
| Threonine | Thr | T | —CH(CH$_3$)OH |
| Tryptophan | Trp | W | —CH$_2$(3-indolyl) |
| Tyrosine | Tyr | Y | —CH$_2$(4-hydroxyphenyl) |
| Valine | Val | V | —CH(CH$_3$)$_2$ |

The term "α-amino acid" as used herein, refers to a compound having an amino group and a carboxyl group in which the amino group and the carboxyl group are separated by a single carbon atom, the α-carbon atom. An α-amino acid includes naturally occurring and non-naturally occurring L-amino acids and their D-isomers and derivatives thereof such as salts or derivatives where functional groups are protected by suitable protecting groups. The α-amino acid may also be further substituted in the α-position with a group selected from —C$_1$-C$_6$alkyl, —(CH$_2$)$_n$COR$_1$, —(CH$_2$)$_n$R$_2$, —PO$_3$H, —(CH$_2$)$_n$heterocyclyl or —(CH$_2$)$_n$aryl where R$_1$ is —OH, —NH$_2$, —NHC$_1$—C$_3$alkyl, —OC$_1$—C$_3$alkyl or —C$_1$-C$_3$alkyl and R$_2$ is —OH, —SH, —SC$_1$-C$_3$alkyl, —OC$_1$—C$_3$alkyl, —C$_3$-C$_{12}$cycloalkyl, —NH$_2$, —NHC$_1$—C$_3$alkyl or —NHC(C=NH)NH$_2$ and where each alkyl, cycloalkyl, aryl or heterocyclyl group may be substituted with one or more groups selected from —OH, —NH$_2$, —NHC$_1$—C$_3$alkyl, —OC$_1$—C$_3$alkyl, —SH, —SC$_1$—C$_3$alkyl, —CO$_2$H, —CO$_2$C$_1$—C$_3$alkyl, —CONH$_2$ or —CONHC$_1$—C$_3$alkyl.

As used herein, the term "β-amino acid" refers to an amino acid that differs from an α-amino acid in that there are two (2) carbon atoms separating the carboxyl terminus and the amino terminus. As such, β-amino acids with a specific side chain can exist as the R or S enantiomers at either of the α (C2) carbon or the β (C3) carbon, resulting in a total of 4 possible isomers for any given side chain. The side chains may be the same as those of naturally occurring α-amino acids (see Table 1 above) or may be the side chains of non-naturally occurring amino acids (see Table 2 below).

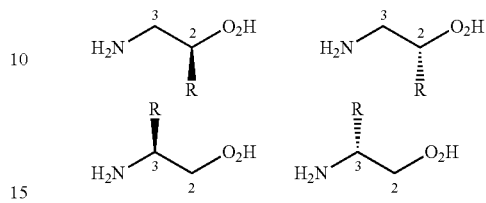

Furthermore, the β-amino acids may have mono-, di-, tri- or tetra-substitution at the C2 and C3 carbon atoms. Mono-substitution may be at the C2 or C3 carbon atom. Di-substitution includes two substituents at the C2 carbon atom, two substituents at the C3 carbon atom or one substituent at each of the C2 and C3 carbon atoms. Tri-substitution includes two substituents at the C2 carbon atom and one substituent at the C3 carbon atom or two substituents at the C3 carbon atom and one substituent at the C2 carbon atom. Tetra-substitution provides for two substituents at the C2 carbon atom and two substituents at the C3 carbon atom. Suitable substituents include —C$_1$-C$_6$alkyl, —(CH$_2$)$_n$COR$_1$, —(CH$_2$)—R$_2$, —PO$_3$H, —(CH$_2$)$_n$heterocyclyl or —(CH$_2$)$_n$aryl where R$_1$ is —OH, —NH$_2$, —NHC$_1$—C$_3$alkyl, —OC$_1$—C$_3$alkyl or —C$_1$-C$_3$alkyl and R$_2$ is —OH, —SH, —SC$_1$-C$_3$alkyl, —OC$_1$—C$_3$alkyl, —C$_3$-C$_{12}$cycloalkyl, —NH$_2$, —NHC$_1$—C$_3$alkyl or —NHC(C=NH)NH$_2$ and where each alkyl, cycloalkyl, aryl or heterocyclyl group may be substituted with one or more groups selected from —OH, —NH$_2$, —NHC$_1$—C$_3$alkyl, —OC$_1$—C$_3$alkyl, —SH, —SC$_1$—C$_3$alkyl, —CO$_2$H, —CO$_2$C$_1$—C$_3$alkyl, —CONH$_2$ or —CONHC$_1$—C$_3$alkyl.

Other suitable β-amino acids include conformationally constrained β-amino acids. Cyclic β-amino acids are conformationally constrained and are generally not accessible to enzymatic degradation. Suitable cyclic β-amino acids include, but are not limited to, cis- and trans-2-aminocyclopropyl carboxylic acids, 2-aminocyclobutyl and cyclobutenyl carboxylic acids, 2-aminocyclopentyl and cyclopentenyl carboxylic acids, 2-aminocyclohexyl and cyclohexenyl carboxylic acids and 2-amino-norbornane carboxylic acids and their derivatives, some of which are shown below:

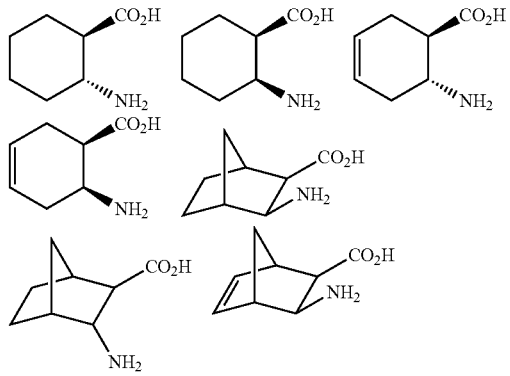

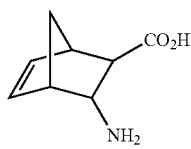

Suitable derivatives of β-amino acids include salts and may have functional groups protected by suitable protecting groups.

The term "non-naturally occurring amino acid" as used herein, refers to amino acids having a side chain that does not occur in the naturally occurring L-α-amino acids. Examples of non-natural amino acids and derivatives include, but are not limited to, use of norleucine, 4-amino butyric acid, 4-amino-3-hydroxy-5-phenylpentanoic acid, 6-aminohexanoic acid, t-butylglycine, norvaline, phenylglycine, ornithine, citrulline, sarcosine, 4-amino-3-hydroxy-6-methylheptanoic acid, 2-thienyl alanine and/or D-isomers of amino acids. A list of unnatural amino acids that may be useful herein is shown in Table 2.

TABLE 2

| Non-conventional amino acid | Code |
|---|---|
| α-aminobutyric acid | Abu |
| α-amino-α-methylbutyrate | Mgabu |
| aminocyclopropane-carboxylate | Cpro |
| aminoisobutyric acid | Aib |
| aminonorbornyl-carboxylate | Norb |
| cyclohexylalanine | Chexa |
| cyclopentylalanine | Cpen |
| D-alanine | Dal |
| D-arginine | Darg |
| D-aspartic acid | Dasp |
| D-cysteine | Dcys |
| D-glutamine | Dgln |
| D-glutamic acid | Dglu |
| D-histidine | Dhis |
| D-isoleucine | Dile |
| D-leucine | Dleu |
| D-lysine | Dlys |
| D-methionine | Dmet |
| D-ornithine | Dorn |
| D-phenylalanine | Dphe |
| D-proline | Dpro |
| D-serine | Dser |
| D-threonine | Dthr |
| D-tryptophan | Dtrp |
| D-tyrosine | Dtyr |
| D-valine | Dval |
| D-α-methylalanine | Dmala |
| D-α-methylarginine | Dmarg |
| D-α-methylasparagine | Dmasn |
| D-α-methylaspartate | Dmasp |
| D-α-methylcysteine | Dmcys |
| D-α-methylglutamine | Dmgln |
| D-α-methylhistidine | Dmhis |
| D-α-methylisoleucine | Dmile |
| D-α-methylleucine | Dmleu |
| D-α-methyllysine | Dmlys |
| D-α-methylmethionine | Dmmet |
| D-α-methylornithine | Dmorn |
| D-α-methylphenylalanine | Dmphe |
| D-α-methylproline | Dmpro |
| D-α-methylserine | Dmser |
| D-α-methylthreonine | Dmthr |
| D-α-methyltryptophan | Dmtrp |
| D-α-methyltyrosine | Dmty |
| D-α-methylvaline | Dmval |
| D-N-methylalanine | Dnmala |
| D-N-methylarginine | Dnmarg |
| D-N-methylasparagine | Dnmasn |
| D-N-methylaspartate | Dnmasp |
| D-N-methylcysteine | Dnmcys |
| D-N-methylglutamine | Dnmgln |
| D-N-methylglutamate | Dnmglu |
| D-N-methylhistidine | Dnmhis |
| D-N-methylisoleucine | Dnmile |
| D-N-methylleucine | Dnmleu |
| D-N-methyllysine | Dnmlys |
| N-methylcyclohexylalanine | Nmchexa |
| D-N-methylornithine | Dnmorn |
| N-methylglycine | Nala |
| N-methylaminoisobutyrate | Nmaib |
| N-(1-methylpropyl)glycine | Nile |
| N-(2-methylpropyl)glycine | Nleu |
| D-N-methyltryptophan | Dnmtrp |
| D-N-methyltyrosine | Dnmtyr |
| D-N-methylvaline | Dnmval |
| γ-aminobutyric acid | Gabu |
| L-t-butylglycine | Tbug |
| L-ethylglycine | Etg |
| L-homophenylalanine | Hphe |
| L-α-methylarginine | Marg |
| L-α-methylaspartate | Masp |
| L-α-methylcysteine | Mcys |
| L-α-methylglutamine | Mgln |
| L-α-methylhistidine | Mhis |
| L-α-methylisoleucine | Mile |
| L-α-methylleucine | Mleu |
| L-α-methylmethionine | Mmet |
| L-α-methylnorvaline | Mnva |
| L-α-methylphenylalanine | Mphe |
| L-α-methylserine | Mser |
| L-α-methyltryptophan | Mtrp |
| L-α-methylvaline | Mval |
| N-(N-(2,2-diphenylethyl) carbamylmethyl)glycine | Nnbhm |
| 1-carboxy-1-(2,2-diphenyl-ethylamino)cyclopropane | Nmbc |
| L-N-methylalanine | Nmala |
| L-N-methylarginine | Nmarg |
| L-N-methylasparagine | Nmasn |
| L-N-methylaspartic acid | Nmasp |
| L-N-methylcysteine | Nmcys |
| L-N-methylglutamine | Nmgln |
| L-N-methylglutamic acid | Nmglu |
| L-N-methylhistidine | Nmhis |
| L-N-methylisoleucine | Nmile |
| L-N-methylleucine | Nmleu |
| L-N-methyllysine | Nmlys |
| L-N-methylmethionine | Nmmet |
| L-N-methylnorleucine | Nmnle |
| L-N-methylnorvaline | Nmnva |
| L-N-methylornithine | Nmorn |
| L-N-methylphenylalanine | Nmphe |
| L-N-methylproline | Nmpro |
| L-N-methylserine | Nmser |
| L-N-methylthreonine | Nmthr |
| L-N-methyltryptophan | Nmtrp |
| L-N-methyltyrosine | Nmtyr |
| L-N-methylvaline | Nmval |
| L-N-methylethylglycine | Nmetg |
| L-N-methyl-t-butylglycine | Nmtbug |
| L-norleucine | Nle |
| L-norvaline | Nva |
| α-methyl-aminoisobutyrate | Maib |
| α-methyl-aminobutyrate | Mgabu |
| α-methylcyclohexylalanine | Mchexa |
| α-methylcyclopentylalanine | Mcpen |
| α-methyl-α-napthylalanine | Manap |
| α-methylpenicillamine | Mpen |
| N-(4-aminobutyl)glycine | Nglu |
| N-(2-aminoethyl)glycine | Naeg |
| N-(3-aminopropyl)glycine | Norn |
| N-amino-α-methylbutyrate | Nmaabu |
| α-napthylalanine | Anap |
| N-benzylglycine | Nphe |
| N-(2-carbamylethyl)glycine | Ngln |
| N-(carbamylmethyl)glycine | Nasn |
| N-(2-carboxyethyl)glycine | Nglu |

TABLE 2-continued

| Non-conventional amino acid | Code |
| --- | --- |
| N-(carboxymethyl)glycine | Nasp |
| N-cyclobutylglycine | Ncbut |
| N-cycloheptylglycine | Nchep |
| N-cyclohexylglycine | Nchex |
| N-cyclodecylglycine | Ncdec |
| N-cyclododecylglycine | Ncdod |
| N-cyclooctylglycine | Ncoct |
| N-cyclopropylglycine | Ncpro |
| N-cycloundecylglycine | Ncund |
| N-(2,2-diphenylethyl)glycine | Nbhm |
| N-(3,3-diphenylpropyl)glycine | Nbhe |
| N-(3-guanidinopropyl)glycine | Narg |
| N-(1-hydroxyethyl)glycine | Nthr |
| N-(hydroxyethyl))glycine | Nser |
| N-(imidazolylethyl))glycine | Nhis |
| N-(3-indolylethyl)glycine | Nhtrp |
| N-methyl-γ-aminobutyrate | Nmgabu |
| D-N-methylmethionine | Dnmmet |
| N-methylcyclopentylalanine | Nmcpen |
| D-N-methylphenylalanine | Dnmphe |
| D-N-methylproline | Dnmpro |
| D-N-methylserine | Dnmser |
| D-N-methylthreonine | Dnmthr |
| N-(1-methylethyl)glycine | Nval |
| N-methylnapthylalanine | Nmanap |
| N-methylpenicillamine | Nmpen |
| N-(p-hydroxyphenyl)glycine | Nhtyr |
| N-(thiomethyl)glycine | Ncys |
| penicillamine | Pen |
| L-α-methylalanine | Mala |
| L-α-methylasparagine | Masn |
| L-α-methyl-t-butylglycine | Mtbug |
| L-methylethylglycine | Metg |
| L-α-methylglutamate | Mglu |
| L-α-methylhomophenylalanine | Mhphe |
| N-(2-methylthioethyl)glycine | Nmet |
| L-α-methyllysine | Mlys |
| L-α-methylnorleucine | Mnle |
| L-α-methylornithine | Morn |
| L-α-methylproline | Mpro |
| L-α-methylthreonine | Mthr |
| L-α-methyltyrosine | Mtyr |
| L-N-methylhomophenylalanine | Nmhphe |
| N-(N-(3,3-diphenylpropyl) carbamylmethyl)glycine | Nnbhe |

The term "alkyl" as used herein refers to straight chain or branched hydrocarbon groups. Suitable alkyl groups include, but are not limited to methyl, ethyl, propyl, isopropyl, butyl, isobutyl, pentyl, hexyl, heptyl, octyl, nonyl, decyl, dodecyl, tetradecyl, hexadecyl and octadecyl. The term alkyl may be prefixed by a specified number of carbon atoms to indicate the number of carbon atoms or a range of numbers of carbon atoms that may be present in the alkyl group. For example, $C_1$-$C_3$ alkyl refers to methyl, ethyl, propyl and isopropyl.

The term "cycloalkyl" as used herein, refers to cyclic hydrocarbon groups. Suitable cycloalkyl groups include, but are not limited to, cyclopropyl, cyclobutyl, cyclopentyl, cyclohexyl, cycloheptyl, cyclooctyl, cyclononyl, cyclodecyl, cycloundecyl and cyclododecyl.

The term "heterocyclyl" as used herein refers to 5 or 6 membered saturated, partially unsaturated or aromatic cyclic hydrocarbon groups in which at least one carbon atom has been replaced by N, O or S. Optionally, the heterocyclyl group may be fused to a phenyl ring. Suitable heterocyclyl groups include, but are not limited to pyrrolidinyl, piperidinyl, pyrrolyl, thiophenyl, furanyl, oxazolyl, imidazolyl, thiazolyl, isoxazolyl, pyrazolyl, isothiazolyl, pyridinyl, quinolinyl, isoquinolinyl, indolyl, benzofuranyl, benzothiophenyl, oxadiazolyl, tetrazolyl, triazolyl and pyrimidinyl.

The term "aryl" as used herein, refers to $C_6$-$C_{10}$ aromatic hydrocarbon groups, for example phenyl and naphthyl.

The term "α-helix breaking amino acid residue" refers to an amino acid residue that has a low frequency of occurrence in known α-helical conformations and which promotes termination of an α-helix. α-Helix breaking amino acid residues may lack an amide hydrogen to participate in hydrogen bonding within the helix or may be too conformationally flexible or inflexible to form the constrained α-helical conformation in an energy efficient manner Examples of α-helix breaking amino acid residues include, but are not limited to proline and glycine.

The term "hydrophilic amino acid residue" as used herein refers to an amino acid residue in which the side chain is polar or charged. Examples include glycine, L-serine, L-threonine, L-cysteine, L-tyrosine, L-asparagine, L-glutamine, L-aspartic acid, L-glutamic acid, L-lysine, L-arginine, L-histidine, L-ornithine, D-serine, D-threonine, D-cysteine, D-tyrosine, D-asparagine, D-glutamine, D-aspartic acid, D-glutamic acid, D-lysine, D-arginine, D-histidine and D-ornithine, especially L-serine, L-threonine, L-cysteine, L-tyrosine, L-asparagine, L-glutamine, L-aspartic acid, L-glutamic acid, L-lysine, L-arginine, L-histidine and L-ornithine.

As used herein, the term "hydrophobic amino acid residue" refers to an amino acid residue in which the side chain is non-polar. Examples include, but are not limited to L-alanine, L-valine, L-leucine, L-isoleucine, L-proline, L-methionine, L-phenylalanine, L-tryptophan, L-aminoisobutyric acid, D-alanine, D-valine, D-leucine, D-isoleucine, D-proline, D-methionine, D-phenylalanine, D-tryptophan, D-aminoisobutyric acid, L-cyclohexylalanine, D-cyclohexylalanine, D-cyclopentylalanine, D-cyclopentylalanine, L-norleucine, D-norleucine, L-norvaline, D-norvaline, L-tert-butylglycine, D-tert-butylglycine, L-ethylglycine and D-ethylglycine, especially D-alanine, L-valine, L-leucine, L-isoleucine, L-proline, L-methionine, L-phenylalanine, L-tryptophan and L-aminoisobutyric acid.

As used herein, the term "positively charged amino acid residue" refers to an amino acid residue having a side chain capable of bearing a positive charge. Examples include, but are not limited to D-lysine, L-arginine, L-histidine, L-ornithine, D-lysine, D-arginine, D-histidine and D-ornithine.

As used herein, the term "negatively charged amino acid residue" refers to an amino acid residue having a side chain capable of bearing a negative charge. Examples include, but are not limited to D-aspartic acid, L-glutamic acid, D-aspartic acid and D-glutamic acid.

As used herein, the term "polar amino acid residue" refers to an amino acid residue having a side chain that has a dipole moment. Examples of polar amino acid residues, include, but are not limited to glycine, L-serine, L-threonine, L-cysteine, L-tyrosine, L-asparagine, L-glutamine, D-serine, D-threonine, D-cysteine, D-tyrosine, D-asparagine and D-glutamine The term "amino acid having a small side chain" refers to amino acid residues having a side chain with 4 or less non-hydrogen atoms, especially 3 or less non-hydrogen atoms. Examples include, but are not limited to, glycine, L-alanine, L-valine, L-leucine, L-isoleucine, L-methionine, L-serine, D-threonine, L-cysteine, L-asparagine, L-aspartic acid, D-alanine, D-valine, D-leucine, D-isoleucine, D-methionine, D-serine, D-threonine, D-cysteine, D-asparagine and D-aspartic acid, especially glycine, L-alanine, L-valine, L-serine, L-threonine and L-cysteine.

The term "conservative amino acid substitution" refers to substituting one amino acid in a sequence with another amino acid that has similar properties of size, polarity and/or aromaticity and does not change the nature of activity of the peptide. For example, one polar amino acid residue may be substituted with another polar amino acid residue or an amino acid residue having a small side chain may be substituted with another amino acid residue having a small side chain.

The term "liquid-liquid interface" refers to the region forming the common boundary between the immiscible liquids, the oil phase and polar phase, in the nanoemulsion.

The terms "self-assemble", "self-assembled" and "self-assembly" refer to a population of peptide biosurfactant molecules with an affinity for the liquid-liquid interface and which relocate themselves from the bulk solution to the liquid-liquid interface.

The term "surface-active polypeptide" refers to a polypeptide that has both hydrophilic and hydrophobic residues and that has an affinity for the liquid-liquid interface and therefore is capable of self-assembly at the liquid-liquid interface either with or without structural modification in such a way that the hydrophobic and hydrophilic residues are able to preferentially partition into their miscible phases at the liquid-liquid interface.

As used herein, the term "microemulsion" refers to an oil-in-water emulsion having an average oil phase particle size of 900 nm to 100 μm especially between 900 nm and 50 μm, more especially between 900 nm and 5 μm.

As used herein, the term "silica microcapsule" refers to a structure comprising a core-shell structure having an oil core and a silica shell. The microcapsules have an average diameter of less than 150 μm, especially between 1 μm and 100 μm, more especially 1 μm and 30 μm, and most especially between 1 μm and 5 μm.

The term "nanoemulsion" refers to an oil-in-water emulsion having an average oil phase particle size of less than 900 nm, especially between 20 nm and 500 nm, more especially between 30 nm and 300 nm.

The term "silica nanocapsule" refers to a structure comprising core-shell structure having an oil core and a silica shell. The nanocapsules having an average diameter of less than 1 μm, especially between 50 nm and 750 nm, more especially between 70 nm and 500 nm, more especially between 80 nm and 400 nm.

2. Mineralizing Biosurfactants

In one aspect of the invention, there is provided a mineralizing biosurfactant comprising:
i) a surface-active polypeptide module at least 6 amino acid residues in length; and
ii) a charged peptide module 5 to 40 amino acid residues in length comprising at least one hydrogen bond donating amino acid residue and at least one positively charged amino acid residue;
wherein the surface-active polypeptide module and the charged peptide module are conjugated to one another.

The surface-active polypeptide module may be any peptide or protein that has a hydrophobic region and a hydrophilic region and is capable of self-assembly at a liquid-liquid interface, such as the interface between an oil phase and a polar or aqueous phase.

In some embodiments, the surface-active polypeptide module is a polypeptide or protein that has tertiary structure presenting defined hydrophobic and hydrophilic regions either before or after adsorption at the liquid-liquid interface. Typical proteins include food biosurfactants or portions thereof such as casein and lactoglobulin and the common protein lysozyme, all of which are known in the art to be surface active.

In embodiments where the surface-active polypeptide module is a peptide or polypeptide rather than a protein, the polypeptide module may have a limitation on the maximum number of amino acid residues in the module. For example, the surface-active polypeptide module may be 6 to 130 amino acid residues in length.

In some embodiments, the surface-active polypeptide is a co-block polypeptide having a sequence comprising blocks of hydrophilic amino acid residues and blocks of hydrophobic amino acid residues, for example a sequence:

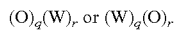

$(O)_q(W)_r$ or $(W)_q(O)_r$ where O is a hydrophobic amino acid residue and W is a hydrophilic amino acid residue, q and r are at least each independently 1 and q+r is an integer of 6 to 130.

In some embodiments, the surface-active polypeptide module comprises a peptide able to structure in such a way as to form a hydrophobic face and a hydrophilic face thus imparting preferential absorption at a liquid-liquid interface. In some embodiments, the surface-active polypeptide module comprises an amphiphilic peptide.

In these embodiments, the surface-active polypeptide module comprises an amphiphilic peptide comprising an amino acid sequence:

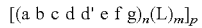

$[(a\ b\ c\ d\ d'\ e\ f\ g)_n(L)_m]_p$ wherein n is an integer from 2 to 12;
amino acid residues a and d are hydrophobic amino acid resides;
amino acid d' is absent or is any amino acid residue;
at least one of residues b and c and at least one of residues e and f are hydrophilic amino acid residues and the other of amino acid resides b and c and e and f are any amino acid residue;
amino acid residue g is any amino acid residue;
L is a linking peptide sequence of 1 to 11 amino acid residues;
m is 0 or 1; and
p is an integer from 1 to 6.

In some embodiments, n is 2 to 8 or 2 to 6, especially 2 to 4.

Amino acid residues a and d are hydrophobic amino acid residues. In some embodiments, amino acid residues a and d are independently selected from L-alanine, L-valine, L-leucine, L-methionine, D-isoleucine, L-phenylalanine, L-tyrosine, D-alanine, D-valine, D-leucine, D-methionine, D-isoleucine, D-phenylalanine and D-tyrosine, especially L-alanine, L-methionine, L-valine and L-leucine.

Amino acid residue d' may be absent or may be any amino acid residue. In some embodiments, when present, d' is a hydrophobic amino acid residue. The residue d' may be included in longer sequences, for example, where n is 3, 6, 9 or 12, to counteract perturbations in helix turn when a helix is formed, that may result in misalignment of the hydrophobic residues on one face of the helix. In some embodiments, d' is present in the third, sixth, ninth and/or twelfth sequence of $(a\ b\ c\ d\ d'\ e\ f\ g)_n$ when n is 3, 6, 9 and 12, but is absent in the other (a b c d d' e f g) sequences in the amphiphilic peptide module. In some embodiments, when present, amino acid d' may be selected from L-alanine, L-valine, L-leucine, L-methionine, L-isoleucine, L-phenylalanine, L-tyrosine, D-alanine, D-valine, D-leucine, D-methionine, D-isoleucine, D-phenylalanine, D-tyrosine, especially D-alanine, L-methionine, L-valine and L-leucine.

At least one of b and c is a hydrophilic amino acid residue, such as L-serine, L-threonine, L-cysteine, L-tyrosine, L-asparagine, L-glutamine, L-aspartic acid, L-glutamic acid, L-lysine, L-histidine, L-ornithine, D-serine, D-threonine, D-cysteine, D-tyrosine, D-asparagine, D-glutamine, D-aspartic acid, D-glutamic acid, D-lysine, D-histidine and D-ornithine, especially L-serine, L-threonine, L-cysteine, L-tyrosine, L-asparagine, L-glutamine, L-aspartic acid, L-glutamic acid, L-lysine, L-histidine and L-ornithine. The other one of amino acid residues b and c is any amino acid residue, especially an amino acid residue that has a propensity to form α-helices, such as alanine, lysine, uncharged glutamic acid, methionine, leucine and aminoisobutyric acid or a small amino acid residue such as alanine, serine, valine, leucine or isoleucine, or a hydrophilic amino acid residue such as glutamine, asparagine, serine, glutamic acid and aspartic acid.

At least one of e and f is a hydrophilic amino acid residue, such as L-serine, L-threonine, D-cysteine, L-tyrosine, L-asparagine, L-glutamine, L-aspartic acid, L-glutamic acid, L-lysine, L-histidine, L-ornithine, D-serine, D-threonine, D-cysteine, D-tyrosine, D-asparagine, D-glutamine, D-aspartic acid, D-glutamic acid, D-lysine, D-histidine and D-ornithine, especially L-serine, L-threonine, L-cysteine, L-tyrosine, L-asparagine, L-glutamine, L-aspartic acid, L-glutamic acid, L-lysine, L-histidine and L-ornithine. The other one of amino acid residues e and f is any amino acid residue, especially an amino acid residue that has a propensity to form α-helices, such as alanine, lysine, uncharged glutamic acid, methionine, leucine and aminoisobutyric acid or a small amino acid residue such as alanine, serine, valine, leucine or isoleucine, or a hydrophilic amino acid residue such as glutamine, asparagine, serine, glutamic acid and aspartic acid.

Amino acid residue g may be any amino acid residue. In particular embodiments, amino acid residue g is a residue that has a propensity to form α-helices, such as alanine, lysine, uncharged glutamic acid, methionine, leucine and aminoisobutyric acid, especially alanine, lysine and uncharged glutamic acid.

In some embodiments, each amino acid residue b is independently selected from a small hydrophobic amino acid residue, such as alanine, leucine, valine, methionine and isoleucine, or a hydrophilic amino acid residue, especially a polar or charged amino acid residue such as L-serine, L-threonine, L-cysteine, L-tyrosine, L-asparagine, L-glutamine, L-lysine, L-arginine, L-histidine, aspartic acid and glutamic acid. In some embodiments, each b is independently selected from D-lysine, L-histidine, L-serine, L-alanine, L-asparagine and L-glutamine In some embodiments, each amino acid residue c is independently selected from a polar, positively charged or negatively charged amino acid residue, such as L-serine, L-threonine, L-cysteine, L-tyrosine, L-asparagine, L-glutamine, L-lysine, L-arginine, L-histidine, L-aspartic acid and L-glutamic acid. In some embodiments, each c is independently selected from L-glutamine, L-arginine, L-serine, L-glutamic acid and L-asparagine.

Each amino acid residue e is independently any amino acid residue and may be hydrophobic or hydrophilic. In some embodiments, each e is independently selected from L-alanine, L-valine, L-leucine, L-isoleucine, L-serine, L-threonine, L-aspartic acid and L-glutamic acid, especially L-alanine, L-serine and L-glutamic acid.

In some embodiments, each amino acid residue f is a polar, positively charged or negatively charged amino acid residue, such as L-serine, L-threonine, L-cysteine, L-tyrosine, L-asparagine, L-glutamine, L-lysine, L-arginine, L-histidine, L-aspartic acid and L-glutamic acid. In some embodiments, each f is independently selected from L-aspartic acid, L-glutamic acid, L-arginine, L-glutamine, L-histidine, L-lysine and L-asparagine.

Amino acid residue g is independently any amino acid residue and may be hydrophobic or hydrophilic. In some embodiments, the residue g is independently selected from a small hydrophobic residue or a charged or polar uncharged residue. In some embodiments, each g is independently selected from L-alanine, L-valine, L-leucine, L-isoleucine, L-serine, L-threonine, L-asparagine L-lysine, L-glutamic acid and L-glutamine, especially L-alanine, L-serine and D-glutamine The linking peptide sequence L may be absent (m=0) or may be a sequence of any amino acid residues. In some embodiments, the linking sequence L has 1 or 2 amino acid residues. In other embodiments, the linking sequences has at least three amino acid residues. In some embodiments, the linking peptide sequence is present between peptide sequences (a b c d e f g)$_n$ and enables folding of the peptide sequences (a b c d e f g)$_n$ allowing the peptide sequences (a b c d e f g)$_n$ to interact with one another and form folded tertiary structures such as 2, 3, 4 or 5 α-helix bundles.

In some embodiments, the linking peptide sequence L has 3 to 9, 3 to 7, 3 to 5 amino acid residues. In a particular embodiment, the linking peptide sequence L has 3 amino acid residues.

In some embodiments, the peptide sequence (a b c d d' e f g)$_n$ is α-helical or has α-helical propensity. In these embodiments, the linking peptide sequence L may comprise an amino acid residue that is an α-helix breaking amino acid residue.

This residue assists in terminating any α-helical structure formed by the preceding peptide (a b c d d' e f g)$_n$ and allowing the linking amino acid residues flexibility for folding. α-Helix breaking amino acid residues include amino acid residues that are unable to contribute to α-helical structure, such as proline, or have high flexibility, for example serine. The charged group on aspartic acid is also known to have low helix propensity. Common α-helix breaking amino acid residues include proline and glycine.

The linking peptide sequence also may include one or more residues that allow flexibility so that two adjacent peptides can fold so that they interact with one another. In particular embodiments, the linking peptide sequence allows the peptides (a b c d d' e f g)$_n$ to fold in a manner to form a 2, 3, 4 or 5 helix bundle, especially a 4-helix bundle, in bulk solution. In some embodiments, the flexibility is imparted by one or more amino acid residues having a small side chain, for example, glycine, serine, alanine, valine, cysteine and threonine. In some embodiments, these same amino acids play a dual role of conferring flexibility to the overall sequence of linking amino acid residues as well as helix termination.

When more than one linking peptide sequence is present in the polypeptide, for example, where m is 1 and p is 2 to 6, each linking sequence may be the same or different.

In some embodiments, the linking sequence comprises D-P-X where X is a small amino acid residue such as serine, glycine, cysteine or threonine. In some embodiments, the linking sequence comprises D-P-S. In some embodiments, the linking sequence is D-P-S.

In some embodiments, m is 1 and p is 1 to 6, especially 2 to 6, 3 to 6 or 3 to 5.

In other embodiments, m is 0 and p is 1. In these embodiments, the surface peptide module comprises an amino acid sequence:

(a b c d d' e f g)$_n$ wherein n is an integer from 2 to 12;
amino acid residues a and d are hydrophobic amino acid residues;
amino acid residue d' is absent or is any amino acid residue;
at least one of residues b and c and at least one of residues e and f are hydrophilic amino acid residues and the other of amino acid residues b and c and e and f are any amino acid residue;
amino acid residue g is any amino acid residue.

In some embodiments, the sequence (a b c d d' e f g)$_n$ may be shifted in sequence by one amino acid residue to form the sequence (g a b c d d' e f)$_n$. Sequence (a b c d d' e f g)$_n$ and sequence (g a b c d d' e f)$_n$ are interchangeable.

In some embodiments, the surface-active peptide module is selected from:

| Sequence | |
|---|---|
| MKQLADSVSRLEHA | SEQ ID NO: 1 |
| MKQLADSVSRLESA | SEQ ID NO: 2 |
| LMQLARQVSRLESA | SEQ ID NO: 3 |
| MKELADSVDRLESA | SEQ ID NO: 4 |
| MKQLADSVSHLEHA | SEQ ID NO: 5 |
| MEELADSVEELESA | SEQ ID NO: 6 |
| MKKLADSVKKLESA | SEQ ID NO: 7 |
| EISALEKEISALEK | SEQ ID NO: 8 |
| KISALKEKISALKE | SEQ ID NO: 9 |
| MKELADSVSRLEHA | SEQ ID NO: 10 |
| AKSLAESVSRLEHA | SEQ ID NO: 11 |
| MKQLADSLHQLARQ | SEQ ID NO: 12 |
| MKQLADSLMQLARQ | SEQ ID NO: 13 |
| LMQLARQMKQLADS | SEQ ID NO: 14 |
| LMQLARQLMQLARQ | SEQ ID NO: 15 |
| MKELADSLMQLARQ | SEQ ID NO: 16 |
| MKQLADSLHQLAHQ | SEQ ID NO: 17 |
| MEELADSLEELARQ | SEQ ID NO: 18 |
| MKKLADSLKKLARQ | SEQ ID NO: 19 |
| MKQLADSLHQLAHK | SEQ ID NO: 20 |
| MKELADSLHELARE | SEQ ID NO: 21 |
| MKELADSLHQLARQ | SEQ ID NO: 22 |
| MKQLADSLHELARQ | SEQ ID NO: 23 |
| MKELADSLHELARQ | SEQ ID NO: 24 |
| MKELADSLHQLARE | SEQ ID NO: 25 |
| MKQLADSLHELARE | SEQ ID NO: 26 |
| AKSLAESLHSLARS | SEQ ID NO: 27 |
| LHQLARQVSRLEHA | SEQ ID NO: 28 |
| LHQLARQVSRLEHA | SEQ ID NO: 29 |
| LMQLARQVSRLESA | SEQ ID NO: 30 |
| LMQLARQVDRLESA | SEQ ID NO: 31 |
| LHQLAHQVSHLEHA | SEQ ID NO: 32 |
| LEELARQVEELESA | SEQ ID NO: 33 |
| LKKLARQVKKLESA | SEQ ID NO: 34 |
| LHQLAHKVSHLEHA | SEQ ID NO: 35 |
| LHELAREVSRLEHA | SEQ ID NO: 36 |
| LHQLARQVSRLEHA | SEQ ID NO: 37 |
| LHELARQVSRLEHA | SEQ ID NO: 38 |
| LHELARQVSRLEHA | SEQ ID NO: 39 |
| LHQLAREVSRLEHA | SEQ ID NO: 40 |
| LHSLARSVSRLEHA | SEQ ID NO: 41 |
| AKSVAESLHSLARS | SEQ ID NO: 42 |
| AHSVAESLHSLARS | SEQ ID NO: 43 |
| AHSVAKSLHSLARS | SEQ ID NO: 44 |
| AHSVAESLHSLAES | SEQ ID NO: 45 |
| AQSVAQSLAQLAQS | SEQ ID NO: 46 |
| AESVAESLAELAES | SEQ ID NO: 47 |

-continued

ANSVANSLANLANS — SEQ ID NO: 48

ADSVADSLADLADS — SEQ ID NO: 49

AQSVAESLAQLAES — SEQ ID NO: 50

AESVAESLAELAES — SEQ ID NO: 51

ANSVAESLANLAES — SEQ ID NO: 52

ADSVAESLADLAES — SEQ ID NO: 53

MKQLADSLHQLARQVSRLEHA — SEQ ID NO: 54

MKQLADSLHQLARQVSRLEHA — SEQ ID NO: 55

MKQLADSLMQLARQVSRLESA — SEQ ID NO: 57

LMQLARQMKQLADSLMQLARQVSRLESA — SEQ ID NO: 58

MKELADSLMQLARQVDRLESA — SEQ ID NO: 59

MKQLADSLHQLAHQVSHLEHA — SEQ ID NO: 60

MEELADSLEELARQVEELESA — SEQ ID NO: 61

MKKLADSLKKLARQVKKLESA — SEQ ID NO: 62

MKQLADSLHQLAHKVSHLEHA — SEQ ID NO: 63

EISALEKEISALEKEISALEK — SEQ ID NO: 64

KISALKEKISALKEKISALKE — SEQ ID NO: 65

MKELADSLHELAREVSRLEHA — SEQ ID NO: 66

MKELADSLHQLARQVSRLEHA — SEQ ID NO: 67

MKQLADSLHELARQVSRLEHA — SEQ ID NO: 68

MKQLADSLHQLARQVSRLEHA — SEQ ID NO: 69

MKELADSLHELARQVSRLEHA — SEQ ID NO: 70

MKELADSLHQLAREVSRLEHA — SEQ ID NO: 71

MKQLADSLHELAREVSRLEHA — SEQ ID NO: 72

AKSLAESLHSLARSVSRLEHA — SEQ ID NO: 73

AKSVAESLHSLARSVSRLVEHA — SEQ ID NO: 74

AHSVAESLHSLARSVSRLVEHA — SEQ ID NO: 75

-continued

AHSVAKSLHSLARSVSRLVSHA — SEQ ID NO: 76

AHSVAESLHSLAESVSELVSHA — SEQ ID NO: 77

AQSVAQSLAQLAQSVSQLVSQA — SEQ ID NO: 78

AESVAESLAELAESVSELVSEA — SEQ ID NO: 79

ANSVANSLANLANSVSNLVSNA — SEQ ID NO: 80

ADSVADSLADLADSVSPLVSDA — SEQ ID NO: 81

AQSVAESLAQLAESVSELVSQA — SEQ ID NO: 82

AESVAESLAELAESVSELVSEA — SEQ ID NO: 83

ANSVAESLANLAESVSELVSNA — SEQ ID NO: 84

ADSVAESLADLAESVSELVSDA — SEQ ID NO: 85

MD(PS-MKQLADS-LHQLARQ-VSRLEHA-D)$_4$ — SEQ ID NO: 86

MD(PS-MKQLADS-LHQLARQ-VSRLEHA-D)$_2$ — SEQ ID NO: 87

MD(PS-AKSLAES-LHSLARS-VSRLEHA-D)$_4$ — SEQ ID NO: 88

MD(PS-AKSVAES-LHSLARS-VSRLVEHA-D)$_4$ — SEQ ID NO: 89

MD(PS-AHSVAES-LHSLARS-VSRLVEHA-D)$_4$ — SEQ ID NO: 90

MD(PS-AHSVAKS-LHSLARS-VSRLVSHA-D)$_4$ — SEQ ID NO: 91

MD(PS-AHSVAES-LHSLAES-VSELVSHA-D)$_4$ — SEQ ID NO: 92

MD(PS-AQSVAQS-LAQLAQS-VSQLVSQA-D)$_4$ — SEQ ID NO: 93

MD(PS-ANSVANS-LANLANS-VSNLVSNA-D)$_4$ — SEQ ID NO: 94

MD(PS-AQSVAES-LAQLAES-VSELVSQA-D)$_4$ — SEQ ID NO: 95

MD(PS-ANSVAES-LANLAES-VSELVSNA-D)$_4$. — SEQ ID NO: 96

MD(PS-MKQLADS-LMQLARQ-VSRLESA-D)$_4$. — SEQ ID NO: 97

MD(PS-LMQLARQ-MKQLADS-LMQLARQ-VSRLESA)$_4$. — SEQ ID NO: 98

MD(PS-MKELADS-LMQLARQ-VDRLESA-D)$_4$. — SEQ ID NO: 99

MD(PS-MKQLADS-LHQLAHS-VSHLEHA-D)$_4$. — SEQ ID NO: 100

MD(PS-MEELADS-LEELARQ-VEELESA-D)$_4$. — SEQ ID NO: 101

MD(PS-MKKLADS-LKKLARQ-VKKLESQ-D)$_4$. — SEQ ID NO: 102

MD(PS-MKQLADS-LHQLAHK-VSHLEHA-D)$_4$. SEQ ID NO: 103

MD(PS-EISALEK-EISALEK-EISALEK-D)$_4$. SEQ ID NO: 104

MD(PS-KISALKE-KISALKE-KISALKE-D)$_4$. SEQ ID NO: 105

MD(PS-MKELADS-LHELARE-VSRLEHA-D)$_4$. SEQ ID NO: 106

MD(PS-MKELADS-LHQLARQ-VSRLEHA-D)$_4$. SEQ ID NO: 107

MD(PS-MKQLADS-LHELARQ-VSRLEHA-D)$_4$. SEQ ID NO: 108

MD(PS-MKELADS-LHELARQ-VSRLEHA-D)$_4$. SEQ ID NO: 109

MD(PS-MKELADS-LHQLARE-VSRLEHA-D)$_4$. SEQ ID NO: 110

MD(PS-MKQLADS-LHELARE-VSRLEHA-D)$_4$. SEQ ID NO: 111

MD(PS-AESVAES-LAELAES-VSELVSEA-D)$_4$. SEQ ID NO: 112

MD(PS-ADSVADS-LADLADS-VSPLVSDA-D)$_4$. SEQ ID NO: 113

MD(PS-AESVAES-LAELAES-VSELVSEA-D)$_4$. SEQ ID NO: 114

MD(PS-ADSVAES-LADLAES-VSELVSDA-D)$_4$. SEQ ID NO: 115

MDPS(MKQLADSLHQLARQVSRLEHA-DPS)$_3$MKQLADS-LHQLARQVSRLEHA-EPS SEQ ID NO: 116

Ac-AAAAAAD SEQ ID NO: 117

Ac-VVVVVVD SEQ ID NO: 118

Ac-VVVVVVDD SEQ ID NO: 119

Ac-LLLLLLDD SEQ ID NO: 120

Ac-GGGGDD SEQ ID NO: 121

Ac-GGGGGGDD SEQ ID NO: 122

Ac-GGGGGGGGDD SEQ ID NO: 123

Ac-GGGGGGGGGGDD SEQ ID NO: 124

Ac-VVVVVVKK SEQ ID NO: 125

Ac-LLLLLLKK SEQ ID NO: 126

Ac-AAAAAAK SEQ ID NO: 127

Ac-VVVVVVH SEQ ID NO: 128

Ac-LLLLLLK SEQ ID NO: 129

HHVVVVVV SEQ ID NO: 130

KVVVVVV SEQ ID NO: 131

The charged peptide module may be any peptide that is capable of driving formation of an inorganic silica layer near a liquid-liquid interface. In some embodiments, the charged peptide module is a positively charged peptide module.

In some embodiments, the charged peptide module comprises 1 to 10 hydrogen bond donating amino acid residues, especially 1 to 8 hydrogen bond donating amino acid residues. In some embodiments, the hydrogen bond donating amino acid residues are independently selected from serine and tyrosine.

In some embodiments, the charged peptide module comprises 1 to 15 positively charged amino acid residues, especially 4 to 12 positively charged amino acid residues. In some embodiments, the positively charged amino acid residues are independently selected from lysine, arginine, histidine and ornithine, especially lysine, histidine and arginine.

In some embodiments, the charged peptide module comprises 1 to 10 uncharged or non-hydrogen bond donating amino acid residues, especially 1 to 5 uncharged or non-hydrogen bond donating amino acid residues. In particular embodiments, the uncharged or non-hydrogen bond donating are selected from polar amino acid residues and hydrophobic amino acid residues. In some embodiments, the uncharged or non-hydrogen bond donating amino acid residues are independently selected from glycine, alanine, valine, leucine, isoleucine, methionine, asparagine, glutamine, phenylalanine, tryptophan and aminoisobutyric acid, especially glycine, alanine, valine, leucine and isoleucine.

In some embodiments, the charged peptide module is selected from:

SSKKSGSYSGSKGSKRRIL SEQ ID NO: 132

RKKRKKRKKRKKGGGY SEQ ID NO: 133

SGSKGSKRRIL SEQ ID NO: 134

KSGSYSGSKGSKRRIL SEQ ID NO: 135

SGSKGSKRR SEQ ID NO: 136

SSKKSGSYSGSKGSK SEQ ID NO: 137

LIRRSSKKSGSY SEQ ID NO: 138

SSKKSGSYRRIL SEQ ID NO: 139

APPGHHHWHIHH SEQ ID NO: 140

KPSHHHHHTGAN SEQ ID NO: 141

MSPHPHPRHHHT SEQ ID NO: 142

-continued

MSPHHMHHSHGH  SEQ ID NO: 143

LPHHHHLHTKLP  SEQ ID NO: 144

APHHHHPHHLSR  SEQ ID NO: 145

RGRRRRLSCRLL  SEQ ID NO: 146

VKVKVKVKV$^D$P$^L$PTKVKVKVKV  SEQ ID NO: 147

VKVKVKVKV$^D$P$^L$PTKVEVKVKV  SEQ ID NO: 148

KIAALKQKIASLKQEIDALEYENDALEQ$^a$  SEQ ID NO: 149

KIRRLKQKNARLKQEIAALEYEIAALEQ$^a$  SEQ ID NO: 150

CH$_3$(CH$_2$)$_{14}$CO-AAAAKKKK  SEQ ID NO: 151

CH$_3$(CH$_2$)$_{14}$CO-AAAAHHHH  SEQ ID NO: 152

IIIK  SEQ ID NO: 153

CKKCKK$^b$  SEQ ID NO: 154

$^a$Self-assembling peptide fibres that are formed by block A (KIAALKQKIASLKQ) which complements D (EIAALEYEIAALEQ) and B (EIDALEYENDALEQ) complements C (KIRRLKQKNARLKQ). This leads to sticky end dimers that assemble further into fibres. The register of the assembly is partly maintained by the asparagine residues.

$^b$The two tripeptides (CKK) are connected through a disulfide bridge (-S-S-).

In some embodiments, the surface-active polypeptide module and the charged peptide module are conjugated directly to one another via an amide bond. In other embodiments, the surface-active polypeptide module and the charged peptide module are conjugated to one another by a linker. In a particular embodiment, the surface-active polypeptide module and the charged peptide module are conjugated directly to one another via an amide bond.

In some embodiments, where the surface-active polypeptide and the charged peptide are conjugated to one another by a linker, the linker is a peptide linker of 1 to 10 amino acid residues in length, especially 1 to 5 amino acid residues in length. The linker sequence may be formed from any amino acid residue. In some embodiments, the amino acid sequence linking the surface-active polypeptide module and the charged peptide module comprises an α-helix breaking amino acid residue. This residue assists in terminating any α-helical structure in the surface-active polypeptide and may further provide flexibility in the amino acid linking sequence to orientate the charged peptide module away from the liquid-liquid interface into the aqueous or polar phase when the mineralizing biosurfactant is located at a liquid-liquid interface. α-Helix breaking amino acid residues include amino acid residues that are unable to contribute to α-helical structure, such as proline, have high flexibility, for example, serine. The charged group on aspartic acid is also known to have low helix propensity. Common α-helix breaking amino acid residues include proline and glycine.

The amino acid sequence linking the surface-active polypeptide module and the charged polypeptide module may also include one or more residues that impart flexibility. In some embodiments, the flexibility is imparted by one or more amino acid residues having a small side chain, for example, glycine, serine, alanine, valine, cysteine and threonine. In some embodiments, these same amino acids play a dual role of conferring flexibility to the overall sequence of linking amino acid residues as well as helix termination.

In some embodiments, the surface-active polypeptide module is located at the N-terminus of the mineralizing biosurfactant and the charged peptide module is located at the C-terminus of the mineralizing biosurfactant. In other embodiments, the surface-active polypeptide module is located at the C-terminus of the mineralizing biosurfactant and the charged peptide module is located at the N-terminus of the mineralizing biosurfactant. In particular embodiments, the surface-active polypeptide module is located at the N-terminus of the mineralizing biosurfactant and the charged peptide module is located at the C-terminus of the mineralizing biosurfactant.

In some embodiments, the charged peptide module is attached to a side chain of an amino acid residue of the surface-active peptide module. For example, the C-terminal carboxylic acid of the charged peptide module may be linked to an amine group of a lysine or ornithine residue in the surface active polypeptide via an amide bond. Alternatively, the N-terminal amino group of the charged peptide module may be linked to a side chain carboxylic acid of an amino acid residue in the surface-active polypeptide module via an amide bond.

In some embodiments, the mineralizing biosurfactant has a free N-terminal amino group and a free C-terminal carboxy group. In other embodiments, the N-terminal amino group is capped with an N-terminal capping group and/or the C-terminal carboxy group is capped with a C-terminal capping group. In particular embodiments, the N-terminal amino group is capped with an N-terminal capping group and the C-terminal carboxy group is capped with a C-terminal capping group.

As used herein, the N-terminal capping group, when present, is any group that blocks the reactivity of the N-terminal amino group. Suitable examples include acyl groups such as acetyl (ethanoyl), propanoyl, butanoyl, pentanoyl and hexanoyl, especially acetyl.

As used herein, the C-terminal capping group, when present, is any suitable group that blocks the reactivity of the C-terminal carboxyl group. Suitable examples include amino groups thereby forming an amide. Examples include —NH$_2$, —NH(alkyl) and —NH(alkyl)$_2$.

Suitable mineralizing biosurfactants include any combination of a surface-active polypeptide of SEQ ID NO: 1 to 130 and a charged peptide of SEQ ID NO: 131 to 152; especially:

SEQ ID NO: 155
Ac-MKQLAHSVSRLEHA-SSKKSGSYGGSKGSKRRIL-NH$_2$

SEQ ID NO: 156
Ac-MKQLAHSVSRLEHA-RKKRKKRKKRKKGGGY-NH$_2$

SEQ ID NO: 157
MDPSMKQLADSLHQLARQVSRLEHADPSMKQLADSLHQLARQVSRLEHA

DPSMKQLADSLHQLARQVSRLEHADPSMKQLADSLHQLARQVSRLEHAE

PS-RKKRKKRKKRKKGGGY

Without wishing to be bound by theory, it is postulated that the surface-active polypeptide module (Sur peptide module) self-assembles at the liquid-liquid interface to stabilize the nanoemulsion droplet. In some instances, stabilization may be enhanced by intermolecular interactions between laterally oriented side chains of adjacent surface-active polypeptide modules at the interface. In cases where the charged peptide module has multiple charges, the high charge on this module may provide additional DLVO stabilization at the interface. While the surface-active polypeptide module is at the interface, the charged peptide module (Si peptide module) extends into the aqueous phase of the micro- or nano-emulsion. The amino acids of the charged peptide module, such as lysine, arginine, serine and tyrosine, interact with silica species in the aqueous phase by providing cationic charges and hydrogen bonding sites. These amino acids may act as the nucleation sites for reactive silanolate (≡Si—$O^-$) and silanol (≡Si—OH) species that participate in silicification and direct the silca growth through condensation of these species, forming siloxane (≡Si—O—Si≡) at the oil-water interface. This process is schematically outlined in FIG. 1.

The mineralizing biosurfactant or the surface-active polypeptide module or charged peptide module may be prepared by methods known in the art, such as solid phase synthesis or solution phase synthesis using Fmoc or Boc protected amino acid residues. Alternatively, the mineralizing biosurfactant may be prepared by recombinant techniques as known in the art using standard microbial culture technology, genetically engineered microbes and recombinant DNA technology (Sambrook and Russell, Molecular Cloning: A Laboratory Manual ($3^{rd}$ Edition), 2001, CSHL Press).

In brief, the genetically engineered microbes contain a polynucleotide sequence that comprises a nucleotide sequence that encodes the polypeptide. The nucleotide sequence is operably linked to a promotor sequence. The microbes may be any microbes suitable for use in culturing processes such as fermentation. Examples of suitable microbes include *E. coli, Saccharomyces cerevisiae, Bacillis subtilis*, and *Piccia pastoris*, especially *E. coli*. Any culturing process may be used, for example, fermentation. During the culturing process the microbes express the polypeptide.

Once culturing is complete, the microbial cells may be further treated in the culture medium, for example, the fermentation broth, or may be isolated and stored or resuspended in the same or different media. Cells may be isolated by commonly used techniques such as centrifugation or filtration. Optionally cells may undergo a cell-conditioning step after cell recovery. For example, the cells may be collected and re-suspended in water or buffered solution prior to storage or use.

After culturing, the microbial cells are disrupted to provide a disruptate composition comprising soluble proteins and cell debris. Cell disruption may be achieved by means known in the art including mechanical means and non-mechanical means. Small scale disruption may be achieved by methods such as sonication or homogenization. Large scale disruption may be achieved by mechanical means such as bead milling, homogenization and microfluidization, or non-mechanical means including physical means such as decompression, osmotic shock and thermolysis; chemical means such as antibiotics, chelating agents, chaotropes, detergents, solvents, hydroxide and hyperchlorite; and enzymatic means such as lytic enzymes, autolysis and cloned phage lysis.

Optionally after the cell disruption step, solid cell debris is removed by techniques known in the art such as centrifugation or filtration. Removal of cell debris provides a solution of soluble cell proteins that includes the polypeptide mineralizing biosurfactant.

Purification of the polypeptide from other contaminating cell proteins and polypeptides may be achieved by treating the cell disruptate, either directly from cell disruption or clarified by removal of insoluble cell debris, with a kosmotropic salt in an amount suitable to salt-out cell derived contaminants but salt-in the mineralizing surfactant.

The kosmotropic salt may be formed from a kosmotropic ion. Examples of kosmotropic ions include sulfate, carbonate, phosphate, lithium, fluoride, calcium and acetate. The counterion of the salt may be any suitable counterion of opposite charge.

The amount of kosmotropic salt is an amount suitable to precipitate contaminating proteins and polypeptides but not the polypeptide mineralizing biosurfactant of interest. This amount can be readily determined by those skilled in the art by exposing a sample of cell disruptate, with or without clarification, to a range of salt concentrations, separating the precipitate, and supernatant and analyzing the supernatant to determine the amount of contaminating proteins in the supernatant and pellet by SDS-PAGE or HPLC. In some embodiments, the amount of kosmotropic salt is in the range of 0.2 M and 2.0 M. In some embodiments, the amount of kosmotropic salt is in the range of 0.2 M and 0.5 M, for example, about 0.25 M. In other embodiments, the amount of kosmotropic salt is in the range of 0.5 M and 2.9 M, for example, 1.0 M and 2.0 M, especially about 1.5 M.

After treatment with the kosmotropic salt, the precipitate containing cell contaminants and the supernatant containing the polypeptide may be separated by methods known in the art, such as gravity sedimentation, centrifugation or filtration.

Alternatively, established chromatography methods may be used to separate the cell contaminants and mineralizing biosurfactant.

In some embodiments, where the surface-active polypeptide module has a folded tertiary structure such as a 4-helix bundle, the mineralizing biosurfactant or the surface-active polypeptide may be prepared recombinantly and purified and isolated using a thermal purification method in which the cell disruptate is exposed to a kosmotropic salt at an elevated temperature such as above 45° C. or above 60° C. or between 85° C. and 100° C., such a purification method is described in detail in WO 2012/079125.

In particular embodiments, the mineralizing biosurfactant is prepared as one polypeptide sequence optionally including amino acid linking sequences.

In other embodiments, the surface-active polypeptide module and the charged peptide module are prepared separately and conjugated together by methods known in the art. For example, the C-terminus of one module may be conjugated to the N-terminus of the other module by peptide bond formation (amide bond formation), as is well known in the art. In brief, the C-terminal or side chain carboxylic acid is activated by formation of a reactive species such as an acyl chloride, anhydride, a carbodiimide, a phosphonium species and the like, and the activated carboxylic acid is reacted with the N-terminal or side chain amino group to form an amide bond.

3. Micro- and Nano-Emulsions and Micro- and Nano-Capsules

In another aspect of the present invention, there is provided a micro- or nano-emulsion comprising the mineralizing biosurfactant described above.

The micro- or nano-emulsion is typically an oil-in-water micro- or nano-emulsion where an oil droplet is dispersed in a polar or aqueous phase. The microemulsion has an average oil droplet size of 900 nm to 100 µm, especially between 900 nm and 50 µm, more especially between 900 nm and 5 µm. The nanoemulsion has an average oil droplet size of less than 900 nm, especially in the range of between 20 and 750 nm or 30 and 500 nm, more especially in the range of 30 to 300 nm.

The micro- or nano-emulsions include a polar or aqueous phase and an oil phase wherein the oil phase is immiscible with the polar or aqueous phase. Suitable polar or aqueous phases include water, buffer, methanol, ethanol, propanol and mixtures thereof. Suitable oil phases include neutral esters of saturated coconut and palm kernel oil-derived caprylic and capric fatty acids and glycerine or propylene glycol such as Miglyol® 810, 812, 818, 829 and 840, edible oils such as olive oil, sunflower oil, safflower oil, grapeseed oil, sesame oil, coconut oil, canola oil, corn oil, flaxseed oil, palm oil, palm kernel oil, peanut oil and soyabean oil, or triglycerides rich in unsaturated fatty acids or mixtures thereof.

In some embodiments, the oil phase is present in the initial emulsion in an amount between 0.5 to 10% v/v, especially 0.5 to 5% v/v, more especially 1 to 3% v/v, most especially about 2% v/v.

The micro- and nano-emulsions of the invention may be prepared by methods known in the art for preparing micro- and nano-emulsions, for example, high energy mixing, couette shear, homogenization, sonication, dropwise dispersion or the use of microfluidic platforms. For example, the micro- or nano-emulsion may be prepared by mixing the oil and aqueous phase where the aqueous phase comprises the at least one mineralizing biosurfactant, by ultrasonication or high shear mixing. Micro-emulsions may be prepared using lower concentrations of biosurfactant and lower energy mixing than used for nano-emulsions.

In some embodiments, stabilization of the mineralizing biosurfactant at the liquid-liquid interface results from DLVO interactions. In some embodiments, the aqueous phase further comprises a component that enhances interaction of the side chains of the amino acid residues of the surface-active polypeptide module in the mineralizing biosurfactant at the liquid-liquid interface. This enhances the stability of the micro- or nano-emulsion against coalescence. Suitable components include metal ions which may form bridges between two charged laterally oriented side chains of the surface-active peptide which are located on adjacent polypeptide biosurfactants. Suitable metal ions include calcium ions and magnesium ions, transition metal ions such as titanium ions, vanadium ions, chromium ions, manganese ions, iron ions, cobalt ions, nickel ions, copper ions, zinc ions and molybdenum ions, and lanthanide ions such as lanthanum ions, cerium ions, praseodynium ions, neodynium ions, promethium ions, samarium ions, europium ions, gadolinium ions, terbium ions, dysprosium ions, holmium ions, erbium ions, thulium ions, ytterbium ions, and lutetium ions. In particular embodiments, the metal ions are selected from one or more of calcium, magnesium and transition metal ions, especially calcium, magnesium, copper, nickel and zinc ions, more especially zinc ions.

The metal ions may be included in the micro- or nano-emulsion aqueous or polar phase in the form of a salt. The salt may be selected for suitablility for the use of the micro- or nano-emulsion or subsequent micro- or nano-capsule. Suitable salts include halides, such as fluorides, chlorides, bromides and iodides, phosphates, sulfates and the like, especially chlorides such as zinc chloride.

In some embodiments, the oil core of the nanoemulsion comprises a compound for delivery to a human or animal body, such as a pharmaceutical or veterinary product, or a compound for delivery to an environment, such as a household, industrial or agricultural environment, for example a pesticide, herbicide, microbicide and the like.

In some embodiments, the compound to be delivered to the human or animal body or environment is sparingly soluble, slightly soluble, very slightly soluble or practically insoluble in water but is very soluble in the oil phase of the micro- or nano-emulsion. In other embodiments, the pharmaceutically active agent is soluble, freely soluble or very soluble in water and is included in the micro- or nano-emulsion oil phase on a nanoparticle such as a dendrimer, mesoporous silica nanoparticle or a polymeric nanoparticle such as those made of polycaprolactone (PCL) or polylactic-co-glycolic acid (PGLA), or in an aqueous micro- or nano-droplet within the oil phase, or by oil-phase solubilisation using a surfactant or polymer to alter the surface properties of the pharmaceutically active agent from hydrophilic to hydrophobic.

Suitable sparingly soluble, slightly soluble, very slightly soluble and insoluble pharmaceutically active agents include cancer drugs such as taxol, paclitaxel, docetaxel, carbazitaxel, camptothecin, 10-hydroxycamptothecin, irinotecan, doxorubicin, etoposide, temolzolomide, teniposide, amsacrine, actinomycin D, ellipticine and bis-dioxopiperazines such as ICRF-1893; corticosteroids such as methylprednisilone, prednisilone, prednisone, betametasone and budesonid; metalloprotease inhibitors such as marimastat; and steroid hormones such as testosterone, progesterone and levonorgestrel.

Suitable pharmaceutically active agent soluble in aqueous solution include protein antigens or siRNA. In some embodiments, the protein antigens may elicit an immunogenic response against an invading pathogen, for example, in infectious disease. In other embodiments, the protein antigen may elicit a tolerogenic response in an autoimmune disease or in organ replacement or repair. Suitable protein antigens include tumour-associated cell lysates, CD1, CD3, CD4, CD5, CD8, CD15, CD27, CD30, CD31, CD44, C47, LRRC16 and prostate specific antigen (PSA) or other protein antigens associated with autoimmunity or infectious disease. Tumour cell lysates are derived from a patient's tumour and contain antigens specific to the tumour from which they are derived optionally together with cytokines, allowing for the use of micro- and nano-emulsions directed to personal medicine approaches.

In some embodiments, where a tolerogenic response is required from the pharmaceutically active agent, the micro- or nano-emulsion further comprises at least one inhibitor of NF-κB in an amount sufficient to inhibit the NF-κB pathway of the antigen presenting cells to which the antigen is being delivered. Suitable NF-κB inhibitors include antioxidants, proteosome and protease inhibitors of REL/NF-κB, phosphorylation and/or degradation inhibitors and other NF-κB inhibitors. Suitable antioxidants include α-lipoic acid, α-tocopherol, aged garlic extract (allicin), 2-Amino-1-methyl-6-phenylimidazo[4,5-b]pyridine (PhIP), allopurinol, 5,6,3', 5'-tetramethoxy-7,4'-hydroxyflavone, bis-eugenol, butylated hydroxyanisole (BHA), 3,4-dihydroxycinnamic acid, curcumin, diethyldithiocarbamate, ethyl pyruvate, folic acid, glutathione, hydroquinone, melatonin, N-acetyl-cysteine, quercetin, spironolactone and vitamin C Suitable proteosome and protease inhibitors of REL/NF-kB include N-acetyl-leucinyl-leucinyl-norleucinyl (ALLnL), N-acetyl-leucinyl-leucinyl-methionyl (LLM), carbobenzoxyl-leucinyl-leucinyl-norvalinyl (Z-LLnV), carbobenzoxyl-leucinyl-leucinyl-leucinyl (Z-LLL), bortezomib, cyclosporine A, tacrolimus, disulfiram, N-acetyl-DL-phenylalanine-β-naphthyl ester, N-benzoyl L-tyrosine-ethyl ester, 3,4-dichloroisocoumarin, diisopropyl fluorophosphate, N-α-tosyl-L-phenylalanine chloromethyl ketone and N-α-tosyl-L-lysine chloromethyl ketone. Suitable phosphorylation or degradation inhibitors include desloratiadine, salmeterol, fluticasone propionate, LY29, LY30, evodiamine, geldanamycin, 4-(2'-aminoethyl)amino-1,8-dimethylimidazo(1,2-α)-quinoxaline, cobrotoxin, nitric oxide, thienopyridine, 2-amino-6-[2-(cyclopropylmethoxy)-6-hydroxyphenyl]-4-piperidin-4-yl nicotinonitrile, N-(4-hydroxyphenyl)retinamide, scytonemin, zerumbone, silibinin, sulfasalazine, quercetin, rosmarinic acid, staurosporine, gamma-tocotrienol, thalidomide, anethole, benzylisothiocyanate, digitoxin, interferon-α, methotrexate, capsaicin, genistein and ursodeoxycholic acid. Other NF-kB inhibitors include α-pinene, indole-3-carbinol, 1,2,3,4,6-penta-O-galloyl-β-D-glucose, selenomethionine, neomycin, rapamycin, ethylpyruvate, 2-acetylaminofluorene, 7-amino-4-methylcoumarin, camptothecin, cinnamaldehyde, clarithromycin, erythromycin, glycyrrhizin, linoleic acid, 2-methoxyestradiol, prostaglandin E2, rapomycin, raloxifene, ribavirin, ritonavir, rosiglitazone and xylitol.

In some embodiments, the compound to be delivered is a veterinary compound. In some embodiments, the veterinary compound is a protein associated with animal disease, such as VirB91, or other proteins associated with animal diseases, such as cattle diseases.

In some embodiments, the compound to be delivered is a compound suitable for use as a diagnostic agent, including but not limited to, fluorescent agents, magnetic particles and other imaging agents. Suitable fluorescent agents include fluorophores such as green fluorescent protein, fluorescein, rhodamine, eosin, indocarbocyanine, merocyanine, nile red, nile blue, cresyl violet, proflavin, acridine orange, acridine yellow, auramine, malachite green, crystal violet and porphin. Suitable contrast agents for imaging include gadolinium compounds such as gadoterate, gadodiamide, gadopentetate, gadoteridol, gadoversetamide, gadoxetate, gadobutrol, gadobenate and Gd-DOTA, techtinium compounds such as techtinium sestamibi, techtinium bicisate and techtinium tetrafosmin, iodine compounds such as metrizamide, ioxaglate, ioversol, iopamidol and iohexol, indium compounds such as indium petreotide, fluorine compounds such as fluorodeoxyglucose or fluorine 19; iron oxides such as feridex, resovist, sinenem, lumirem and clariscan; and others such as gold nanoparticles and iodine.

In some embodiments, the compound to be delivered is a pesticide such as an acaricide, an avicide, algicide, antifouling agent, antimicrobial, antifeedant, bactericide, biocide, chemisterilant, fungicide, herbicide, herbicide safener, insect attractant, insect repellent, mammal repellent, bird repellent, insecticide, fumigant, disinfectant, sanitiser, mating disrupter, miticide, molluscicide, nematicide, ovicide, pheromone, plant activator, plant growth regulator, rodenticide, synergist, termiticide or virucide. Suitable pesticides include, but are not limited to, fipronil, organochlorides such as aldrin, chlordane, chlordecone, DDT, dieldrin, endosulfan, endrin, heptachlor, hexachlorobenzene, lindane (gamma-hexachlorocyclohexane), methoxychlor, mirex, pentachlorophenol and TDE, organophosphates such as acephate, azinphos-methyl, bensulide, chlorethoxyfos, chlorpyrifos, chlorpyriphos-methyl, diazinon, dichlorvos (DDVP), dicrotophos, dimethoate, disulfoton, ethoprop, fenamiphos, fenitrothion, fenthion, fosthiazate, malathion, methamidophos, methidathion, mevinphos, monocrotophos, naled, omethoate, oxydemeton-methyl, parathion, parathion-methyl, phorate, phosalone, phosmet, phostebupirim, phoxim, pirimiphos-methyl, profenofos, terbufos, tetrachlorvinphos, tribufos and trichlorfon, carbamates such as aldicarb, bendiocarb, carbofuran, carbaryl, dioxacarb, fenobucarb, fenoxycarb, isoprocarb and methomyl, 2-(1-Methylpropyl)phenyl methylcarbamate, pyrethroids such as allethrin, bifenthrin, cyhalothrin, lambda-cyhalothrin, cypermethrin, cyfluthrin, deltamethrin, etofenprox, fenvalerate, permethrin, phenothrin, prallethrin, resmethrin, tetramethrin, tralomethrin and transfluthrin, neonicotinoids such as acetamiprid, clothianidin, imidacloprid, nitenpyram, nithiazine, thiacloprid and thiamethoxam, ryanoids such as rynaxypyr, insect growth regulators including benzoylureas such as diflubenzuron and flufenoxuron, methoprene, hydroprene and tebufenozide. Suitable herbicides include synthetic auxins such as 2,4-D, dicamba, fluroxypyr and picloram, pyridine herbicides such as clopyralid and aminopyralid, triazine herbicides such as atrazine, and other herbicides such as glufosinate ammonium, fluazifop, glyphosate, imazapyr, imazapic, imazamox, metolachlor, paraquat pendimethalin, sodium chlorate and triclopyr.

In some embodiments, the micro- or nano-emulsion formed may be concentrated prior to use by methods known in the art including gravitational or centrifugal separation.

In yet another aspect of the present invention, there is provided a silica micro- or nano-capsule comprising an oil droplet stabilized by a mineralizing biosurfactant as described above and a silica shell encapsulating the stabilized oil core.

The oil droplet may be any oil suitable for solubilizing or carrying the compound to be delivered. Suitable oil phases include neutral esters of saturated coconut and palm kernel oil-derived caprylic and capric fatty acids and glycerine or propylene glycol such as Miglyol® 810, 812, 818, 829 and 840, edible oils such as olive oil, sunflower oil, safflower oil, grapeseed oil, sesame oil, coconut oil, canola oil, corn oil, flaxseed oil, palm oil, palm kernel oil, peanut oil and soyabean oil, or triglycerides rich in unsaturated fatty acids or mixtures thereof.

In some embodiments, the oil droplet further comprises a compound for delivery to an environment, such as a household, industrial or agricultural environment, for example a pesticide, herbicide, microbicide and the like as described above.

The microcapsules have an average diameter of less than 150 μm, especially between 1 μm and 100 μm, more especially between 1 μm and 30 μm and most especially between 1 μm and 5 μm The nanocapsules having an average diameter of less than 1 μm, especially between 50 nm and 750 nm, more especially between 70 nm and 500 nm, more especially between 80 nm and 400 nm.

The thickness of the silica shell may be adapted to assist with the release of the compound to be delivered. In some embodiments, the silica shell has a thickness in the range of 5 to 100 nm, 10 to 60 nm or 10 to 50 nm. In embodiments where release is less inhibited, the silica shell thickness may be in the range of 10 to 40 nm, 10 to 30 nm, 10 to 20 nm, especially 10 to 20 nm. In embodiments where release is desired to be slower or inhibited, the thickness of the silica shell may be in the range of 30 to 80 nm, 40 to 70 nm or 40 to 60 nm, especially 40 to 50 nm.

In some embodiments, the silica shell is an amorphous silica shell.

In some embodiments, the nanocapsule further includes a pharmacokinetic modifying agent and/or a targeting agent located on the surface of the micro- or nano-capsule. The pharmacokinetic agent and/or targeting agent are attached to the surface of the micro- or nano-capsule using methods known in the art. For example, carboxylic acids on the pharmacokinetic agent or targeting agent may be covalently linked to the hydroxy group of silanol groups on the silica shell surface. Alternatively, the surface of the silica shell may be coated with amine functionality, for example, with (3-aminopropyl)triethoxysilane (APTES) and their pharmacokinetic agents bearing a carboxylic acid may be coupled by methods known for amine formation, such as with a carbodiimide and base, for example, 1-ethyl-3-(3-dimethylaminopropyl) carbodiimide (EDC) and N-hydroxysuccinamide (NHS). In some embodiments, the pharmacokinetic modifying agent is a polyalkylene glycol, a polyalkyloxazoline such as polyethyloxazoline (PEOX), or polyvinylpyrolidone, especially a polyalkylene glycol such as polyethylene glycol or polypropylene glycol, more especially polyethylene glycol (PEG). The polyethylene glycol may have a molecular weight between 2500 and 25000 Da, especially 2500 and 20000 Da. In a particular embodiment, the PEG has a molecular weight of about 5000 Da. The targeting agent may be any molecule that binds to a cell surface receptor in the target tissue or organ to which the nanocapsule is to be delivered. For example, the targeting agent may be a small molecule such as folate or an oestrogen, peptides such as tumor-targeting peptide or may be an antibody or antibody fragment such as an scFv or diabody, directed to a particular cell surface receptor.

Suitable targeting peptides include Lyp-1 (CGNKRTRGC, SEQ ID NO: 160), Bombesin peptide (QQRLGNQWAVGHLM, SEQ ID NO: 161) and suitable tumor-targeting peptides include RGD peptides such as RGD, cyclic RGD dimer and CRGDKRGPDEC (iRGD, SEQ ID NO: 162).

Suitable antibodies or fragments thereof include anti-PSMA and anti-HER2, target receptors for IL-6, IFN8, VEGF, EGF, CA-125, Clec9A, Clec12A, TNF-α, CD4, CD8, CD19, CD64, CD3, CD28, CD40, CD326 and CD20 (rituximab), or monoclonal antibodies targeting cancer-associated proteoglycans such as melanoma-associated proteoglycans, or cancer-associated gangliosides, for example, GD2 and GD3.

The silica micro- and nano-capsules of the present invention may be prepared using the micro- or nano-emulsion of the invention as a template to nucleate silica onto the stabilized micro- or nano-emulsion.

In another aspect of the present invention, there is provided a method of making a silica micro- or nano-capsule comprising the steps of:
A) forming a stabilized micro- or nano-emulsion by mixing a composition comprising:
   a) an oil phase;
   b) an aqueous phase; and
   c) a mineralizing biosurfactant according to the invention; and
B) mixing the micro- or nano-emulsion with silica or a silica precursor.

The micro- or nano-emulsion formed is a micro- or nano-emulsion of the invention as described above.

The silica or silica precursor is any silica containing compound that will react with the positively charged peptide module of the mineralizing biosurfactant and form the silica shell. Suitable silica or silica precursors include alkoxylated silanes such as tetraethoxysilane, tetramethoxysilane, methyltriethoxysilane, phenyltriethoxysilane, trimethylethoxysilane, sodium silicate ($Na_2Si_3O_7$), dipotassium silicon triscatecholate ($K_2[Si(C_6H_4O_2)_3].2H_2O$), silica sol (silica nanoparticles with diameter of 10-12 nm, 40% $SiO_2$, 0.4% $Na_2O$), ethylene glycol modified silane ($SiC_2H_8O_2)_4$), and the like.

The concentration of silica or silica precursor used in the reaction will vary depending on the desired thickness of the silica shell. Increasing the silica or silica precursor concentration can increase the thickness of the silica shell. Suitable concentrations of silica or silica precursor are in the range of 10 to 100 mM, especially 20 to 80 mM.

The reaction time can also be used to vary the thickness of the silica shell of the nanocapsule. Increasing the reaction time may increase the thickness of the silica shell. Reaction times may range from 1 hour to 100 hours, for example 10 hours to 80 hours, 20 to 70 hours or 30 to 50 hours, including all numbers of hours and parts thereof inbetween.

The pH of the reaction conditions for mixing the composition comprising micro- or nano-emulsion and silica precursor may be determined by the mineralizing biosurfactant used for stabilizing the micro- or nano-emulsion. In some embodiments, the pH used is suitable to maximise the charges on the charged peptide module and the hydrogen bonding propensity of the charged peptide module of the mineralizing biosurfactant. In some embodiments, the pH is between 7 and 9, especially 7 and 8.5 or 7 and 8, more especially about 7.5. Varying the pH of the reaction composition comprising micro- or nano-emulsion and silica precursor may also be used to vary the thickness of the silica shell.

The thickness of the silica shell may be tuned for a particular thickness by varying the concentration of the silica or silica precursor, varying the pH of the reaction composition and/or varying the reaction time.

In some embodiments, the silica shell has a thickness in the range of 5 to 100 nm, especially 5 to 20 nm. In some embodiments, the release of the compound to be delivered is by diffusion of the compound through the silica shell. In some embodiments, the release of the compound to be delivered is released at least in part, by the breakdown of the silica shell. In some embodiments, the thickness of the silica shell allows control of the rate of release of the active payload.

The silica or silica precursor is mixed with the stabilized nanoemulsion by gentle stirring. Suitable stirring methods will be known to those in the art, for example, mechanical stirring or magnetic stirring.

In yet another embodiment, there is provided a composition comprising a micro- or nano-capsule of the invention together with a suitable carrier.

Suitable carriers are determined by the use of the composition. For example, compositions for use in pharmaceutical or diagnostic applications will include a pharmaceutically acceptable carrier, compositions for use in veterinary applications will include a veterinary acceptable carrier, compositions for use in agricultural, household or environmental applications will include carriers acceptable for use in these environments. A person skilled in the art could determine suitable carriers for a specific use.

4. Applications

The micro- or nano-capsules of the present invention can be used to deliver one or more compounds such as pharmaceutical or veterinary products, agricultural products such as herbicides or insecticides or environmental or household products such as insecticides.

In some cases, the micro- or nano-capsule will be delivered to an environment that will cause rapid breakdown of the silica shell and immediate release of the active payload as a bolus dose. In other cases, the nanocapsule will be delivered to an environment which will cause gradual breakdown of the silica shell causing delayed release of the active payload. In yet other cases, the nanocapsule enables slowed release of the active payload over a period of time. In some embodiment, the active payload diffuses out of the micro- or nano-capsule over a period of time. In other embodiments, the active payload is released by diffusion at different times as the silica shell breaks down.

The micro- or nano-capsules of the invention may be useful in delivery of pharmaceutical compounds, particularly compounds that have limited solubility in aqueous or polar solvents. The micro- or nano-capsules may be tailored to have a particular silica shell thickness to allow controlled release such as immediate release, delayed release or slow release of the pharmaceutical compound. In some embodiments, a composition comprising multiple micro- or nano-capsules having different silica shell thicknesses to provide an extended release or slow release profile.

In some embodiments, the active payload is a diagnostic agent which is delivered to allow imaging such as magnetic resonance imaging or fluorescent imaging. In these embodiments, the micro- or nano-capsule may have a silica shell thickness that is suitable for delivery of the imaging agent as a bolus. Optionally the micro- or nano-capsule may be further modified to include a targeting agent such that the imaging agent is delivered to the target tissue or organ.

In some embodiments, the active payload is an immunogenic compound such as an antigen to provide a vaccine. In some embodiments, the antigen-loaded micro- or nano-capsule is stable until it is delivered to the individual in need of vaccination. Advantageously, these nanocapsule vaccine compositions may have an extended shelf life compared to solutions of antigen and/or may be stable without refrigeration allowing storage without cold chain requirements. The thickness of the silica shell on the nanocapsule shell may also be tailored to give a rate of delivery of antigen over a period of time and thereby providing a "single shot" vaccine. In some embodiments, the kinetics of release of the active compound may be further controlled by incorporating the compound in nanoparticles that are released from the micro- or nano-capsules and then the compound is released from the nanoparticles.

In some embodiments, the active payload is a small molecule such as a metalloprotease inhibitor, optionally incorporated into a nanoparticle, that is released to treat a human or animal disease, for example, laminitis in horses.

In some embodiments, the active payload is a pesticide such as an insecticide or combination of insecticides. The pesticidal micro- or nano-capsule compositions may be tailored to provide storage stability yet allow rapid release of the pesticide to provide fast "knock-down" of the invading pest, or may include a thick silica shell allowing slow release of a pesticidal amount of compound over a period of time to give long term protection of an agricultural, industrial or household environment. In particular embodiments, the active payload is a termiticide and the composition is suitable for preventing or controlling termite infestations.

In some embodiments, the active payload is a pesticide such as a herbicide or combination of herbicides. The herbicidal nanocapsule compositions may be tailored to allow immediate release of the herbicide to provide rapid control of weeds or unwanted plants, or may include a thick silica shell allowing slow release of a herbicidal amount of compound over a period of time to give long term control or prevention of weed infestation.

EXAMPLES

SEQ ID NO: 153 ($M_w$ 3643.2) and SEQ ID NO: 154 ($M_w$ 3632.4) peptides with 95% purity were custom synthesized by Peptide 2.0 Inc. (Chantilly, Va., USA). The peptides were dissolved in water and lyophilized prior to use, and the concentrations were determined by reversed-phase high-performance liquid chromatography (RP-HPLC). Miglyol® 812 (Axo Industry SA, Wavre, Belgium) was purified by passing the oil through dry silica gel column prior to use. 4-(2-hydroxyethyl)piperazine-1-ethanesulfonic acid buffer (HEPES, ≥99%), zinc chloride ($ZnCl_2$, ≥98%) and tetraethoxysilane (TEOS, ≥99%) were obtained from Sigma and used as received. Water was obtained from a Milli-Q (Millipore, New South Wales, Australia) system with a 0.22 µm filter and had a resistivity of >18.2 MΩcm. Piranha solution for acid washing of glassware was prepared from equal volumes of 30% hydrogen peroxide (Rowe Scientific Pty Ltd, Queensland, Australia) and 98% sulfuric acid (Chem-Supply Pty Ltd, South Australia, Australia). All glassware used to hold peptide solution was (i) soaked in 1% detergent solution (Decon 90, Decon Laboratories Ltd, East Sussex, U.K.), (ii) rinsed with 6 volumes of Milli-Q water, (iii) soaked for 15 mins in piranha solution, and (iv) rinsed with 10 volumes of Milli-Q water.

The size distribution profile of the nanoemulsions and nanocapsules was determined by dynamic light scattering (DLS, Malvern Zetasizer Nano ZS) and the samples were diluted by a factor of 100 prior to the measurement. The morphology and shell thickness of the nanocapsules were examined by transmission electron microscopy (TEM, JEOL 1010, 100 kV accelerating voltage). Samples (2 µL) were taken directly from the reaction mixtures, deposited onto Formvar-coated copper grids (200 mesh), and left to air-dry prior to examination. Samples were also analyzed for high-resolution (HR) TEM (JEOL 2100, 200 kV accelerating voltage) equipped with an energy dispersive X-ray spectroscopy (EDS) detector. The formation of amorphous silica was verified by selected area electron diffraction (SAED) in HRTEM.

Example 1: Precipitation of Silica by Biosurfactants

To test whether biosurfactants SEQ ID NO: 153 and SEQ ID NO: 154 were able to precipitate silica, separate aqueous solutions of SEQ ID NO: 153 and SEQ ID NO: 154 (400 µM) in HEPES buffer (25 mM) at pH 7.5 and 8.0 were prepared and TEOS (80 mM) was added. A solution of each biosurfactant was retained without TEOS as a control. The mixtures were gently stirred at room temperature. A transparent gel-like precipitate formed within a few minutes in those compositions which had TEOS added whereas the control remained a solution. The precipitate was isolated and extensively washed with water and vacuum dried. The precipitate was analyzed by elemental analysis using EDS in conjunction with scanning electron microscopy (SEM, JEOL 6610). The analysis showed the precipitate to be silica ($SiO_2$). Excess oxygen, carbon and sulfur also found in the analysis were consistent with entrapped peptide. This demonstrated that the peptides of SEQ ID NO: 153 and SEQ ID NO: 154 can nucleate silica.

Example 2: Formation of Nanoemulsions with SEQ ID NO: 153 and SEQ ID NO: 154

Separate solutions of SEQ ID NO: 153 (400 µM) and SEQ ID NO: 154 (400 µM) in HEPES buffer (25 mM, pH 7.0) in the presence of ZnCl$_2$ (800 µM) were mixed with Miglyol® 812 (2% v/v) by sonication (Branson Sonifier 450, 10 W, 4×30 s burst and interspersed with cooling in an ice bath for 60 s). After sonication, the compositions were macroscopically identical and homogeneous with cloudy appearance.

The nanoemulsions were analyzed by dynamic light scattering (DLS). The number-average diameter ($d_n$) of the oil droplets in the nanoemulsions were ~80 nm (polydispersity index (PDI)=0.329) for SEQ ID NO: 153 and ~40 nm (PDI=0.293) for SEQ ID NO: 154.

The nanoemulsion compositions (1 mL) were dialyzed against HEPES buffer (500 mL, 25 mM, pH 7.5 or 8.0) using a 10 kDa cellulose membrane to adjust pH of each nanoemulsion and to remove residual peptide. After dialysis for 20 hours there was only a slight increase, approximately 5%, in the number-average diameter of nanoemulsions stabilized by either SEQ ID NO: 153 or SEQ ID NO: 154 and the PDIs remained similar. The nanoemulsions were stable to dialysis.

Example 3: Formation of Nanocapsules from Nanoemulsions

Each of the dialyzed nanoemulsion compositions from Example 2 at pH 7.5 or 8.0 were divided into a number of separate glass vials. One composition of each peptide nanoemulsion at each pH was retained as a control. To the other compositions, three concentrations of TEOS were added to separate vials, 20 mM, 40 mM and 80 mM, and the compositions were gently stirred for 20 to 50 hours. The compositions were then analyzed by DLS and a size increase consistent with the formation of a thick layer surrounding the oil droplet core in TEOS-containing solutions was observed. The results for nanocapsules comprising SEQ ID NO: 154 are shown in FIGS. 2 to 5.

Figure 2:
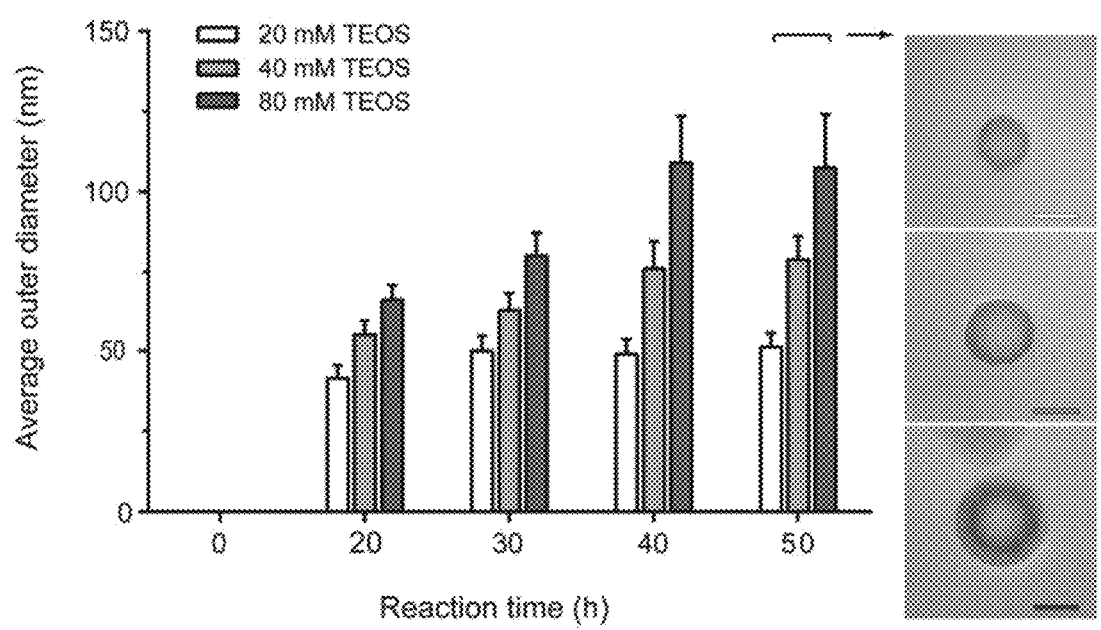
FIG. 2 is a graphical representation of the effect of TEOS concentration ($C_{TEOS}$) and reaction time (t) on the diameter of the nanocapsules prepared from a nanoemulsion stabilized by SEQ ID NO: 154 in 25 mM HEPES buffer, pH 7.5 (left panel). A photographic representation showing TEM images of individual silica nanocapsules (right panel) produced at pH 7.5 after 50 hours reaction of the nanoemulsion with 20 mM (top), 40 mM (middle) and 80 mM (bottom) TEOS in 25 mM HEPES buffer. Scale bars are 50 nm.

FIG. 2 demonstrates that the size of the nanocapsules formed with SEQ ID NO: 154 increases with concentration of TEOS added and the reaction time. These results were confirmed by TEM where the presence of the silica shell was shown and an increase in thickness with increasing TEOS concentration (FIG. 3) and increasing reaction time (FIG. 4) was demonstrated. SAED indicated the silica shells exhibit amorphous form as indicated by a diffuse ring pattern for the silica shell.

After 20 hours silicification of peptide nanoemulsions with 80 mM TEOS in 25 mM HEPES buffer, DLS results revealed a decrease in the polydispersity indexes of the nanocapsules formed with SEQ ID NO: 153 at pH 7.5 (PDI=0.242) and SEQ ID NO: 154 at pH 7.5 (PDI=0.146) and pH 8.0 (PDI=0.233). This suggests the mineralizing biosurfactants are covered by a condensed silica network after silicification yielding uniform structures. An increased PDI was observed for SEQ ID NO: 153 at pH 8 (PDI=0.794) suggesting flocculation of the nanocapsules.

The shell thickness of at least 100 individual nanocapsules were measured by TEM (a dark ring around the perimeter of the bright core). The silica layer formed on SEQ ID NO: 153 and SEQ ID NO: 154 nanoemulsions at pH 7.5 was 22±5 nm and 12±2 nm thick respectively and at pH 8.0, 35±5 nm and 27±6 nm respectively. This demonstrates that the thickness of the silica shell can be tuned by adjusting pH as shown on SEQ ID NO: 154 nanoemulsions in FIG. 5.

Figure 3:
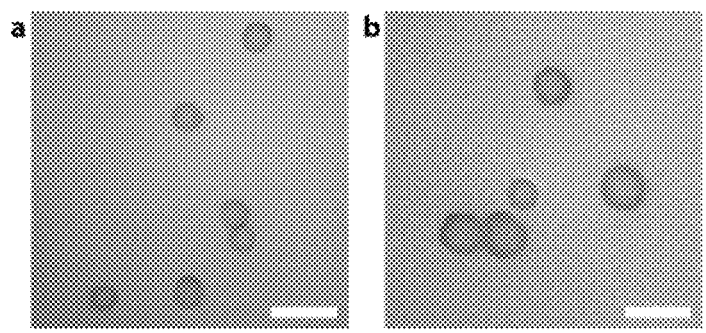
FIG. 3 is a photographic representation showing TEM images of silica nanocapsules produced at pH 7.5 after 30 hours reaction of nanoemulsion stabilized by SEQ ID NO: 154 with TEOS in 25 mM HEPES buffer at a TEOS concentration of a) 20 mM and b) 40 mM. Scale bars are 100 nm.
Figure 4:
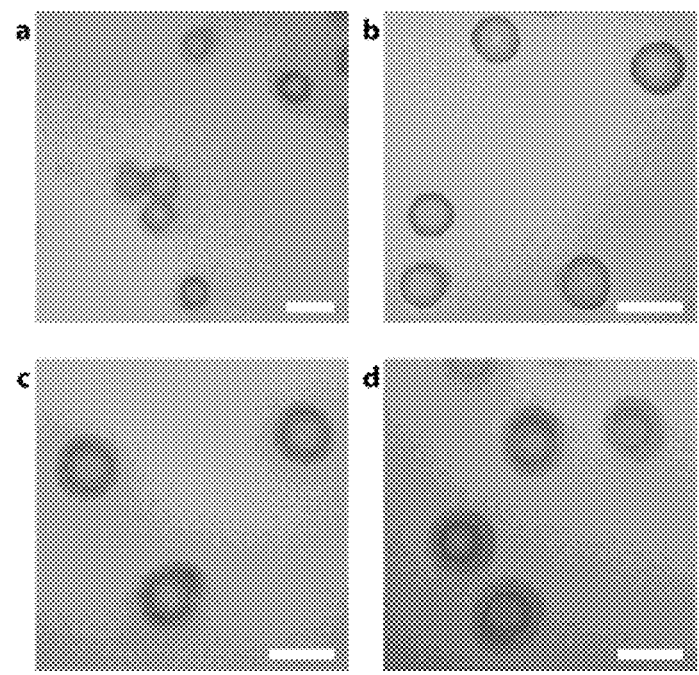
FIG. 4 is a photographic representation of TEM images of silica nanocapsules produced at pH 7.5 after a) 20 hours, b) 30 hours, c) 40 hours and d) 50 hours reaction of nanoemulsion stabilized by SEQ ID NO: 154 with 80 mM TEOS in 25 mM HEPES buffer. Scale bars are 100 nm.
Figure 5:
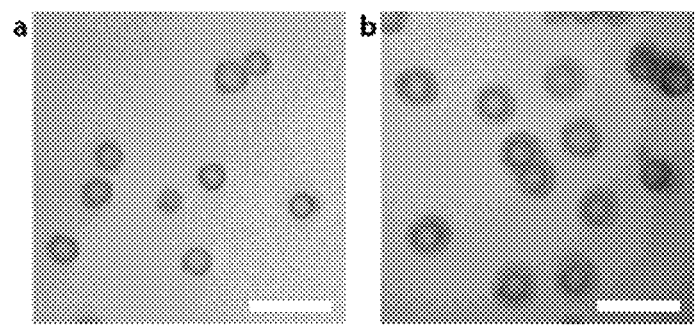
FIG. 5 is a photographic representation of TEM images of silica nanocapsules produced at pH a) 7.5 and b) pH 8 after 20 hours reaction of nanoemulsion stabilized by SEQ ID NO: 154 with 80 mM TEOS in 25 mM HEPES buffer. Scale bars are 200 nm.

Varying reaction time and TEOS concentration also affected the thickness of the silica shell. As expected, the nanocapsule silica shell thickness increased regularly with TEOS concentration (FIG. 3) and reaction time (FIG. 4). For example, after 30 hours silicification of SEQ ID NO: 154 nanoemulsions with 20 mM, 40 mM and 80 mM TEOS in 25 mM HEPES buffer, pH 7.5, the thickness of the silica shell was measured at 5±1 nm, 10±2 nm and 16±3 nm respectively (FIG. 3). Once the nanocapsules reached about 20 nm ($C_{TEOS}$=80 mM, t=40 hr) flocculation of the nanocapsules started to occur. This demonstrates that well dispersed nanocapsules having different silica shell thickness may be obtained by an interplay between TEOS concentration and reaction time.

Example 4: Synthesis of Biocide-Loaded Silica Nanocapsules

Nanoemulsion was prepared by homogenization of fipronil-loaded Miglyol® 812 at 2% v/v in HEPES buffer (25 mM, pH 7.5) containing the biosurfactant peptide Ac-MKQLAHSVSRLEHA-RKKRKKRKKRKKGGGY-CONH$_2$ (SEQ ID NO: 154, 400 µM) and ZnCl$_2$ (800 µM) using an ultrasonicator (Branson Sonifier 450, 10 W, 4×30 s bursts and interspersed with cooling in an ice bath for 60 s). The fipronil-loaded nanoemulsion (1 mL) was dialyzed against HEPES buffer (500 mL, 25 mM, pH 7.5) using 10 kDa cellulose membrane to adjust pH of the nanoemulsion and to remove residual peptide.

Aliquots (400 µL) of the nanoemulsions were transferred into 4 mL glass vials and TEOS at concentrations of 40 mM, 80 mM and 240 mM was added. The compositions were gently stirred at room temperature for 30 hours to provide oil-core/silica-shell nanocapsules.

Figure 6:
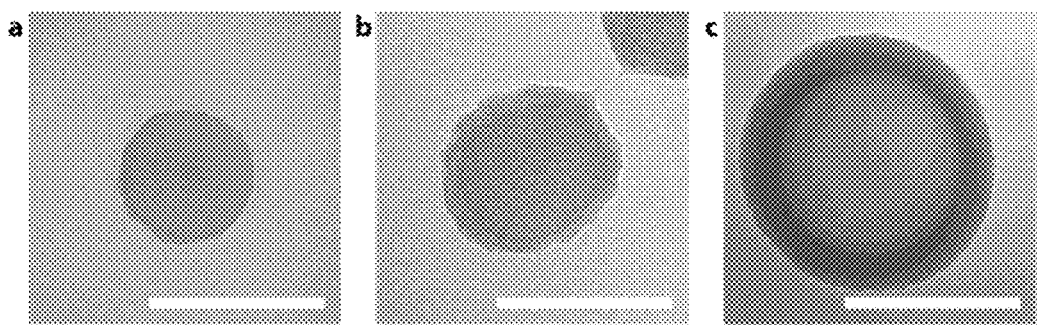
FIG. 6 is a photographic representation of TEM images of silica nanocapsules loaded with 0.05 mg/mL fipronil in Miglyol® 812 oil produced at pH 7.5 after 30 hours reaction of fipronil-loaded nanoemulsions stabilized by SEQ ID NO: 154 with a) 40 mM, b) 80 mM and c) 240 mM TEOS in 25 mM HEPES buffer, which resulted in sil heterocyclyl group may be substituted with one or more groups selected from —OH, —NH$_2$, —NHC$_1$—C$_3$alkyl, —OC$_1$—C$_3$alkyl, —SH, —SC$_1$—C$_3$alkyl, —CO$_2$H, —CO$_2$C$_1$—C$_3$alkyl, —CONH$_2$ or —CONHC$_1$—C$_3$alkyl.

The loaded nanocapsules have dense core under transmission electron microscope as shown in FIG. 6, in contrast to the light core shown by unloaded nanocapsules (FIGS. 2-5). Nanocapsules with three different silica shell thicknesses of 8±2 nm, 25±3 nm and 44±7 nm were produced using 40 mM (FIG. 6*a*), 80 mM (FIG. 6*b*) and 240 mM (FIG. 6*c*) TEOS, respectively.

The fipronil-loaded nanocapsules formed at each concentration of TEOS were analyzed directly by TEM. Samples of each thickness nanocapsules were also dialyzed against Milli-Q water to remove unreacted TEOS.

Example 5: In Vivo Efficacy of Fipronil-Containing Silica Nanocapsules on Termites Termites were collected from a *Coptotermes acinaciformis* colony and active worker termites were selected for the experiment. Prior to experiment, the termites were incubated at 28±1° C. in Petri dishes containing Whatman® cellulose filter paper to assess termite survival under incubation conditions. After 4 days, 26±8% mortality was observed.

Six samples were prepared and analyzed for response of fipronil.

Control: Milli-Q water
Termidor®: commercially-available Termidor® containing 0.05 mg/mL fipronil
0.05F-NE: nanoemulsion containing 0.05 mg/mL fipronil (as prepared in Example 4 without biosilicification step)
0.05F-NCB: silica nanocapsules loaded with 0.05 mg/mL fipronil having a silica shell thickness of 8±2 nm (as prepared in Example 4)

0.05F-NC25: silica nanocapsules loaded with 0.05 mg/mL fipronil having a silica shell thickness of 25±3 nm (as prepared in Example 4)

0.05F-NC44: silica nanocapsules loaded with 0.05 mg/mL fipronil having a silica shell thickness of 44±7 nm (as prepared in Example 4)

Figure 7:
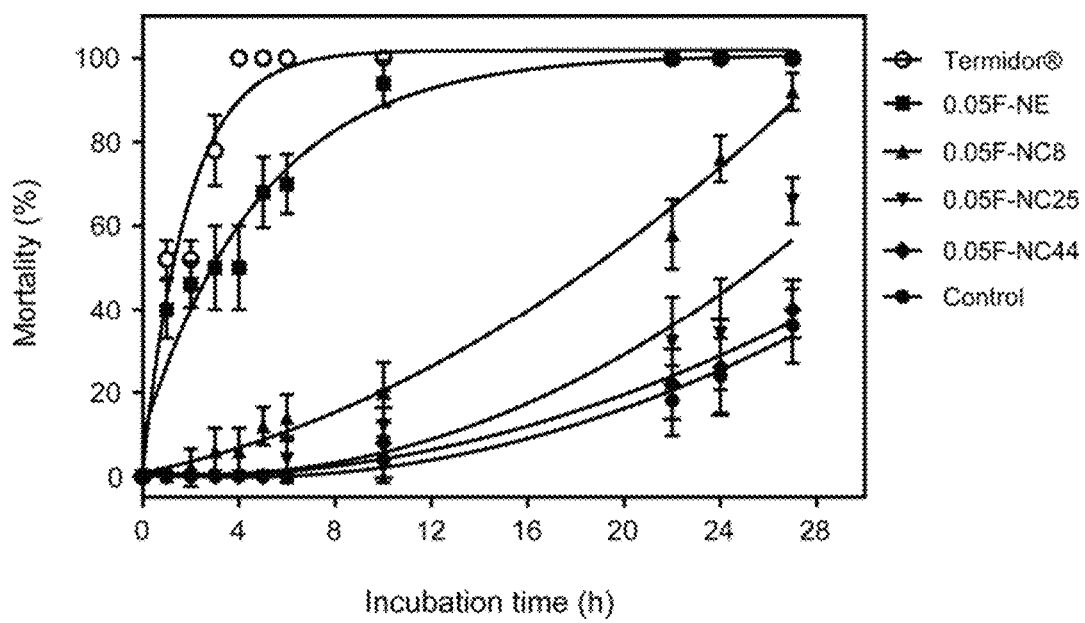

Treatment with each fipronil formulation or water against a group of termites was conducted in five replicates. Termite response (mortality) was examined during the treatment. Ten active worker termites were placed into a Petri dish (92×16 mm). Prior to treatment, termites in the Petri dishes were incubated at 2° C. for 2 mins to slow termite movement. Each of the fipronil formulations or water (5.5 µL) was topically applied on the dorsal thorax of termites. In cases where a droplet was misplaced or ran off, the treated termite was excluded from testing. Topically-dosed termites were left in Petri dishes until the droplet dried. Termites were then transferred to clean Petri dishes lined with a filter paper (42.5 mm, Whatman®). Each Petri dish was placed into a controlled environment chamber. The chamber (65×47×37.5 cm) containing a thermometer, a lid and a 11.5-L metal container with water and heater, maintained the temperature at 28±1° C., high humidity and, once covered with insulating material, total darkness (except during observation). Preliminary study showed that termites could survive under these conditions for at least 4 days. Mortality was recorded at 1, 2, 3, 4, 5, 6, 10, 22, 24 and 27 h after treatment (FIG. 7). The Petri dishes were removed from the chamber whenever needed and the lids were opened with the least possible disturbance. A termite was considered dead when it was on its back or side (not supported by legs) and not able to move even after prodding with a soft brush.

Rapid mortality of termites was observed when they were treated with commercially-available Termidor® containing fipronil or 0.05F-NE. Termidor® gave a burst release of fipronil during the first hour resulting in 50% mortality with 100% mortality at 4 h (FIG. 7). 0.05F-NE exhibited a two-step release profile. The first stage of fipronil release showed a significant initial burst effect, reflected by the mortality of almost 50% within the first 4 h, and followed by a more sustained release over 22 h (FIG. 7). 0.05F-NE gave a slightly reduced mortality within the time frame as compared to Termidor®. In contrast, silica nanocapsules showed more sustained release as a result of the silica shell. First mortality was found after 4 h (6%), 6 h (4%) and 10 h (8%) for 0.05F-NC8, 0.05F-NC25 and 0.05F-NC44, respectively (FIG. 7). Mortality then gradually increased in a way dependent on shell thickness, suggesting that the silica shell provided an effective barrier for the controlled diffusion of encapsulated fipronil.

Example 6

Fipronil-loaded silica nanocapsules with 44±7 nm shell thickness was evaluated for the slow release performance by remote feeding treatment on termites *Coptotermes acinaciformis*. For feeding treatment, 1 mg/mL fipronil solubilized in Miglyol® 812 was used as oil phase and fipronil-loaded nanocapsule having a 44 nm shell (1F-NC44) was then prepared using 240 mM TEOS as previously described in Example 4. Three samples were compared, including Milli-Q water as a control, commercially-available Termidor® containing 1 mg/mL fipronil and 1F-NC44. Treatment of each fipronil formulation or water was conducted in four or two replicates, respectively. Termite response (mortality) was examined during the treatment.

Termites (7.5 g≈1,500 workers and soldiers of *Coptotermes acinaciformis*) were placed into 750 mL containers with 150 g roasted *Nasutitermes magnus* mound material and 50 g boiled water. The mound material was roasted in an oven at 200° C. for 60 minutes to reduce the incidence of microbes and then ground with a mortar and pestle. The material is a slightly nutritious building substrate and was included to mimic the termite natural environment. A clear vinyl tubing (150×6 mm diameter) connected the container to a 70 mL feeding vial. Each vial was filled with moist α-cellulose bait (50 g boiled water and 20 g α-cellulose). Each assembly was placed into a controlled-environment chamber. The chamber (65×47×37.5 cm) containing a thermometer, a lid and a 11.5-L metal container with water and heater was maintained at 26±1° C., high humidity and, once covered with insulating material, total darkness (except during observation). The termites in the ten assemblies were allowed to acclimatize to these conditions for 4 days and began feeding on the bait as indicated by the presence of enclosed tunnels and chambers built in the cellulose. On day 4, 0.5 mL Termidor®, 0.5 mL 1F-NC44 or 0.5 mL water was transferred into each feeding vial. The assembled feeding devices were removed from the chamber and observed whenever needed with the least possible disturbance. Observation of each assembly was made daily using a Termatrac® T3i device (Termatrac® Pty Ltd, Beenleigh, Queensland, Australia) to detect movement of living termites. Lack of movement indicated 100% mortality of termites and destructive inspections were made to confirm. The termite colony in one Termidor® container (out of four) remained alive at 7 days because termites did not enter into the vial containing Termidor®-treated cellulose. Similarly, two 1F-NC44 containers (out of four) were still alive at 7 days because the tube entrance to the vial containing 1F-NC44-treated cellulose was blocked with mud built by termites. These containers were not included for further consideration. The two control colonies survived throughout the study.

Figure 8:
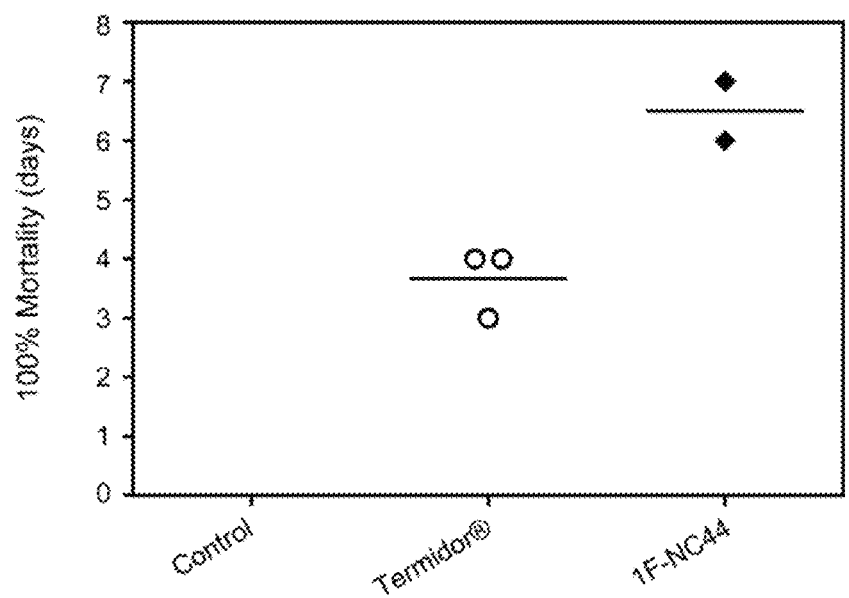

It was observed that termites built mud and cellulose surrounding the connector tubes as well as galleries within the baits, indicating that termites were responding to the cellulose. As termites carried the cellulose from the feeding vial back to the container, they transferred it to other termites within the colony. Termidor®-treated cellulose caused 100% mortality to termite colonies after 3 days, whereas more delayed mortality (6 days) was observed after treatment using 1F-NC44-treated cellulose (FIG. 8). Delayed mortality as for the silica nanocapsule increases the likelihood of horizontal transfer of fipronil hence allowing improved area-wide control of termite populations.

Example 7: Design and Production of a Recombinant Protein Capable of Making Silica Nanocapsules To develop a scalable and sustainable technology to make silica nanocapsules, a mineralizing biosurfactant protein (MDPS MKQLADS LHQLARQ VSRLEHA DPS MKQLADS LHQLARQ VSRLEHA DPS MKQLADS LHQLARQ VSRLEHA DPS MKQLADS LHQLARQ VSRLEHA EPS-RKKRKKRKKRKKGGGY, SEQ ID NO: 155), which can be produced directly from recombinant DNA, was designed consisting of one surface active polypeptide module ((MD(PS-MKQLADS-LHQLARQ-VSR-LEHA-D)$_4$, SEQ ID NO: 85) capable of stabilizing nanoemulsions and another positively charged peptide module (RKKRKKRKKRKKGGGY, SEQ ID NO: 132) inducing biosilicification at oil-water interfaces at near neutral pH.

Figure 9:
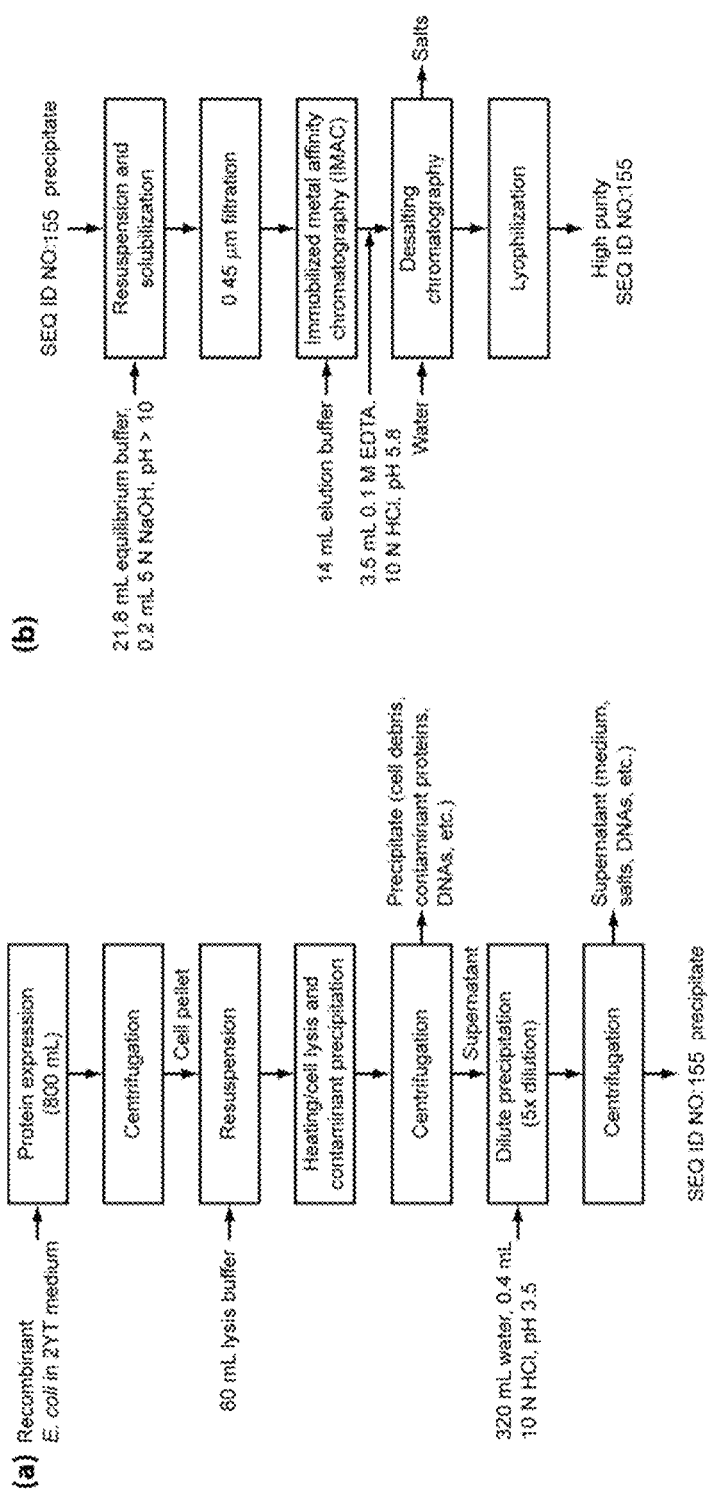

SEQ ID NO: 155 can be produced at high level of solubility in genetically-modified of the industrially relevant bacterium *Escherichia coli*. With an aim of obtaining high purity of SEQ ID NO: 155, a precipitation-based process has been developed based on purification method of SEQ ID NO: 85 described in WO 2012/079125 (FIG. 9a) coupled with chromatography technique (FIG. 9b).

Expression construct and transformation: pET-48b(+) plasmid with nucleotide sequence encoding for SEQ ID NO: 155 (1 µL) (Protein Expression Facility, The University of Queensland) was added into *E. coli* BL21(DE3) competent cells (50 µL) and incubated on ice for 30 min, heat-shocked at 42° C. for 45 s, and incubated on ice for further 2 min. Then, 0.95 mL Luria Bertani (LB) medium (10 g/L NaCl, 10 g/L tryptone, 5 g/L yeast extract, water) was added into the cell suspension and incubated at 37° C., 220 rpm for 1 h. The cell suspension (100 µL) was plated on LB agar (10 g/L NaCl, 10 g/L tryptone, 5 g/L yeast extract, 15 g/L agar, water) and incubated at 37° C., 180 rpm for 16 h. Following transformation, a single colony was picked from the plate, placed in 5 mL 2× yeast extract and tryptone (2YT) medium (5 g/L NaCl, 16 g/L tryptone, 10 g/L yeast extract, water), and incubated at 37° C., 180 rpm for 16 h. All media for cultures were supplemented with 15 µg/mL antibiotic (i.e., kanamycin sulfate). To preserve the clones, the overnight culture (0.5 mL) and 60 v/v % glycerol (0.5 mL) were mixed well, frozen in liquid nitrogen, and stored at −80° C. for later use.

Protein expression: A single colony from a freshly streaked plate was inoculated into 5 mL 2YT medium and incubated at 30° C., 180 rpm for 16 h. 2YT medium (800 mL) was inoculated with 800 µL of the overnight culture ($OD_{600}$=2) in a 2.5 L-baffled shake flask and incubated at 37° C., 180 rpm until $OD_{600}$ reached approximately 0.5. Protein expression was induced by adding isopropyl β-D-1-thiogalactopyranoside (IPTG) to a final concentration of 1 mM and then incubated at 37° C., 180 rpm for further 4 h. A final $OD_{600}$ of 2 was routinely obtained. Cell pellet was harvested by centrifugation at 4° C., 6250×g for 10 min, washed with the supernatant (40 mL) and then centrifuged at 4° C., 4700×g for 10 min. The cell pellet was stored at −80° C. until further processing. All media for cultures were supplemented with 15 µg/mL kanamycin sulfate.

Heating/cell lysis, contaminant precipitation and dilute precipitation: The cell pellet was resuspended in 80 mL lysis buffer (25 mM sodium phosphate, 1.2 M NaCl, 1 M $Na_2SO_4$, pH 7.5). The mixture was transferred into a 250 mL-conical flask and then incubated at 90° C. with stirring at 1000 rpm for 30 min in a thermostatic bath equipped with an electronic contact thermometer (IKA®-Werke GmbH & Co. KG, Germany) During the heating, the opening of the flask and the bath were covered with aluminium foil to minimize evaporation. The cell lysate was then centrifuged at 20° C., 51500×g for 5 min. The supernatant was collected and diluted 5-fold with water, and the pH was adjusted to pH 3.5 by adding 10 N HCl to allow precipitation of SEQ ID NO: 157. Then, the mixture was centrifuged at 4° C., 33750×g for 30 mM The precipitated sample was resuspended in equilibrium buffer (25 mM sodium phosphate, 1.2 M NaCl, 20 mM imidazole, pH 7.5) and solubilized by adjusting the pH to pH>10 using 5 N NaOH.

Figure 10:
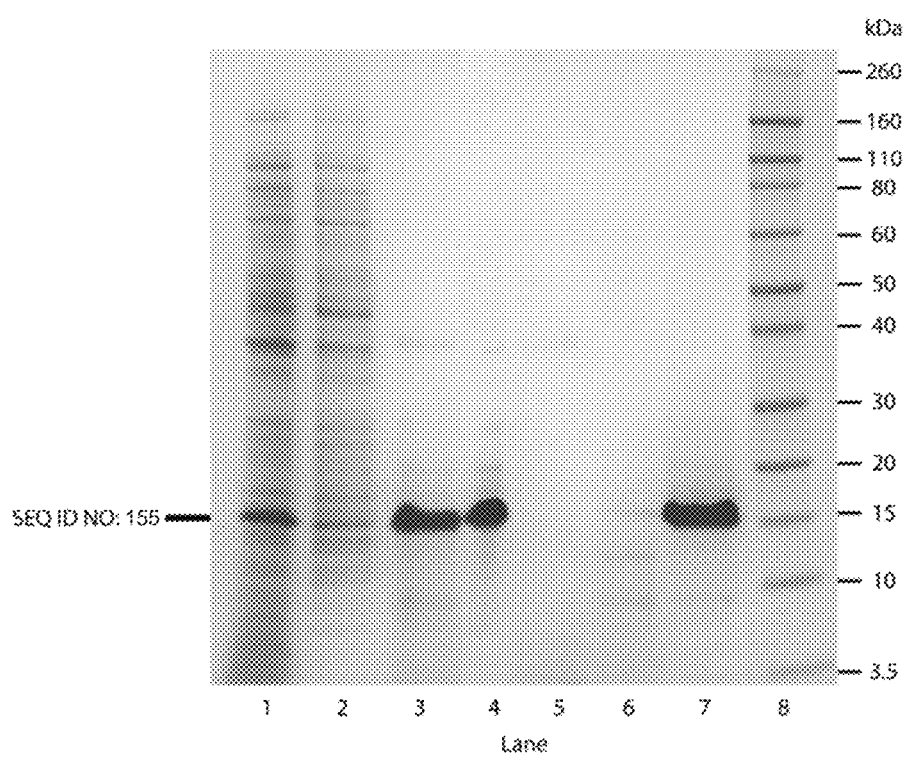

The protein solution produced after heating/cell lysis, contamination precipitation and dilute precipitation consisted of SEQ ID NO: 155 based on the SDS-PAGE result (FIG. 10, lane 4). Although the protein could be used to facilitate formation of nanoemulsions, the nanoemulsions gave negative surface charge due to the presence of significant amount of DNA contamination at a concentration of 63.18±6.14 ng DNA/mg SEQ ID NO: 155, and, as a result, silica shell could not be formed at the interfaces. Therefore, a further purification process using chromatography method was developed to remove DNAs from SEQ ID NO: 155 (FIG. 9b).

Figure 11:
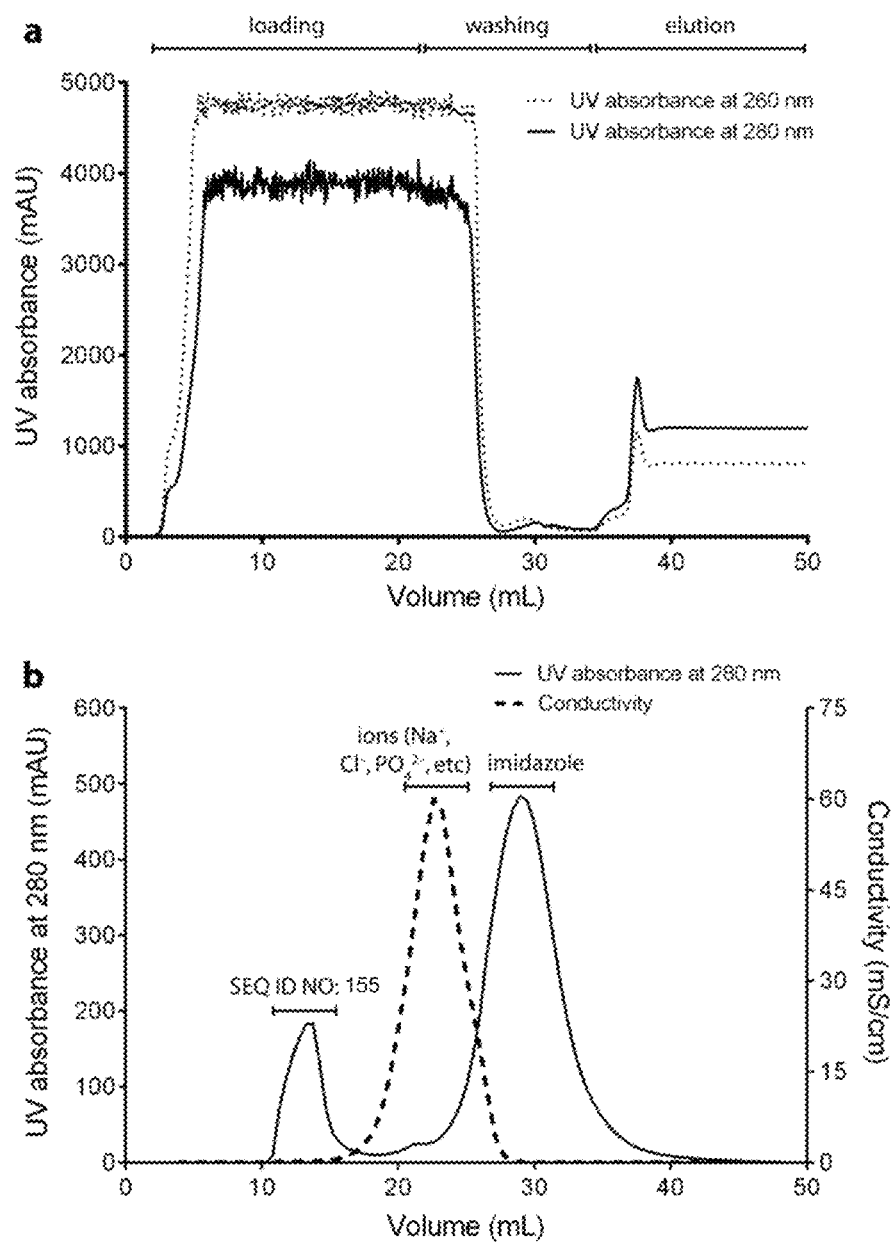

Chromatography: Immobilized metal ion affinity chromatography (IMAC) was conducted by using an ÄKTA Explorer 10 system (GE Healthcare, Sweden) with $Ni^{2+}$ charged IMAC Sepharose High Performance resin (GE Healthcare, UK) packed into a 15 mm diameter Omnifit glass column (Omnifit, N.J., USA) to a bed height of 75 mm which is equivalent to 5.5 mL column volume (CV). Prior to loading, the protein solution was filtered using a 0.45 µm syringe filter with MF-Millipore® mixed cellulose ester membrane (Millipore, Australia), and the column was equilibrated with 3 CV of equilibrium buffer (25 mM sodium phosphate, 1.2 M NaCl, 20 mM imidazole, pH 7.5). The protein solution was then loaded into the column at a flow rate of 1 mL/min. Unbound components including DNAs as indicated by higher UV absorbance at 260 nm than at 280 nm were washed out with 2 CV of equilibrium buffer. Bound protein was then eluted using 2.5 CV of elution buffer (25 mM sodium phosphate, 1.2 M NaCl, 500 mM imidazole, pH 7.5) (FIG. 11a). The eluted fraction was mainly SEQ ID NO: 155 based on the SDS-PAGE analysis (FIG. 10 lane 7) with significantly reduced DNA fraction of 1.90±0.48 ng DNA/mg SEQ ID NO: 155. To chelate $Ni^{2+}$ ions leaked after IMAC step, the pH of the collected fractions was adjusted to pH 5.8 by adding 10 N HCl, and ethylenediaminetetraacetic acid disodium salt (EDTA) was added to a final concentration of 20 mM.

Following the IMAC process, desalting of the protein solution with water was conducted by using an ÄKTA Explorer 10 system with a Sephadex G-25 resin (GE Healthcare, UK) packed into a 20 mm diameter Omnifit glass column to a bed height of 129 mm (CV=22.8 mL). The protein solution was loaded into the column pre-equilibrated with water at a flow rate of 1 mL/min. The protein fraction after desalting process was collected (FIG. 11b) and lyophilized at −55° C., 0.08 mbar for 16 h.

Figure 12:
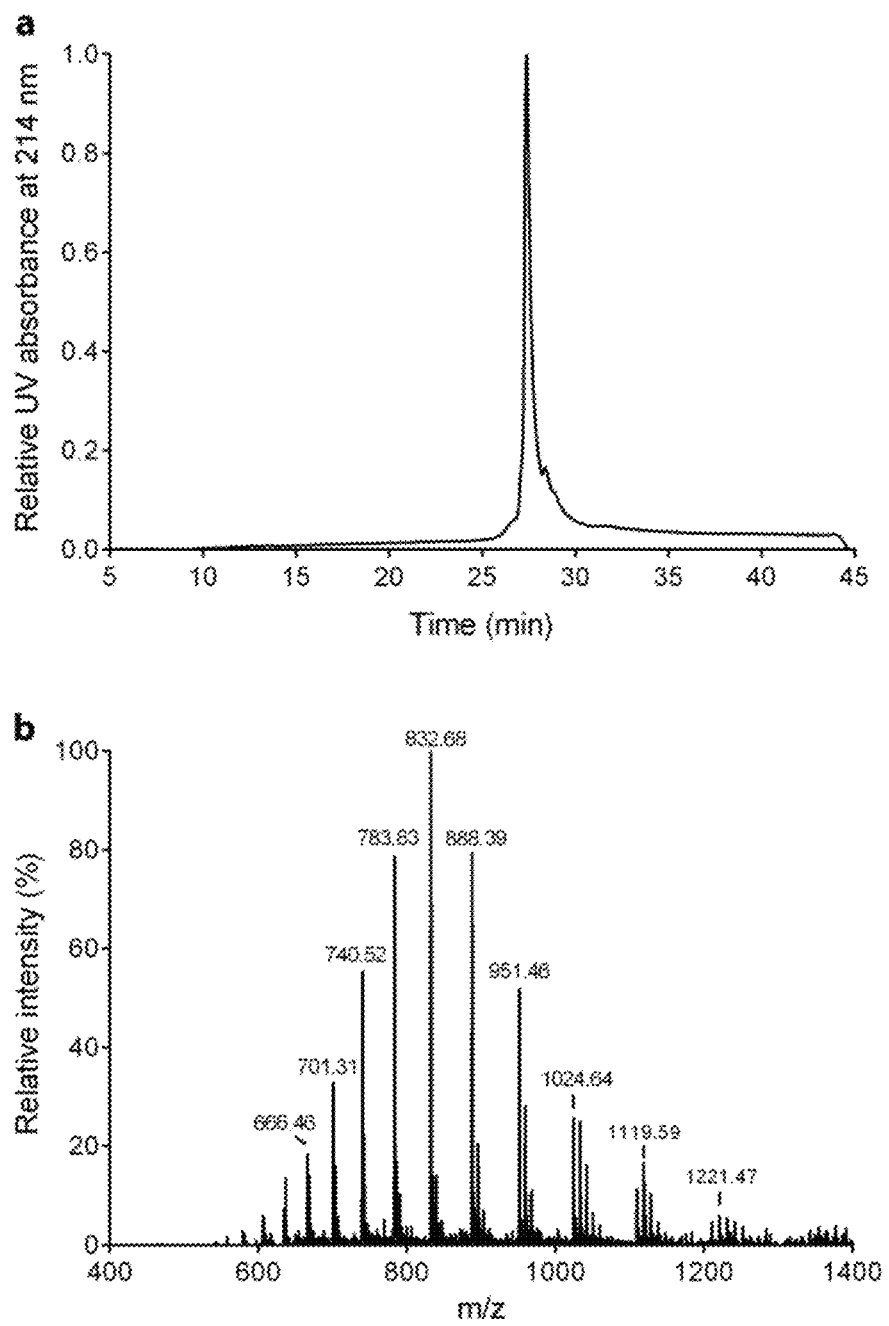

After the chromatography purification steps, DNA fraction in SEQ ID NO: 155 solution is 1.82±0.46 ng DNA/mg SEQ ID NO: 155 with final yield of SEQ ID NO: 155 of approximately 7.22 mg. As analyzed by reversed-phase high performance liquid chromatography (RP-HPLC) and mass spectrometry (MS), high purity SEQ ID NO: 155 can be obtained (FIG. 12a), and the calculated molecular weight of SEQ ID NO: 155 based on the mass spectrum (FIG. 12b) is 13308.16 Da which is very close to its theoretical molecular weight i.e., 13299.31 Da.

Figure 13:
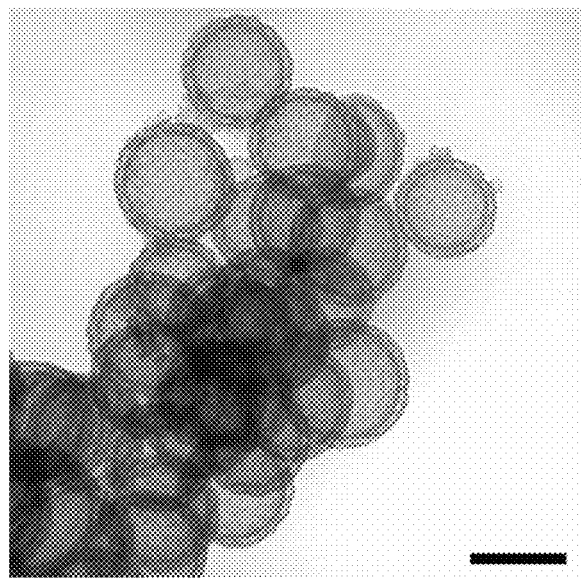

Example 8: Formation of Nanocapsules from Nanoemulsions Using Recombinant Protein SEQ ID NO: 155 was used to facilitate formation and stabilization of nanoemulsions, and subsequently direct nucleation and growth of silica shell encasing the nanoemulsion template. A solution of SEQ ID NO: 155 (115 µM) in HEPES buffer (25 mM, pH 7.5) was mixed with Miglyol® 812 oil (10% v/v) by sonication at 10 W using Branson Sonifier 450 for 4×30 s burst and interspersed with cooling in an ice bath for 60 s. An aliquot of SEQ ID NO: 155 nanoemulsions (400 µL) was transferred to a glass vial and added with TEOS (80 mM). The mixture was then stirred at room temperature for 20 h to form silica shell surrounding the nanoemulsions. The outer diameter and shell thickness of the nanocapsules as measured by TEM were 249±29 nm and 26±2 nm as shown in FIG. 13.

REFERENCES

Lou, X. W., Archer, L. A. & Yang, Z. Hollow micro-/nanostructures: synthesis and applications. *Adv. Mater.* 20, 3987-4019 (2008).

Guerrero-Martinez, A., Pérez-Juste, J. & Liz-Marzán, L. M. Recent progress on silica coating of nanoparticles and related nanomaterials. *Adv. Mater.* 22, 1182-1195 (2010).

Schärtl, W. Current directions in core-shell nanoparticle design. *Nanoscale* 2, 829-843 (2010).

Burns, A., Ow, H., Wiesner, U. Fluorescent core-shell silica nanoparticles: towards "Lab on a Particle" architectures for nanobiotechnology. *Chem. Soc. Rev.* 35, 1028-1042 (2006).

Lu, A. H., Salabas, E. L., Schüth, F. Magnetic nanoparticles: synthesis, protection, functionalization, and application. *Angew. Chem. Int. Ed.* 46, 1222-1244 (2007).

Barbé, Bartlett, J., Kong, L. G., Finnie, K., Lin, H. Q., Larkin, M., Calleja, S., Bush, A., Calleja, G. Silica particles: a novel drug-delivery system. *Adv. Mater.* 16, 1959-1966 (2004).

Caruso, F., Caruso, R. A., Mohwald, H. Nanoengineering of inorganic and hybrid hollow spheres by colloidal templating. *Science* 282, 1111-1114 (1998).

Cornelissen, J. J. L. M., Connor, E. F., Kim, H. C., Lee, V. Y., Magibitang, T., Rice, P. M., Volksen, W., Sundberg, L. K., Miller, R. D. Versatile synthesis of nanometer sized hollow silica spheres. *Chem Commun.* 1010-1011 (2003).

Kong, S. D., Zhang, W., Lee, J. H., Brammer, K., Lal, R., Karin, M., Jin, S. Magnetically vectored nanocapsules for tumor penetration and remotely switchable on-demand drug release. *Nano Lett.* 10, 5088-5092 (2010).

Hayashi, K., Nakamura, M. & Ishimura, K. In situ synthesis and photoresponsive rupture of organosilica nanocapsules. *Chem. Commun.* 47, 1518-1520 (2011).

Chen, H., He, J., Tang, H. & Yan, C. Porous silica nanocapsules and nanospheres: dynamic self-assembly synthesis and application in controlled release. *Chem. Mater.* 20, 5894-5900 (2008).

Li, J., Liu, J., Wang, D., Guo, R., Li, X., Qi, W. Interfacially controlled synthesis of hollow mesoporous silica spheres with radially oriented pore structures. *Langmuir* 26, 12267-12272 (2010).

Zhao, Y., Zhang, J., Li, W., Zhang, C., Han, B. Synthesis of uniform hollow silica spheres with ordered mesoporous shells in a CO(2) induced nanoemulsion. *Chem. Commun.* 2365-2367 (2009).

Kuwahara, Y., Yamanishi, T., Kamegawa, T., Mori, K., Che, M., Yamashita, H. Lipase-embedded silica nanoparticles with oil-filled core-shell structure: stable and recyclable platforms for biocatalysts. *Chem. Commun.* 48, 2882-2884 (2012).

Underhill, R. S., Jovanovic, A. V., Carino, S. R., Varshney, M., Shah, D. O., Dennis, D. M., Morey, T. E., Duran, R. S. Oil-filled silica nanocapsules for lipophilic drug uptake: implications for drug detoxification therapy. *Chem. Mater.* 14, 4919-4925 (2002).

Jovanovic, A. V., Underhill, R. S., Bucholz, T. L., Duran, R. S. Oil core and silica shell nanocapsules: toward controlling the size and the ability to sequester hydrophobic compounds. *Chem. Mater.* 17, 3375-3383 (2005).

Morse, D. E. Silicon biotechnology: harnessing biological silica production to construct new materials. *Trends Biotechnol.* 17, 230-232 (1999).

---

The claims defining the invention are as follows:

1. A mineralizing biosurfactant comprising:
   i) a surface-active polypeptide module at least 6 amino acid residues in length; and
   ii) a charged peptide module comprising the amino acid sequence of RKKRKKRKKRKKGGGY (SEQ ID NO: 132),
   wherein the surface-active polypeptide and the charged peptide modules are conjugated to one another; and
   wherein the surface-active polypeptide module comprises an amino acid sequence:

(a b c d e f g)$_n$ wherein n is an integer from 2 to 12;
      amino acid residues a and d are hydrophobic amino acid residues;
      at least one of residues b and c and at least one of residues e and f are hydrophilic amino acid residues, and the other of amino acid residues b and c and e and f are any amino acid residue; and amino acid residue g is any amino acid residue;
   wherein the mineralizing biosurfactant is capable of nucleating silica on the surface of a stabilized micro- or nano-emulsion.

2. The mineralizing biosurfactant, according to claim 1 wherein the surface-active polypeptide is an amphiphilic polypeptide.

3. The mineralizing biosurfactant according to claim 2 wherein the amphiphilic polypeptide has α-helical secondary structure with a hydrophobic face and a hydrophilic face.

4. The mineralizing biosurfactant according to claim 1 wherein n is 2 to 4.

5. The mineralizing biosurfactant according to claim 1 wherein each amino acid residue a and d is independently selected from the group consisting of L-alanine, L-valine, L-leucine, L-methionine, I, isoleucine, L-phenylalanine, L-tyrosine, D-alanine, D-valine, D-leucine, D-methionine, D-isoleucine, D-phenylalanine and D-tyrosine.

6. The mineralizing biosurfactant according to claim 1 wherein each amino acid residue b is independently selected from the group consisting of alanine, leucine, valine, methionine, isoleucine, L-serine, L-threonine, L-cysteine, L-tyrosine, L-asparagine, L-glutamine, L-lysine, L-arginine, L-histidine aspartic acid and glutamic acid.

7. The mineralizing biosurfactant according to claim 1 wherein each amino acid residue c is independently selected from the group consisting of L-serine, L-threonine, L-cysteine, L-tyrosine, L-asparagine, L-histidine, D-aspartic acid and L-glutamic acid.

8. The mineralizing biosurfactant according to claim 1 wherein each amino acid residue e is independently selected from the group consisting of L-alanine, L-D-isoleucine, L-serine, L-threonine, L-aspartic acid and L-glutamic acid, especially L-alanine, L-serine and L-glutamic acid.

9. The mineralizing biosurfactant according to claim 1 wherein each amino acid residue f is independently selected from the group consisting of L-serine, L-threonine, L-cysteine, L-tyrosine, L-asparagine, L-glutamine, L-arginine, D-aspartic acid and L-glutamic acid.

10. The mineralizing biosurfactant according to claim 1 wherein each amino acid residue g is independently selected from the group consisting of L-alanine, L-valine, L-isoleucine, L-serine, L threonine, L-asparagine L-lysine, L-glutamic acid and L-glutamine.

11. The mineralizing biosurfactant according to claim 1 having one of the following sequences:

```
                                          (SEQ ID NO: 154)
Ac-MKQLAHSVSRLEHARKKRKKRKKRKKGGGY-NH2,
or
                                          (SEQ ID NO: 155)
MDPSMKQLADSLHQLARQVSRLEHADPSMKQLADSLHQLARQVSRLEHA

DPSMKQLADSLHQLARQVSRLEHADPSMKQLADSLHQLARQVSRLEHAE

PSRKKRKKRKKRKKGGGY.
```

12. A stabilized micro- or nano-emulsion comprising an oil phase, an aqueous phase and a mineralizing biosurfactant according to claim 1, wherein the mineralizing biosurfactant is located in the region of the interface between the oil and aqueous phases.

13. The stabilized micro- or nano-emulsion according to claim 12 further comprising a metal ion selected from the group consisting of calcium, magnesium, copper, nickel and zinc ions.

14. A silica micro- or nano-capsule comprising an oil core stabilized by a surface film of mineralizing biosurfactant according to claim 1 and a silica shell encapsulating the stabilized oil core.

15. The silica nanocapsule according to claim 14 having an average diameter of between 70 and 500 nm or an average diameter of between 1 µm and 5 µm.

16. The silica micro- or nano-capsule according to claim 14 wherein the silica shell has a thickness in the range of 5 nm to 100 nm.

17. The silica micro- or nano-capsule according to claim 14 wherein the oil core further comprises a compound for delivery to a human or animal or a household, industrial or agricultural environment.

18. The silica micro- or nano-capsule according to claim 14 further comprising a pharmacokinetic modifying agent and/or a targeting agent, wherein said pharmacokinetic modifying agent and/or a targeting agent are located on the surface of the micro- or nano-capsule.

19. A composition comprising the micro- or nano-capsules according to claim 14 together with an acceptable carrier.

20. A method of making a silica micro- or nano-capsule comprising the steps of:
  A) forming a stabilized micro- or nano-emulsion by mixing a composition comprising:
    a) an oil phase;
    b) an aqueous phase; and
    c) a mineralizing biosurfactant according to claim 1; and
  B) mixing the nanoemulsion with silica or a silica precursor.

21. The method according to claim 20 wherein the micro- or nano-emulsion is formed by mixing, sonification or homogenisation.

22. The method according to claim 20 wherein the silica or silica precursor is selected from the group consisting of tetraethoxysilane, tetramethoxysilane, sodium silicate ($Na_2Si_3O_7$), dipotassium silicon triscatecholate ($K_2[Si(C_6H_4O_2)_3 \cdot 2H_2O]$), silica sol (silica nanoparticles with diameter of 10-12 nm, 40% $SiO_2$, 0.4% $Na_2O$), ethylene glycol modified silane ($SiC_2H_8O_7)_4$), methyltriethoxysilane, phenyltriethoxysilane and trimethylethoxysilane.

23. The method according to claim 20 wherein the reaction of step B) is mixed for 10 to 80 hours.

24. The method according to claim 20 wherein the reaction of step B) is carried out at a pH between 7 and 8.5.

* * * * *